US012760026B2

(12) United States Patent
Childers et al.

(10) Patent No.: US 12,760,026 B2
(45) Date of Patent: Oct. 13, 2026

(54) HETEROAROYL AMIDES AS LRRK2 INHIBITORS, PHARMACEUTICAL COMPOSITIONS, AND USES THEREOF

(71) Applicant: Merck Sharp & Dohme LLC, Rahway, NJ (US)

(72) Inventors: Kaleen Konrad Childers, Medfield, MA (US); J. Michael Ellis, Milton, MA (US); Peter J. Fuller, Ashland, MA (US); Hakan Gunaydin, Belmont, MA (US); Jack D. Scott, Scotch Plains, NJ (US); Haiqun Tang, Belle Mead, NJ (US); Charles S. Yeung, Dedham, MA (US)

(73) Assignee: Merck Sharp & Dohme LLC, Rahway, NJ (US)

( * ) Notice: Subject to any disclaimer, the term of this patent is extended or adjusted under 35 U.S.C. 154(b) by 448 days.

(21) Appl. No.: 18/549,223

(22) PCT Filed: Mar. 14, 2022

(86) PCT No.: PCT/US2022/020110
§ 371 (c)(1),
(2) Date: Sep. 6, 2023

(87) PCT Pub. No.: WO2022/197577
PCT Pub. Date: Sep. 22, 2022

(65) Prior Publication Data

US 2024/0174679 A1 May 30, 2024

Related U.S. Application Data

(60) Provisional application No. 63/162,307, filed on Mar. 17, 2021.

(51) Int. Cl.

| | |
|---|---|
| ***C07D 487/04*** | (2006.01) |
| ***A61K 31/4155*** | (2006.01) |
| ***A61K 31/422*** | (2006.01) |
| ***A61K 31/427*** | (2006.01) |
| ***A61K 31/437*** | (2006.01) |
| ***A61K 31/4439*** | (2006.01) |
| ***A61K 31/496*** | (2006.01) |
| ***A61K 31/506*** | (2006.01) |
| ***A61K 31/5365*** | (2006.01) |
| ***A61K 31/5377*** | (2006.01) |
| ***A61K 31/55*** | (2006.01) |

(Continued)

(52) U.S. Cl.
CPC ........ *C07D 487/04* (2013.01); *A61K 31/4155* (2013.01); *A61K 31/422* (2013.01); *A61K 31/427* (2013.01); *A61K 31/437* (2013.01); *A61K 31/4439* (2013.01); *A61K 31/496* (2013.01); *A61K 31/506* (2013.01); *A61K 31/5365* (2013.01); *A61K 31/5377* (2013.01); *A61K 31/55* (2013.01); *C07D 401/12* (2013.01); *C07D 401/14* (2013.01); *C07D 403/12* (2013.01); *C07D 403/14* (2013.01); *C07D 413/12* (2013.01); *C07D 413/14* (2013.01); *C07D 417/12* (2013.01); *C07D 417/14* (2013.01); *C07D 471/04* (2013.01); *C07D 498/04* (2013.01)

(58) Field of Classification Search
CPC .................................................... C07D 487/04
See application file for complete search history.

(56) References Cited

U.S. PATENT DOCUMENTS 4,166,452 A 9/1979 Generales, Jr.
4,256,108 A 3/1981 Theeuwes
(Continued)

FOREIGN PATENT DOCUMENTS

WO 2007149798 A2 12/2007
WO 2009074234 A1 6/2009
(Continued)

OTHER PUBLICATIONS

American Chemical Society. Chemical Abstract Service. RN 518988-57-3. Entered into STN: May 22, 2003. (Year: 2003).*
(Continued)

*Primary Examiner* — John S Kenyon
(74) *Attorney, Agent, or Firm* — Sylvia A. Ayler; Catherine Fitch

(57) ABSTRACT

The present invention is directed to certain (hetero)aroyl 4-aminopyrazole derivatives of Formula (I) and pharmaceutically acceptable salts thereof, wherein A, $R^1$, $R^2$, and $R^3$ are as defined herein, which are potent inhibitors of LRRK2 kinase and may be useful in the treatment or prevention of diseases in which the LRRK2 kinase is involved, such as Parkinson's Disease and other diseases and disorders described herein. The invention is also directed to pharmaceutical compositions comprising these compounds and the use of these compounds and compositions in the prevention or treatment of such diseases in which LRRK-2 kinase is involved.

(I)

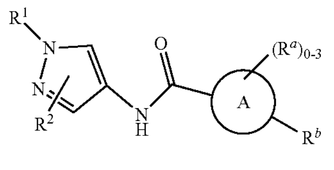

18 Claims, No Drawings

(51) Int. Cl.

| | |
|---|---|
| ***C07D 401/12*** | (2006.01) |
| ***C07D 401/14*** | (2006.01) |
| ***C07D 403/12*** | (2006.01) |
| ***C07D 403/14*** | (2006.01) |
| ***C07D 413/12*** | (2006.01) |
| ***C07D 413/14*** | (2006.01) |
| ***C07D 417/12*** | (2006.01) |
| ***C07D 417/14*** | (2006.01) |
| ***C07D 471/04*** | (2006.01) |
| ***C07D 498/04*** | (2006.01) |

(56) References Cited

U.S. PATENT DOCUMENTS

| | | | |
|---|---|---|---|
| 4,265,874 | A | 5/1981 | Bonsen et al. |
| 7,897,626 | B2 | 3/2011 | Bothe |
| 2011/0281841 | A1 | 11/2011 | Lee et al. |
| 2012/0157427 | A1 | 6/2012 | Baker-Glenn et al. |
| 2017/0022168 | A1 | 1/2017 | Greul |

FOREIGN PATENT DOCUMENTS

| | | | |
|---|---|---|---|
| WO | 2011087776 | A1 | 7/2011 |
| WO | 2011106114 | A1 | 9/2011 |
| WO | 2011124580 | A1 | 10/2011 |
| WO | 2012052459 | A1 | 4/2012 |
| WO | 2012062783 | A1 | 5/2012 |
| WO | 2016036586 | A1 | 3/2016 |
| WO | 2016172560 | A1 | 10/2016 |
| WO | 2020212697 | A1 | 10/2020 |

OTHER PUBLICATIONS

American Chemical Society. Chemical Abstract Service. RN 1315544-91-2. Entered into STN: Aug. 9, 2011. (Year: 2011).*

American Chemical Society. Chemical Abstract Service. RN 1352200-93-1. Entered into STN: Jan. 3, 2012 (Year: 2012).*

American Chemical Society. Chemical Abstract Service. RN 2033071-05-3. Entered into STN: Nov. 16, 2016. (Year: 2016).*

American Chemical Society. Chemical Abstract Service. RN 2507825-09-2. Entered into STN: Nov. 9, 2020 (Year: 2020).*

American Chemical Society. Chemical Abstract Service. RN 825618-61-9. Entered into STN: Feb. 4, 2005. (Year: 2005).*

American Chemical Society. Chemical Abstract Service. RN 1160288-82-3. Entered into STN: Jun. 29, 2009. (Year: 2009).*

Aasly, J.O. et al., Clinical Features of LRRK2-Associated Parkinson's Disease in Central Norway, Ann Neurol, 2005, 762-765, 57(5).

Adams, J.R. et al., PET in LRRK2 mutations: comparison to sporadic Parkinson's disease and evidence for presymptomatic compensation, Brain, 2005, 2777-2785, 128.

Agalliu, I. et al., Higher Frequency of Certain Cancers in LRRK2 G2019S Mutation Carriers With Parkinson Disease, JAMA Neurology, 2015, 58-65, 72(1).

Bailey, R.M. et al., LRRK2 phosphorylates novel tau epitopes and promotes tauopathy, Acta Neuropathol, 2013, 809-827, 126.

Bingham, A.L., et al.,, "Over One Hundred Solvates of sulfathiazole", Chem. Commun., 2001, pp. 603-604.

Caira, M.R., et al.,, "Preparation and Crystal Characterization of a Polymorph, a Monohydrate, and an Ethyl Acetate Solvate of the Antifungal Fluconazole", J. Pharmaceutical Sci., 2004, pp. 601-611, vol. 93, No. 3.

Daher, J.P. et al., Leucine-rich Repeat Kinase 2 (LRRK2) Pharmacological Inhibition Abates alpha-Synuclein Gene-induced Neurodegeneration, The Journal of Biological Chemistry, 2015, 19433-19444, 290(32).

Daiss, Jurgen, O. et al., Sila-venlafaxine, a Sila-Analogue of the Serotonin/Noradrenaline Reuptake Inhibitor Venlafaxine: Synthesis, Crystal Structure Analysis, and Pharmacological Characterization, Organometallics, 2006, pp. 1188-1198, vol. 25.

Danoy, P. et al., Association of Variants at 1q32 and STAT3 with Ankylosing Spondylitis Suggests Genetic Overlap with Crohn's Disease, PLoS Genetics, 2010, 1-5, 6(12):e1001195.

Engel, P. et al., Therapeutic Targeting of B Cells for Rheumatic Autoimmune Diseases, Pharmacological Reviews, 2011, 127-156, 63(1).

Gilks, W.P. et al., A common LRRK2 mutation in idiopathic Parkinson's disease, Lancet, 2005, 415-416, 365.

Goedert, M. et al., Mutations causing neurodegenerative tauopathies, Biochimica et Biophysica Acta, 2005, 240-250, 1739.

Guo, L. et al., The Parkinson's disease-associated protein, leucine-rich repeat kinase 2 (LRRK2), is an authentic GTPase that stimulates kinase activity, Experimental Cell Research, 2007, 3658-3670, 313.

Kawakami, F. et al., LRRK2 Phosphorylates Tubulin-Associated Tau but Not the Free Molecule: LRRK2-Mediated Regulation of the Tau-Tubulin Association and Neurite Outgrowth, PLoS ONE, 2012, 1-9, 7(1):e30834.

Kumari, U. et al., LRRK2 in Parkinson's disease: genetic and clinical studies from patients, The FEBS Journal, 2009, 6455-6463, 276.

Lee, B.D. et al., Inhibitors of leucine-rich repeat kinase-2 protect against models of Parkinson's disease, Nature Medicine, 2010, 998-1000, 16.

Li, Y. et al., Mutant LRRK2R1441G BAC transgenic mice recapitulate cardinal features of Parkinson's disease, Nature Neuroscience, 2009, 826-828, 12(7).

Looyenda, B.D. et al., Chromosomal amplification of leucine-rich repeat kinase-2 (LRRK2) is required for oncogenic MET signaling in papillary renal and thyroid carcinomas, Proc Natl Acad Sci USA, 2011, 1439-1444, 108(4).

Moehle, M.S. et al., LRRK2 Inhibition Attenuates Microglial Inflammatory Responses, The Journal of Neuroscience, 2012, 1602-1611, 32(5).

Nichols, W. C. et al., Genetic screening for a single common LRRK2 mutation in familial Parkinson's disease, Lancet, 2005, 410-412, 365.

Pubchem, SID 398053452, Available Date: Dec. 6, 2019 [retrieved on Apr. 18, 2022]. Retrieved from the Internet: URL: https://pubchem.ncbi.nlm.nih.gov/substance/398053452 entire document (5 pages).

Saunders-Pullman, R. et al., LRRK2 G2019S Mutations are Associated with an Increased Cancer Risk in Parkinson Disease, Movement Disorders, 2010, 2536-22541, 25(15).

Showell, Graham, A. et al., (R)-Sila-venlafaxine: A selective noradrenaline reuptake inhibitor for the treatment of emesis, Bioorganic & Medicinal Chemistry Letters, 2006, pp. 2555-2558, vol. 16.

Shtilbans, A. et al., Differential gene expression in patients with amyotrophic lateral sclerosis, Amyotrophic Lateral Sclerosis, 2011, 250-256, 12(4).

Umeno, J. et al., Meta-analysis of Published Studies Identified Eight Additional Common Susceptibility Loci for Crohn's Disease and Ulcerative Colitis, Inflammatory Bowel Disease, 2011, 2407-2415, 17(12).

Van Tonder, E.C., et al.,, "Preparation and Physicochemical Characterization of 5 Niclosamide Solvates and 1 Hemisolvate", AAPS Pharm Sci Tech, 2004, pp. 1-10, vol. 5, No. 1, Article 12, US.

Volpicelli-Daley, L.A. et al., G2019S-LRRK2 Expression Augments alpha-Synuclein Sequestration into Inclusions in Neurons, The Journal of Neuroscience, 2016, 7415-7427, 36(28).

Zhang, Fu-Ren et al., Genomewide Association Study of Leprosy, The New England Journal of Medicine, 2009, 2609-2618, 361.

Zhao, Yi et al., LRRK2 variant associated with Alzheimer's disease, Neurobiology of Aging, 2011, 1990-1993, 32.

Zhu, X. et al., LRRK2 in Parkinson's disease and dementia with Lewy bodies, Molecular Neurodegeneration, 2006, 1-9, 1:17.

Zimprich, A. et al., Mutations in LRRK2 Cause Autosomal-Dominant Parkinsonism with Pleomorphic Pathology, Neuron, 2004, 601-607, 44(4).

Gibson, Tony S. et al., Structure-based drug design of novel ASK1 inhibitors using an integrated lead optimization strategy, Bioorganic & Medicinal Chemistry Letters, 27, 1709-1713, 2017.

* cited by examiner

HETEROAROYL AMIDES AS LRRK2 INHIBITORS, PHARMACEUTICAL COMPOSITIONS, AND USES THEREOF

CROSS REFERENCE TO RELATED APPLICATIONS

This application is a U.S. National Phase application under 35 U.S.C. § 371 of PCT Application No. PCT/US2022/020110 filed Mar. 14, 2022, which claims priority from U.S. 63/162,307, filed Mar. 17, 2021.

BACKGROUND OF THE INVENTION

Parkinson's disease (PD) is a common neurodegenerative disease caused by progressive loss of mid-brain dopaminergic neurons leading to abnormal motor symptoms such as bradykinesia, rigidity and resting tremor. Many PD patients also experience a variety of non-motor symptoms including cognitive dysfunction, autonomic dysfunction, emotional changes and sleep disruption. The combined motor and non-motor symptoms of Parkinson's disease severely impact patient quality of life.

While the majority of PD cases are idiopathic, there are several genetic determinants such as mutations in SNCA, Parkin, PINK1, DJ-1 and LRRK2. Linkage analysis studies have demonstrated that multiple missense mutations in the Leucine-Rich Repeat Kinase 2 (LRRK2) gene lead to an autosomal late onset form of PD. LRRK2 is a 286 kDa cytoplasmic protein containing kinase and GTPase domains as well as multiple protein-protein interaction domains. See for example, Aasly et al., Annals of Neurology, Vol. 57(5), May 2005, pp. 762-765; Adams et al., Brain, Vol. 128, 2005, pp. 2777-85; Gilks et al., Lancet, Vol. 365, Jan. 29, 2005, pp. 415-416, Nichols et al., Lancet, Vol. 365, Jan. 29, 2005, pp. 410-412, and U. Kumari and E. Tan, FEBS journal 276 (2009) pp. 6455-6463.

In vitro biochemical studies have demonstrated that LRRK2 proteins harboring the PD associated proteins generally confer increased kinase activity and decreased GTP hydrolysis compared to the wild type protein (Guo et al., Experimental Cell Research, Vol, 313, 2007, pp. 3658-3670) thereby suggesting that small molecule LRRK2 kinase inhibitors may be able to block aberrant LRRK2-dependent signaling in PD. In support of this notion, it has been reported that inhibitors of LRRK2 are protective in models of PD (Lee et al., Nature Medicine, Vol 16, 2010, pp. 998-1000).

LRRK2 expression is highest in the same brain regions that are affected by PD. LRRK2 is found in Lewy bodies, a pathological hallmark of PD as well as other neurodegenerative diseases such as Lewy body dementia (Zhu et al., Molecular Neurodegeneration, Vol 30, 2006, pp. 1-17).

Further, LRRK2 mRNA levels are increased in the striatum of MPTP-treated marmosets, an experimental model of Parkinson's disease, and the level of increased mRNA correlates with the level of L-Dopa induced dyskinesia suggesting that inhibition of LRRK2 kinase activity may have utility in ameliorating L-Dopa induced dyskinesias. These and other recent studies indicate that a potent, selective and brain penetrant LRRK2 kinase inhibitor could be a therapeutic treatment for PD. (Lee et al., Nat. Med. 2010 September; 16(9):998-1000; Zhu, et al., Mol. Neurodegeneration 2006 Nov. 30; 1:17; Daher, et al., J Biol Chem. 2015 Aug. 7; 290(32):19433-44; Volpicelli-Daley et al., J Neurosci. 2016 Jul. 13; 36(28):7415-27).

LRRK2 mutations have been associated with Alzheimer's-like pathology (Zimprach et al., Neuron. 2004 Nov. 18; 44(4):601-7) and the LRRK2 R1628P variant has been associated with an increased risk of developing AD (Zhao et al., Neurobiol Aging. 2011 November; 32(11):1990-3). Mutations in LRRK2 have also been identified that are clinically associated with the transition from mild cognitive impairment to Alzheimer's disease (see WO2007149798). Together these data suggest that LRRK2 inhibitors may be useful in the treatment of Alzheimer's disease and other dementias and related neurodegenerative disorders.

LRRK2 has been reported to phosphorylate tubulin-associated tau and this phosphorylation is enhanced by the kinase activating LRRK2 mutation G2019S (Kawakami et al., PLoS One. 2012; 7(1):e30834; Bailey et al., Acta Neuropathol. 2013 December; 126(6):809-27). Additionally, over expression of LRRK2 in a tau transgenic mouse model resulted in the aggregation of insoluble tau and its phosphorylation at multiple epitopes (Bailey et al., 2013). Hyperphosphorylation of tau has also been observed in LRRK2 R1441G overexpressing transgenic mice (Li et al., Nat Neurosci. 2009 July; 12(7):826-8). Inhibition of LRRK2 kinase activity may therefore be useful in the treatment of tauopathy disorders characterized by hyperphosphorylated of tau such as argyrophilic grain disease, Picks disease, corticobasal degeneration, progressive supranuclear palsy, inherited frontotemporal dementia and parkinson's linked to chromosome 17 (Goedert and Jakes Biochim Biophys Acta. 2005 Jan. 3).

A growing body of evidence suggests a role for LRRK2 in immune cell function in the brain with LRRK2 inhibitors demonstrated to attenuate microglial inflammatory responses (Moehle et al., J Neurosci. 2012 Feb. 1; 32(5):1602-11). As neuroinflammation is a hallmark of a number of neurodegenerative diseases such PD, AD, MS, HIV-induced dementia, ALS, ischemic stroke, MS, traumatic brain injury and spinal cord injury, LRRK2 kinases inhibitors may have utility in the treatment of neuroinflammation in these disorders. Significantly elevated levels of LRRK2 mRNA have been observed in muscle biopsy samples taken from patients with ALS (Shtilbans et al., Amyotroph Lateral Scler. 2011 July; 12(4):250-6). LRRK2 inhibitors have been disclosed in the art, e.g., WO2016036586.

LRRK2 is also expressed in cells of the immune system and recent reports suggest that LRRK2 may play a role in the regulation of the immune system and modulation of inflammatory responses. LRRK2 kinase inhibitors may therefore be of utility in a number of diseases of the immune system such as lymphomas, leukemias, multiple sclerosis rheumatoid arthritis, systemic lupus erythematosus autoimmune hemolytic anemia, pure red cell aplasia, idiopathic thrombocytopenic pupura (ITP), Evans Syndrome, vasculitis, bullous skin disorder, type I diabetes mellitus, Sjorgen's syndrome, Delvic's disease, inflammatory myopathies (Engel at al., Pharmacol Rev. 2011 March; 63(1):127-56; Homam et al., Homam et al., Clin Neuromuscluar disease, 2010) and ankylosing spondylitis (Danoy et al., PLoS Genet. 2010 Dec. 2; 6(12)). Increased incidence of certain types of non-skin cancers such as renal, breast, lung, prostate, and acute myelogenous leukemia (AML) have been reported in patients with the LRRK2 G2019S mutation (Agalliu et al., JAMA Neurol. 2015 January; 72(1); Saunders-Pullman et al., Mov Disord. 2010 Nov. 15; 25(15):2536-41). LRRK2 has amplification and overexpression has been reported in papillary renal and thyroid carcinomas. Inhibiting LRRK2 kinase activity may therefore be useful in the treatment of cancer (Looyenga et al., Proc Natl Acad Sci USA. 2011 Jan. 25; 108(4):1439-44).

Genome-wide association studies also highlight LRRK2 in the modification of susceptibility to the chronic autoimmune Crohn's disease and leprosy (Zhang et al., The New England Journal of Medicine, Vol 361, 2009, pp. 2609-2618; Umeno et al., Inflammatory Bowel Disease Vol 17, 2011, pp. 2407-2415).

SUMMARY OF THE INVENTION

The present invention is directed to certain heteroaroyl derivatives, which are collectively or individually referred to herein as "compound(s) of the invention" or "compounds of Formula (I)", as described herein. The present invention is further directed to certain heteroaroyl 4-aminopyrazole derivatives of Formula (I). Surprisingly and advantageously, the compounds of Formula (I), each of which possess four linked nitrogen containing cyclic groups, one of which is linked through an amide moiety, exhibit excellent LRRK2 inhibitory activity. In some embodiments, the compounds of the invention exhibit unexpectedly superior potency as inhibitors of LRRK2 kinase, as evidenced by the data reported herein. The compounds of the invention may be useful in the treatment or prevention of diseases (or one or more symptoms associated with such diseases) in which the LRRK2 kinase is involved, including Parkinson's disease and other indications, diseases and disorders as described herein. The invention is also directed to pharmaceutical compositions comprising a compound of the invention and to methods for the use of such compounds and compositions for the treatments described herein.

DETAILED DESCRIPTION OF THE INVENTION

For each of the following embodiments, any variable not explicitly defined in the embodiment is as defined in Formula (I). In each of the embodiments described herein, each variable is selected independently of the other unless otherwise noted.

In one embodiment, the compounds of the invention have the structural Formula (I):

I

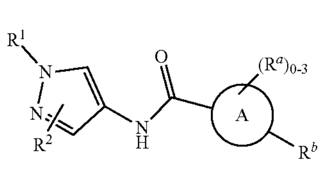

or a pharmaceutically acceptable salt thereof, wherein:

A is a heteroaryl or aryl selected from the group consisting of thiazolyl, pyrazolyl, pyridyl, phenyl, pyrimidinyl, oxazolyl and pyrazinyl;

$R^1$ is selected from hydrogen, $C_{1-6}$ alkyl, —$(CH_2)_nOC_{1-6}$ alkyl, —$(CH_2)_n$halogen, —$(CH_2)CN$, $C_{1-6}$ haloalkyl, —$CH(R)_2$, —$(CH_2)_nC_{3-6}$cycloalkyl, —$(CH_2)_n C_{6-10}$aryl, —$(CH_2)_nC_{5-10}$heteroaryl, —$(CH_2)_nC_{4-10}$ heterocyclyl, and —$(CH_2)_nN(R)_2$, said alkyl and cycloalkyl, aryl, heteroaryl, and heterocyclyl optionally substituted with 1 to 3 groups selected from $R^x$;

R is selected from hydrogen, $C_{1-6}$ alkyl, cyclopropyl, CN, $NHCH(CH_3)_2$, and phenyl, said phenyl optionally substituted with 1 to 3 groups of $R^x$;

$R^2$ is selected from hydrogen, $C_{1-6}$ alkyl, —$OC_{1-6}$ alkyl, halogen, $C(O)C_{1-6}$alkyl, $C(O)N(R)_2$, —$C(O)OC_{1-6}$alkyl, CN, $C_{1-6}$haloalkyl, —$C_{3-6}$cycloalkyl, $(O)_{0-1}C_{6-10}$aryl, $C_{5-10}$heteroaryl, and —$(CH_2)_nN(R)_2$, said alkyl and cycloalkyl, aryl, and heteroaryl optionally substituted with 1 to 3 groups selected from $R^x$;

$R^a$ is selected from $C_{1-6}$ alkyl, CN and halogen;

$R^b$ are independently selected from $C_{1-6}$ alkyl, —$OC_{1-6}$ alkyl, $C_{3-6}$ cycloalkyl, —$SC_{1-6}$alkyl, $C_{6-10}$aryl, $C_{5-10}$heteroaryl, $C_{3-10}$heterocyclyl, $NHC(O)C_{1-6}$alkyl, $N(R)_2$, and —$NHC_{6-10}$aryl, said alkyl, aryl, heteroaryl, and heterocyclyl optionally substituted with 1 to 3 groups of $R^y$;

$R^x$ is selected from $C_{1-6}$ alkyl, —$OC_{1-6}$ alkyl, OH, $C_{3-6}$ cycloalkyl —$CH_2SC_{1-6}$ alkyl, —$OCH_2OC_{1-6}$ alkyl, halogen, —$SO_2CH_3$, CN, and $(CH_2)_nN(R)_2$, $R^y$ is selected from hydrogen, $C_{1-6}$ alkyl, —$(CH_2)_nOC_{1-6}$ alkyl, $C_{3-6}$cycloalkyl, $C_{1-6}$ haloalkyl, -halogen, CN, $(CH_2)_nC_{4-10}$heterocyclyl, —$(CH_2)_n$ $_{5-10}$heteroaryl, and —$SO_2C_{1-6}$ alkyl; and n is selected from 0 to 3.

An embodiment of this invention is realized when A is linked via a carbon atom to the carbonyl portion of Formula (I).

An embodiment of this invention is realized when A is a heteroaryl that is pyridyl. An embodiment of this invention is realized when A an aryl that is phenyl. An embodiment of this invention is realized when A is a heteroaryl that is pyrimidinyl. An embodiment of this invention is realized when A is a heteroaryl that is pyrazolyl. An embodiment of this invention is realized when A is a heteroaryl that is thiazolyl. An embodiment of this invention is realized when A is a heteroaryl that is oxazolyl. An embodiment of this invention is realized when A is a heteroaryl that is pyrazinyl.

Another embodiment of this invention is realized when $R^1$ is selected from $C_{1-6}$ alkyl, and $C_{1-6}$ haloalkyl, said alkyl unsubstituted or substituted with 1 to 3 groups of $R^x$. A subembodiment of this aspect of the invention is realized when $R^1$ is $C_{1-6}$ alkyl, unsubstituted or substituted with 1 to 3 groups of $R^x$. Another subembodiment of this aspect of the invention is realized when $R^1$ is $C_{1-6}$ haloalkyl, said alkyl unsubstituted or substituted with 1 to 3 groups of $R^x$. Another subembodiment of this invention is realized when $R^1$ is selected from the group consisting of $CH_3$, $CH(CH_3)_2$, $CH_2CH(CH_3)_2$, $CH_2CH_3$, $C(CH_3)_3$, $(CH_2)_nCN$, $CH(CH_3)CN$, $CH_2CF_3$, $CHF_2$, $CH_2OH$, $CH_2CHF_2$, $(CH_2)_nOCH_3$, and $(CH_2)_nF$. Another subembodiment of this aspect of the invention is realized when $R^1$ is $CH_3$, $C(CH_3)_3$, $CH(CH_3)_2$, and $CH_2CH_3$.

Another embodiment of this invention is realized when $R^1$ is —$(CH_2)_nC_{3-6}$cycloalkyl, said cycloalkyl unsubstituted or substituted with 1 to 3 groups of $R^x$. A subembodiment of this aspect of the invention is realized when —$(CH_2)_nC_{3-6}$cycloalkyl is selected from the group consisting of —$(CH_2)_n$cyclopropyl, —$(CH_2)_n$cyclobutyl, —$(CH_2)_n$cyclopentyl and —$(CH_2)_n$cyclohexyl, said group unsubstituted or substituted with 1 to 3 groups of $R^x$. Another subembodiment of this aspect of the invention is realized when $R^1$ is unsubstituted or substituted —$(CH_2)_n$cyclopropyl. Another subembodiment of this aspect of the invention is realized when $R^1$ is unsubstituted or substituted —$(CH_2)_n$cyclobutyl. Another subembodiment of this aspect of the invention is realized when $R^1$ is unsubstituted or substituted —$(CH_2)_n$cyclopentyl. Another subembodiment of this aspect of the invention is realized when $R^1$ is unsubstituted or substituted —$(CH_2)_n$cyclohexyl. A further subembodiment of this aspect of the invention is realized when $R^1$ is cyclopropyl, cyclobutyl, $CH_2$-cyclopropyl, CH(cyclopropyl)$_2$, $CH_2$-cyclobutyl, $CH_2$-cyclohexyl, unsubstituted or substituted with fluoro, —CN, —$CH_2NH_2$, -cyclopropyl, isopropyl, or $CH_2CH(CH_3)CH(CH_3)_3$.

Another embodiment of this invention is realized when $R^1$ is —$(CH_2)_nC_{6-10}$aryl, said aryl unsubstituted or substituted with 1 to 3 groups of $R^x$. A subembodiment of this aspect of the invention is realized when —$(CH_2)_nC_{6-10}$aryl is selected from $(CH_2)_n$phenyl and $(CH_2)_n$napthyl, said phenyl and napthyl unsubstituted or substituted with 1 to 3 groups of $R^x$. A subembodiment of this aspect of the invention is realized when —$(CH_2)_nC_{6-10}$aryl is $(CH_2)_n$phenyl. A further subembodiment of this aspect of the invention is realized when —$(CH_2)_nC_{6-10}$aryl is phenyl, benzyl, or 4-fluorobenzyl.

Another embodiment of this invention is realized when $R^1$ is —$(CH_2)_nC_{5-10}$heteroaryl, said heteroaryl unsubstituted or substituted with 1 to 3 groups of R. A subembodiment of this aspect of the invention is realized when —$(CH_2)_nC_{5-10}$heteraryl is $(CH_2)_n$pyridyl $(CH_2)_n$pyrrolyl, $(CH_2)_n$imidazolyl, $(CH_2)_n$triazoloazepinyl, $(CH_2)_n$tetrahydrotriazoloazepinyl, or $(CH_2)_n$tetrahydrotriazolyl unsubstituted or substituted with 1 to 3 groups of $R^x$.

Another embodiment of this invention is realized when $R^1$ is —$(CH_2)_nC_{4-10}$heterocyclyl, said aryl unsubstituted or substituted with 1 to 3 groups of $R^x$. A subembodiment of this aspect of the invention is realized when —$(CH_2)_nC_{4-10}$heterocyclyl is selected from $(CH_2)_n$oxetanyl, $(CH_2)_n$piperidinyl, $(CH_2)_n$tetrahydropyranyl, $(CH_2)_n$tetrahydrofuranyl, $(CH_2)_n$piperazinyl, $(CH_2)_n$morpholinyl, $(CH_2)_n$azabicyclooctanyl, and $(CH_2)_n$pyrrolidinyl, said oxetanyl, piperidinyl, tetrahydropyranyl, tetrahydrofuranyl, piperazinyl, morpholinyl, azabicyclooctanyl, or pyrrolyl, unsubstituted or substituted with 1 to 3 groups of $R^x$. A subembodiment of this aspect of the invention is realized when —$(CH_2)_nC_{4-10}$heterocyclyl is tetrahydrotriazoloazepinyl. Another subembodiment of this aspect of the invention is realized when —$(CH_2)_nC_{4-10}$heterocyclyl is $(CH_2)_n$oxetanyl. Another subembodiment of this aspect of the invention is realized when —$(CH_2)_nC_{4-10}$heterocyclyl is $(CH_2)_n$piperidinyl. Another subembodiment of this aspect of the invention is realized when —$(CH_2)_nC_{4-10}$heterocyclyl is $(CH_2)_n$tetrahydropyranyl. Another subembodiment of this aspect of the invention is realized when —$(CH_2)_nC_{4-10}$heterocyclyl is $(CH_2)_n$tetrahydrofuranyl. Another subembodiment of this aspect of the invention is realized when —$(CH_2)_nC_{4-10}$heterocyclyl is $(CH_2)_n$piperazinyl. Another subembodiment of this aspect of the invention is realized when —$(CH_2)_nC_{4-10}$heterocyclyl is $(CH_2)_n$pyrrolidinyl. Still another subembodiment of this aspect of the invention is realized when the —$(CH_2)_nC_{4-10}$heterocyclyl is selected from $CH_2$-morpholinyl, $CH_2CH_2$-morpholinyl, $CH_2$azabicyclo[3.2.1]octan-8-yl, $CH_2$-oxetanyl, $CH_2CH_2$-oxetanyl, $CH_2$-piperazinyl, $CH_2CH_2CH_2$-piperazinyl, $CH_2CH_2$-piperazinyl, $CH_2CH_2$-tetrahydropyranyl, $CH_2$-tetrahydropyranyl, $CH_2CH_2$-piperadinyl, $CH_2$-piperidinyl, $CH_2$-pyrrolidinyl, and $CH_2CH_2$-pyrrolidinyl.

Another embodiment of this invention is realized when $R^1$ is —$(CH_2)_nN(R)_2$. A subembodiment of this aspect of the invention is realized when $R^1$ is $(CH_2)_nN(CH_3)_3$. In a particular subembodiment of this aspect, $R^1$ is $CH_2CH_2CH_2$—$N(CH_3)_2$.

Another embodiment of this invention is realized when $R^2$ is hydrogen.

Another embodiment of this invention is realized when $R^2$ is $C_{1-6}$ alkyl, —$OC_{1-6}$ alkyl, $C_{1-6}$ haloalkyl, said alkyl unsubstituted or substituted with 1 to 3 groups selected from $R^x$. A subembodiment of this aspect of the invention is realized when the $C_{1-6}$ alkyl, or —$OC_{1-6}$ alkyl is selected from $CH_3$, $OCH_2CF_3$, $OCH_3$, $CHF_2$, $OCH(CH_3)_2$, $OCH_2CHF_2$, $CHF_2$, and $CF_3$.

Another embodiment of this invention is realized when $R^2$ is $C(O)C_{1-6}$alkyl, $C(O)N(R)_2$, or $C(O)OC_{1-6}$alkyl, selected from the group consisting of $C(O)NHCH_3$, $C(O)N(CH_3)_2$, $C(O)NH_2$, and $C(O)OCH_3$.

Another embodiment of this invention is realized when $R^2$ is —$C_{3-6}$cycloalkyl unsubstituted or substituted with 1 to 3 groups selected from $R^x$. A subembodiment of this aspect of the invention is realized when $R^2$ is selected from the group consisting of cyclopropyl, cyclobutyl, cyclopentyl, and cyclohexyl, said group unsubstituted or substituted with 1 to 3 groups selected from $R^x$. Another subembodiment of this aspect of the invention is realized when $R^2$ is cyclopropyl.

Another embodiment of this invention is realized when $R^2$ is $(O)_{0-1}C_{6-10}$aryl unsubstituted or substituted with 1 to 3 groups selected from $R^x$. A subembodiment of this aspect of the invention is realized when $(O)_{0-1}C_{6-10}$aryl is selected from phenyl or —O-phenyl, said phenyl and —O-phenyl unsubstituted or substituted with 1 to 3 groups from $R^x$.

Another embodiment of this invention is realized when $R^2$ is $C_{5-10}$heteroaryl unsubstituted or substituted with 1 to 3 groups selected from $R^x$. A subembodiment of this aspect of the invention is realized when $C_{5-10}$heteroaryl is pyridyl, tetrahydrotriazopyridyl, or pyrazolyl, each unsubstituted or substituted with 1 to 3 groups from $R^x$.

Another embodiment of this invention is realized when $R^2$ is CN $C(O)N(R)_2$, or —$(CH_2)_nN(R)_2$ wherein $C(O)N(R)_2$, and —$(CH_2)_nN(R)_2$ are selected from $C(O)NH_2$, $C(O)NHCH_3$, and $C(O)N(CH_3)_2$.

Another embodiment of this invention is realized when $R^b$ is $C_{1-6}$alkyl, said alkyl unsubstituted or substituted with 1 to 3 groups from $R^y$.

Another embodiment of this invention is realized when $R^b$ is $C_{3-6}$ cycloalkyl, selected from cyclopropyl and cyclobutyl, unsubstituted or substituted with 1 to 3 groups from $R^y$.

Another embodiment of this invention is realized when $R^b$ is —$SC_{1-6}$alkyl such as $SCH_3$.

Another embodiment of this invention is realized when $R^b$ is $C_{6-10}$aryl or —$NHC_{6-10}$aryl, wherein the aryl is phenyl, unsubstituted or substituted with 1 to 3 groups of $R^y$.

Another embodiment of this invention is realized when $R^b$ is $C_{5-10}$heteroaryl, selected from the group consisting of pyridyl, pyrimidinyl, pyrazolyl, furanyl, imidazolyl, thiazolyl, isothiazolyl, pyrrolyl, and oxazinylthiazolyl, pyridazinyl, benzothiophenyl, said group unsubstituted or substituted with 1 to 3 groups of $R^y$. A subembodiment of this aspect of the invention is realized when $R^b$ is pyridyl, unsubstituted or substituted with 1 to 3 groups of $R^y$. A subembodiment of this aspect of the invention is realized when $R^b$ is pyrimidinyl, unsubstituted or substituted with 1 to 3 groups of $R^y$. A subembodiment of this aspect of the invention is realized when $R^b$ is pyrazolyl, unsubstituted or substituted with 1 to 3 groups of $R^y$. A subembodiment of this aspect of the invention is realized when $R^b$ is imidazolyl, unsubstituted or substituted with 1 to 3 groups of $R^y$. A subembodiment of this aspect of the invention is realized when $R^b$ is thiazolyl, unsubstituted or substituted with 1 to 3 groups of $R^y$. A subembodiment of this aspect of the invention is realized when $R^b$ is isothiazolyl, unsubstituted or substituted with 1 to 3 groups of $R^y$. A subembodiment of this aspect of the invention is realized when $R^b$ is pyrrolyl, unsubstituted or substituted with 1 to 3 groups of $R^y$. A subembodiment of this aspect of the invention is realized when $R^b$ is benzothiophenyl, unsubstituted or substituted with 1 to 3 groups from $R^y$. A subembodiment of this aspect of the invention is realized when $R^b$ is oxazinylthiazolyl, unsubstituted or substituted with 1 to 3 groups from $R^y$. A subembodiment of this aspect of the invention is realized when $R^b$ is pyridazinyl, unsubstituted or substituted with 1 to 3 groups from $R^y$. A subembodiment of this aspect of the invention is realized when $R^b$ is furanyl, unsubstituted or substituted with 1 to 3 groups from $R^y$.

Another embodiment of this invention is realized when $R^b$ is $C_{3-10}$heterocyclyl selected from the group consisting of pyrrolidinyl, piperidinyl, dihydropyrrolopyrazolyl, dihydropyrazolooxazinyl, and tetrahydropyrazolopyridinyl, said group unsubstituted or substituted with 1 to 3 groups selected from $R^y$. A subembodiment of this aspect of the invention is realized when $R^b$ is pyrrolidinyl, unsubstituted or substituted with 1 to 3 groups from $R^y$. A subembodiment of this aspect of the invention is realized when $R^b$ is piperidinyl, unsubstituted or substituted with 1 to 3 groups from $R^y$. A subembodiment of this aspect of the invention is realized when $R^b$ is dihydropyrrolopyrazolyl, unsubstituted or substituted with 1 to 3 groups from $R^y$. A subembodiment of this aspect of the invention is realized when $R^b$ is dihydropyrazolooxazinyl, unsubstituted or substituted with 1 to 3 groups from $R^y$. A subembodiment of this aspect of the invention is realized when $R^b$ is tetrahydropyrazolopyridinyl, unsubstituted or substituted with 1 to 3 groups from $R^y$.

Another embodiment of this invention is realized when $R^a$ is $CH_3$, isopropyl, CN, and F.

Another embodiment of this invention is realized when n is 0. Another embodiment of this invention is realized when n is 1. Still another embodiment of this invention is realized when n is 2. Yet another embodiment of this invention is realized when n is 3.

Yet another embodiment of this invention is realized when Formula I is represented by Formula II:

II

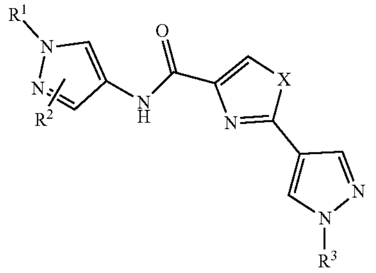

or a pharmaceutically acceptable salt thereof, wherein $R^1$ and $R^2$ are as described herein, X is S or O, and $R^3$ is selected from the group consisting of hydrogen, $C_{1-6}$ alkyl, $(CH_2)_nOC_{1-6}$ alkyl, $C_{1-6}$ haloalkyl, $(CH_2)_nC_{5-10}$ heteroaryl, halogen, CN, and $SO_2C_{1-6}$ alkyl, said alkyl and aryl unsubstituted or substituted with 1 to 3 groups from $R^x$.

An embodiment of the invention of Formula II is realized when X is S. Another embodiment of the invention of Formula II is realized when X is O.

An embodiment of the invention of Formula II is realized when $R^1$ is selected from hydrogen, $C_{1-6}$ alkyl, $-(CH_2)_nOC_{1-6}$ alkyl, $-(CH_2)_n$halogen, $-(CH_2)_nCN$, $C_{1-6}$ haloalkyl, $-CH(R)_2$, $-(CH_2)_nC_{3-6}$cycloalkyl, $-(CH_2)_nC_{6-10}$aryl, $-(CH_2)_nC_{5-10}$heteroaryl, $-(CH_2)_n C_{4-10}$heterocyclyl, and $-(CH_2)_nN(R)_2$, said alkyl and cycloalkyl, aryl, heteroaryl, and heterocyclyl optionally substituted with 1 to 3 groups selected from $R^x$. A subembodiment of Formula II is realized when $R^1$ is selected from the group consisting of $CH_3$, $CH(CH_3)_2$, $CH_2CH_3$, $C(CH_3)_3$, $(CH_2)_nCN$, $CH(CH_3)CN$, $CH_2CF_3$, $CHF_2$, $CH_2OH$, $CH_2CHF_2$, $(CH_2)_nOCH_3$, $CH(cyclopropyl)_2$ and $(CH_2)_nF$, $-(CH_2)_n$cyclopropyl, $-(CH_2)_n$cyclobutyl, $-(CH_2)_n$cyclopentyl and $-(CH_2)_n$cyclohexyl, $(CH_2)_n$phenyl and $(CH_2)_n$naphthyl, $(CH_2)_n$pyridyl or $(CH_2)_n$pyrrolyl, tetrahydrotriazoloazepinyl, $(CH_2)_n$oxetanyl, $(CH_2)_n$piperidinyl, $(CH_2)_n$tetrahydropyranyl, $(CH_2)_n$tetrahydrofuranyl, $(CH_2)_n$piperazinyl, and $(CH_2)_n$pyrrolidinyl, said group, unsubstituted or substituted with 1 to 3 groups of $R^x$, and $(CH_2)_nN(CH_3)_3$. Another subembodiment of Formula II is realized when $R^1$ is selected from $CH_3$, $CH_2CH_3$, $CH(CH_3)_2$, $-(CH_2)_n$cyclopropyl, $-(CH_2)_n$cyclobutyl, and $CH(cyclopropyl)_2$.

Another subembodiment of Formula II is realized when $R^2$ is hydrogen, $C_{1-6}$ alkyl, $-OC_{1-6}$ alkyl, halogen, $C(O)C_{1-6}$alkyl, $C(O)N(R)_2$, $-C(O)OC_{1-6}$alkyl, CN, $C_{1-6}$haloalkyl, $-C_{3-6}$cycloalkyl, $(O)_{0-1}C_{6-10}$aryl, $C_{5-10}$heteroaryl, and $-(CH_2)_nN(R)_2$, said alkyl and cycloalkyl, aryl, and heteroaryl optionally substituted with 1 to 3 groups selected from $R^x$. Another subembodiment of Formula II is realized when $R^2$ is hydrogen. Another subembodiment of Formula II is realized when $R^2$ is hydrogen, $CH_3$, $OCH_2CF_3$, $OCH_3$, $CHF_2$, $OCH(CH_3)_2$, $OCH_2CHF_2$, $CF_3$, $C(O)NHCH_3$, $C(O)N(CH_3)_2$, $C(O)NH_2$, and $C(O)OCH_3$, cyclopropyl, cyclobutyl, cyclopentyl, cyclohexyl, phenyl, —Ophenyl, pyridyl, tetrahydrotriazopyridyl, pyrazolyl, CN, $C(O)NH_2$, $C(O)NHCH_3$, and $C(O)N(CH_3)_2$. Another subembodiment of Formula II is realized when $R^2$ is selected from hydrogen, $CH_3$, cyclopropyl, $OCH_2CF_3$, $OCH_3$, $OCH(CH_3)_2$, $CHF_2$, $CF_3$, and $OCH_2CHF_2$.

Another embodiment of Formula II is realized when $R^3$ is selected from the group consisting of hydrogen, $C_{1-6}$ alkyl, $CH_2CF_3$, $CHF_2$, $(CH_2)_nOCH_3$, $CH_2$pyridyl, $CH_2$morpholinyl, halogen, CN, $SO_2CH_3$, said alkyl, pyridyl, and morpholinyl unsubstituted or substituted with 1 to 3 groups from $R^x$. A subembodiment of this aspect of the invention of Formula II is realized when $R^3$ is hydrogen. Another subembodiment of this aspect of the invention of Formula II is realized when $R^3$ is $C_{1-6}$ alkyl, said alkyl unsubstituted or substituted with 1 to 3 groups of R. Another subembodiment of this aspect of the invention of Formula II is realized when $R^3$ is selected from $CH_2CF_3$, $CHF_2$, and $(CH_2)_nOCH_3$. Another subembodiment of this aspect of the invention if Formula II is realized when $R^3$ is selected from $CH_2$pyridyl, $CH_2$morpholinyl, said pyridyl and morpholinyl unsubstituted or substituted with 1 to 3 groups of $R^x$.

An embodiment of the invention of Formula II is realized when X is S, $R^1$ is selected from the group consisting of hydrogen, $CH_3$, $CH(CH_3)_2$, $CH_2CH_3$, $C(CH_3)_3$, $(CH_2)_nCN$, $CH(CH_3)CN$, $CH_2CF_3$, $CHF_2$, $CH_2OH$, $CH_2CHF_2$, $(CH_2)_nOCH_3$, $CH(cyclopropyl)_2$ $(CH_2)_nF$, $(CH_2)_nN(CH_3)_3$, $-(CH_2)_n$cyclopropyl, $-(CH_2)_n$cyclobutyl, $-(CH_2)_n$cyclopentyl, $-(CH_2)_n$cyclohexyl, $(CH_2)_n$phenyl and $(CH_2)_n$naphthyl, $(CH_2)_n$pyridyl, $(CH_2)_n$pyrrolyl, tetrahydrotriazoloazepinyl, $(CH_2)_n$oxetanyl, $(CH_2)_n$piperidinyl, $(CH_2)_n$tetrahydropyranyl, $(CH_2)_n$tetrahydrofuranyl, $(CH_2)_n$piperazinyl, and $(CH_2)_n$pyrrolidinyl, said cyclopropyl, cyclobutyl, cyclopentyl, cyclohexyl, phenyl, naphthyl, pyridyl, pyrrolyl, tetrahydrotriazoloazepinyl, oxetanyl, piperidinyl, tetrahydropyranyl, tetrahydrofuranyl, piperazinyl, and pyrrolidinyl, unsubstituted or substituted with 1 to 3 groups of $R^x$. A subembodiment of Formula II is realized when X is S and $R^1$ is selected from $CH_3$, $CH_2CH_3$, $CH(CH_3)_2$, $-(CH_2)_n$cyclopropyl, $-(CH_2)_n$cyclobutyl, and $CH(cyclopropyl)_2$. Another subembodiment of the invention of Formula II is realized when X is S and $R^1$ is selected from $CH_3$, $CH_2CH_3$, $CH(CH_3)_2$, —$(CH_2)_n$cyclopropyl, —$(CH_2)_n$cyclobutyl, and $CH(cyclopropyl)_2$, $R^2$ is selected from hydrogen, $CH_3$, $OCH_2CF_3$, $OCH_3$, $CHF_2$, $OCH(CH_3)_2$, $OCH_2CHF_2$, $CF_3$, $C(O)NHCH_3$, $C(O)N(CH_3)_2$, $C(O)NH_2$, $C(O)OCH_3$, cyclopropyl, cyclobutyl, cyclopentyl, cyclohexyl, phenyl, —O-phenyl, pyridyl, tetrahydrotriazopyridyl, pyrazolyl, CN, $C(O)NH_2$, $C(O)NHCH_3$, and $C(O)N(CH_3)_2$, said cyclopropyl, cyclobutyl, cyclopentyl, cyclohexyl, phenyl, —O-phenyl, pyridyl, tetrahydrotriazopyridyl, pyrazolyl unsubstituted or substituted with 1 to 3 groups of $R^x$. Another subembodiment of Formula II is realized when X is S and $R^1$ is selected from $CH_3$, $CH_2CH_3$, $CH(CH_3)_2$, —$(CH_2)_n$cyclopropyl, —$(CH_2)_n$cyclobutyl, and $CH(cyclopropyl)_2$, and $R^2$ is selected from hydrogen, $CH_3$, cyclopropyl, $OCH_2CF_3$, $OCH_3$, $OCH(CH_3)_2$, $CHF_2$, $CF_3$, and $OCH_2CHF_2$. Another subembodiment of Formula II is realized when X is S and $R^1$ is selected from $CH_3$, $CH_2CH_3$, $CH(CH_3)_2$, —$(CH_2)_n$cyclopropyl, —$(CH_2)_n$cyclobutyl, and $CH(cyclopropyl)_2$, $R^2$ is selected from hydrogen, $CH_3$, cyclopropyl, $OCH_2CF_3$, $OCH_3$, $OCH(CH_3)_2$, $CHF_2$, $CF_3$, and $OCH_2CHF_2$, and $R^3$ is selected from the group consisting of hydrogen, $C_{1-6}$ alkyl, $CH_2CF_3$, $CHF_2$, $(CH_2)_nOCH_3$, $CH_2$pyridyl, $CH_2$morpholinyl, halogen, CN, $SO_2CH_3$, said alkyl, pyridyl, and morpholinyl unsubstituted or substituted with 1 to 3 groups from $R^x$.

A subembodiment of this aspect of the invention is realized when $R^b$ is pyridyl or thiazolyl, unsubstituted or substituted with 1 to 3 groups of $R^y$, $R^1$ is selected from $CH_3$, $CH_2CH_3$, $CH(CH_3)_2$, —$(CH_2)_n$cyclopropyl, —$(CH_2)_n$cyclobutyl, and $CH(cyclopropyl)_2$, and $R^2$ is selected from hydrogen, $CH_3$, cyclopropyl, $OCH_2CF_3$, $OCH_3$, $OCH(CH_3)_2$, $CHF_2$, $CF_3$, and $OCH_2CHF_2$. A subembodiment of this aspect of the invention is realized when $R^y$ is selected from hydrogen, $C_{1-6}$ alkyl, —$(CH_2)_nOC_{1-6}$ alkyl, $C_{3-6}$cycloalkyl, $C_{1-6}$ haloalkyl, -halogen, CN, $(CH_2)_nC_{4-10}$heterocyclyl, —$(CH_2)_nC_{5-10}$ heteroaryl, and —$SO_2C_{1-6}$ alkyl In another embodiment, the compounds of the invention include those identified herein as Examples in the tables below, and pharmaceutically acceptable salts thereof.

In another embodiment, the present invention provides pharmaceutical compositions comprising a pharmaceutically acceptable carrier and a compound of the invention or a pharmaceutically acceptable salt thereof.

In another embodiment, the present invention provides a method of treating a disease or disorder in which the LRRK2 kinase is involved, or one or more symptoms or conditions associated with said diseases or disorders, said method comprising administering to a subject (e.g., mammal, person, or patient) in need of such treatment an effective amount of a compound of the invention, or a pharmaceutically acceptable salt thereof, or pharmaceutically acceptable composition thereof. Non-limiting examples of such diseases or disorders, and symptoms associated with such diseases or disorders, each of which comprise additional independent embodiments of the invention, are described below.

Another embodiment provides the use of a compound of the invention, or a pharmaceutically acceptable salt thereof, and a pharmaceutically acceptable carrier, for the manufacture of a medicament for the treatment of Parkinson's Disease. The invention may also encompass the use of a compound of the invention, or a pharmaceutically acceptable salt thereof, and a pharmaceutically acceptable carrier, in therapy.

Another embodiment provides for medicaments or pharmaceutical compositions which may be useful for treating diseases or disorders in which LRRK2 is involved, such as Parkinson's Disease, which comprise a compound of the invention, or a pharmaceutically acceptable salt thereof, and a pharmaceutically acceptable carrier.

Another embodiment provides for the use of a compound of the invention which may be useful for treating diseases or disorders in which LRRK2 is involved, such as Parkinson's Disease.

Another embodiment provides a method for the manufacture of a medicament or a composition which may be useful for treating diseases or disorders in which LRRK2 is involved, such as Parkinson's Disease, comprising combining a compound of the invention with one or more pharmaceutically acceptable carriers.

The compounds of the invention may contain one or more asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. Unless a specific stereochemistry is indicated, the present invention is meant to encompass all such isomeric forms of these compounds.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

In the compounds of Formulae I and II the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formulae I and II. For example, different isotopic forms of hydrogen (H) include protium ($^1H$) and deuterium ($^2H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formulae I and II can be prepared without undue experimentation by conventional techniques well known to those skilled in the art or by processes analogous to those described in the Schemes and Examples herein using appropriate isotopically-enriched reagents and/or intermediates.

When a compound of the invention is capable of forming tautomers, all such tautomeric forms are also included within the scope of the present invention. For example, compounds including carbonyl $—CH_2C(O)—$ groups (keto forms) may undergo tautomerism to form hydroxyl $—CH{=}C(OH)—$ groups (enol forms). Both keto and enol forms, where present, are included within the scope of the present invention. Accordingly, where compounds of the invention, their salts, and solvates and prodrugs thereof, may exist in different tautomeric forms or in equilibrium among such forms, all such forms of the compound are embraced by, and included within the scope of the invention. Examples of such tautomers include, but are not limited to, ketone/enol tautomeric forms, imine-enamine tautomeric forms, and for example heteroaromatic forms such as the following moieties:

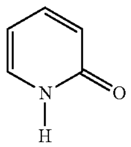

and

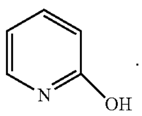

.

When any variable (e.g. $R^5$, etc.) occurs more than one time in any constituent, its definition on each occurrence is independent at every other occurrence. Also, combinations of substituents and variables are permissible only if such combinations result in stable compounds. Lines drawn into the ring systems from substituents represent that the indicated bond may be attached to any of the substitutable ring atoms. If the ring system is bicyclic, it is intended that the bond be attached to any of the suitable atoms on either ring of the bicyclic moiety.

It is understood that one or more silicon (Si) atoms can be incorporated into the compounds of the instant invention in place of one or more carbon atoms by one of ordinary skill in the art to provide compounds that are chemically stable and that can be readily synthesized by techniques known in the art from readily available starting materials. Carbon and silicon differ in their covalent radius leading to differences in bond distance and the steric arrangement when comparing analogous C-element and Si-element bonds. These differences lead to subtle changes in the size and shape of silicon-containing compounds when compared to carbon. One of ordinary skill in the art would understand that size and shape differences can lead to subtle or dramatic changes in potency, solubility, lack of off-target activity, packaging properties, and so on. (Diass, J. O. et al. Organometallics (2006) 5:1188-1198; Showell, G. A. et al. Bioorganic & Medicinal Chemistry Letters (2006) 16:2555-2558).

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. The phrase "optionally substituted with one or more substituents" should be understood as meaning that the group in question is either unsubstituted or may be substituted with one or more substituents.

Absolute stereochemistry is illustrated by the use of hashed and solid wedge bonds. As shown in Illus-I and Illus-II. Accordingly, the methyl group of Illus-I is emerging from the page of the paper and the ethyl group in Illus-II is descending into the page, where the cyclohexene ring resides within the plane of the paper. It is assumed that the hydrogen on the same carbon as the methyl group of Illus-I descends into the page and the hydrogen on the same carbon as the ethyl group of Illus-II emerges from the page. The convention is the same where both a hashed and solid rectangle are appended to the same carbon as in Illus-III, the methyl group is emerging from the plane of the paper and the ethyl group is descending into the plane of the paper with the cyclohexene ring in the plane of the paper.

Illus-1

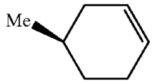

Illus-2

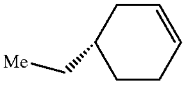

Illus-3

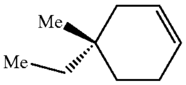

As is conventional, unless otherwise noted in accompanying text, ordinary "stick" bonds or "wavy" bonds indicate that all possible stereochemistry is represented, including, pure compounds, mixtures of isomers, and racemic mixtures.

As used herein, unless otherwise specified, the following terms have the following meanings:

The phrase "at least one" used in reference to the number of components comprising a composition, for example, "at least one pharmaceutical excipient" means that one member of the specified group is present in the composition, and more than one may additionally be present. Components of a composition are typically aliquots of isolated pure material added to the composition, where the purity level of the isolated material added into the composition is the normally accepted purity level for a reagent of the type.

"at least one" used in reference to substituents appended to a compound substrate, for example, a halogen or a moiety appended to a portion of a structure replacing a hydrogen, means that one substituent of the group of substituents specified is present, and more than one of said substituents may be bonded to any of the defined or chemically accessible bonding points of the substrate.

Whether used in reference to a substituent on a compound or a component of a pharmaceutical composition the phrase "one or more", means the same as "at least one";

"concurrently" and "contemporaneously" both include in their meaning (1) simultaneously in time (e.g., at the same time); and (2) at different times but within the course of a common treatment schedule;

"consecutively" means one following the other;

"sequentially" refers to a series administration of therapeutic agents that awaits a period of efficacy to transpire between administering each additional agent; this is to say that after administration of one component, the next component is administered after an effective time period after the first component; the effective time period is the amount of time given for realization of a benefit from the administration of the first component;

"effective amount" or "therapeutically effective amount" is meant to describe the provision of an amount of at least one compound of the invention or of a composition comprising at least one compound of the invention which is effective in treating or inhibiting a disease or condition described herein, and thus produce the desired therapeutic, ameliorative, inhibitory or preventative effect. For example, in treating central nervous system diseases or disorders with one or more of the compounds described herein "effective amount" (or "therapeutically effective amount") means, for example, providing the amount of at least one compound of Formula I, or Formula II, that results in a therapeutic response in a patient afflicted with a central nervous system disease or disorder ("condition"), including a response suitable to manage, alleviate, ameliorate, or treat the condition or alleviate, ameliorate, reduce, or eradicate one or more symptoms attributed to the condition and/or long-term stabilization of the condition, for example, as may be determined by the analysis of pharmacodynamic markers or clinical evaluation of patients afflicted with the condition;

"patient" and "subject" means an animal, such as a mammal (e.g., a human being) and is preferably a human being;

"prodrug" means compounds that are rapidly transformed, for example, by hydrolysis in blood, in vivo to the parent compound, e.g., conversion of a prodrug of Formula I or II or to a salt thereof; a thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference; the scope of this invention includes prodrugs of the novel compounds of this invention. The present invention includes within its scope prodrugs of the compounds of this invention. In general, such prodrugs will be functional derivatives of the compounds of this invention which are readily convertible in vivo into the required compound. Thus, in the methods of treatment of the present invention, the terms "administration of" or "administering a" compound shall encompass the treatment of the various conditions described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs," ed. H. Bundgaard, Elsevier, 1985. Metabolites of these compounds include active species produced upon introduction of compounds of this invention into the biological milieu.

The term "substituted" means that one or more of the enumerated substituents can occupy one or more of the bonding positions on the substrate typically occupied by "—H", provided that such substitution does not exceed the normal valency rules for the atom in the bonding configuration presented in the substrate, and that the substitution ultimately provides a stable compound, which is to say that such substitution does not provide compounds with mutually reactive substituents located geminal or vicinal to each other; and wherein the substitution provides a compound sufficiently robust to survive isolation to a useful degree of purity from a reaction mixture.

Where optional substitution of a moiety is described (e.g. "optionally substituted") the term means that if substituents are present, one or more of the enumerated substituents for the specified substrate can be present on the substrate in a bonding position normally occupied by the default substituent normally occupying that position. For example, a default substituent on the carbon atoms of an alkyl moiety is a hydrogen atom, an optional substituent can replace the default substituent.

As used herein, unless otherwise specified, the following terms used to describe moieties, whether comprising the entire definition of a variable portion of a structural representation of a compound of the invention or a substituent appended to a variable portion of a structural representation of a group of compounds of the invention have the following meanings, and unless otherwise specified, the definitions of each term (i.e., moiety or substituent) apply when that term is used individually or as a component of another term (e.g., the definition of aryl is the same for aryl and for the aryl portion of arylalkyl, alkylaryl, arylalkynyl moieties, and the like); moieties are equivalently described herein by structure, typographical representation or chemical terminology without intending any differentiation in meaning, for example, an "acyl" substituent may be equivalently described herein by the term "acyl", by typographical representations "R'—(C═O)—" or "R'—C(O)—", or by a structural representation:

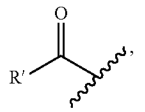

equally, with no differentiation implied using any or all of these representations;

The term "alkyl" (including the alkyl portions of other moieties, such as trifluoromethyl-alkyl- and alkoxy-) means a straight or branched aliphatic hydrocarbon moiety comprising up to about 20 carbon atoms (for example, a designation of "$C_{1-20}$-alkyl" indicates an aliphatic hydrocarbon moiety of from 1 to 20 carbon atoms). In some embodiments, alkyls preferably comprise up to about 10 carbon atoms, unless the term is modified by an indication that a shorter chain is contemplated, for example, an alkyl moiety of from 1 up to 8 carbon atoms is designated herein "$C_{1-8}$-alkyl". Where the term "alkyl" is indicated with two hyphens (i.e., "-alkyl-" it indicates that the alkyl moiety is bonded in a manner that the alkyl moiety connects the substituents on either side of it, for example, "-alkyl-OH" indicates an alkyl moiety connecting a hydroxyl moiety to a substrate.

The term "haloalkyl" refers to an alkyl in which one or more hydrogen atoms are replaced by halo, and includes alkyl moieties in which all hydrogens have been replaced by halo (e.g., perfluoroalkyl). Alkyl and haloalkyl groups may be optionally inserted with O, N, or S.

The term "cycloalkyl" means a moiety having a main hydrocarbon chain forming a mono- or bicyclo-cyclic aliphatic moiety comprising at least 3 carbon atoms (the minimum number necessary to provide a monocyclic moiety) up to the maximum number of specified carbon atoms, generally 8 for a monocyclic moiety and 10 for a bicyclic moiety. Examples of cycloalkyl moieties include, but are not limited to, cyclopropyl, cyclobutyl, cyclopentyl or cyclohexyl. The term "cycloalkyl" also includes non-aromatic, fused multicyclic ring system comprising up to 20 carbon atoms which may optionally be substituted as defined herein for "alkyl" generally. Suitable multicyclic cycloalkyls are, for example, but are not limited to: 1-decalin; norbornyl; adamantly; and the like;

As used herein, when the term "alkyl" is modified by "substituted" or "optionally substituted", it means that one or more C—H bonds in the alkyl moiety group is substituted, or optionally may be substituted, by a substituent bonded to the alkyl substrate which is called out in defining the moiety.

Where a structural formula represents bonding between a moiety and a substrate using a bonding line that terminates in the middle of the structure, for example the following representations:

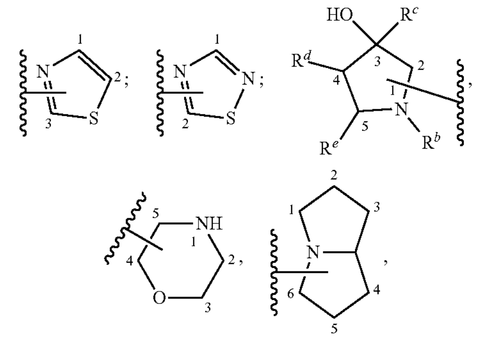

whether or not numbered the structure indicates that unless otherwise defined the moiety may be bonded to the substrate through any of available ring atom, for example, the numbered atoms of the example moieties;

"Aryl" refers to (i) phenyl, (ii) 9- or 10-membered bicyclic, fused carbocylic ring systems in which at least one ring is aromatic, and (iii) 11- to 14-membered tricyclic, fused carbocyclic ring systems in which at least one ring is aromatic. Suitable aryls include, for example, substituted and unsubstituted phenyl and substituted and unsubstituted naphthyl. An aryl of particular interest is unsubstituted or substituted phenyl.

"Heteroaryl" refers to (i) a 5- or 6-membered heteroaromatic ring containing from 1 to 4 heteroatoms independently selected from N, O and S, wherein each N is optionally in the form of an oxide, and (ii) a 9- or 10-membered bicyclic fused ring system, wherein the fused ring system of (ii) contains from 1 to 6 heteroatoms independently selected from N, O and S, wherein each ring in the fused ring system contains zero, one or more than one heteroatom, at least one ring is aromatic, each N is optionally in the form of an oxide, and each S in a ring which is not aromatic is optionally S(O) or $S(O)_2$. Suitable 5- and 6-membered heteroaromatic rings include, for example, pyridyl, 3-fluroropyridyl, 4-fluoropyridyl, 3-methoxypyridyl, 4-methoxypyridyl, pyrrolyl, pyrazinyl, pyrimidinyl, pyridazinyl, triazinyl, thienyl, furanyl, imidazolyl, pyrazolyl, triazolyl (i.e., 1,2,3-triazolyl or 1,2,4-triazolyl), tetrazolyl, thiazolyl, oxazolyl, isooxazolyl, oxadiazolyl (i.e., the 1,2,3-, 1,2,4-, 1,2,5-(furazanyl), or 1,3,4-isomer), oxatriazolyl, thiazolyl, isothiazolyl, and thiadiazolyl. Suitable 9- and 10-membered heterobicyclic, fused ring systems include, for example, benzofuranyl, indolyl, indazolyl, naphthyridinyl, isobenzofuranyl, benzopiperidinyl, benzisoxazolyl, benzoxazolyl, chromenyl, quinolinyl, isoquinolinyl, isoindolyl, benzopiperidinyl, benzofuranyl, imidazo[1,2-a]pyridinyl, benzotriazolyl, indazolyl, indolinyl, triazoloazepinyl, tetrahydrotriazolyl, and isoindolinyl. A class of heteroaryls includes unsubstituted or substituted pyridyl or pyrimidyl, and particularly unsubstituted or substituted pyridyl.

The term "heterocyclic or "heterocyclyl" refers to (i) a saturated 4- to 7-membered cyclized ring and (ii) an unsaturated, non-aromatic 4 to 7-membered cyclized ring comprised of carbon atoms and 1-4 heteroatoms independently selected from O, N and S. Heterocyclic rings within the scope of this invention include, for example, azetidinyl, piperidinyl, morpholinyl, thiomorpholinyl, thiazolidinyl, isothiazolidinyl, oxazolidinyl, isoxazolidinyl, pyrrolidinyl, imidazolidinyl, piperazinyl, tetrahydrofuranyl, tetrahydrothienyl, pyrazolidinyl, hexahydropyrimidinyl, thiazinanyl, thiazepanyl, azepanyl, diazepanyl, tetrahydropyranyl, tetrahydrothiopyranyl, and dioxanyl. Examples of 4- to 7-membered, unsaturated, non-aromatic heterocyclic rings within the scope of this invention include mono-unsaturated heterocyclic rings corresponding to the saturated heterocyclic rings listed in the preceding sentence in which a single bond is replaced with a double bond (e.g., a carbon-carbon single bond is replaced with a carbon-carbon double bond). A class of heterocyclic rings are 4 to 6-membered saturated monocyclic rings comprised of carbon atoms and 1 or 2 heteroatoms, wherein the heteroatoms are selected from N, O and S. Examples of 4 to 6 membered heterocyclic rings include but are not limited to, azetidinyl, pyrrolidinyl, piperidinyl, piperazinyl, morpholinyl, thiomorpholinyl, tetrahydrofuranyl, tetrahydropyranyl and tetrahydrothiopyranyl, and a sub-class thereof is piperidinyl, pyrrolidinyl, tetrahydrofuranyl or tetrahydropyranyl.

The term "halogen" means fluorine, chlorine, bromine, or iodine; preferred halogens, unless specified otherwise where the term is used, are fluorine, chlorine and bromine, a substituent which is a halogen atom means —F, —Cl, —Br, or —I, and "halo" means fluoro, chloro, bromo, or iodo substituents bonded to the moiety defined, for example, "haloalkyl" means an alkyl, as defined above, wherein one or more of the bonding positions on the alkyl moiety typically occupied by hydrogen atoms are instead occupied by a halo group, perhaloalkyl (or "fully halogenated" alkyl) means that all bonding positions not participating in bonding the alkyl substituent to a substrate are occupied by a halogen, for example, where the alkyl is selected to be methyl, the term perfluoroalkyl means $—CF_3$;

The term "hydroxyl" and "hydroxy" means an HO— group, "hydroxyalkyl" means a substituent of the formula: "HO-alkyl-", wherein the alkyl group is bonded to the substrate and may be substituted or unsubstituted as defined above; preferred hydroxyalkyl moieties comprise a lower alkyl; Non-limiting examples of suitable hydroxyalkyl groups include hydroxymethyl and 2-hydroxyethyl; and The bonding sequence is indicated by hyphens where moieties are represented in text, for example -alkyl, indicates a single bond between a substrate and an alkyl moiety, -alkyl-X, indicates that an alkyl group bonds an "X" substituent to a substrate, and in structural representation, bonding sequence is indicated by a wavy line terminating a bond representation, for example:

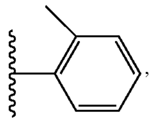 [SMILES: *c1ccccc1C]

indicates that the methylphenyl moiety is bonded to a substrate through a carbon atom ortho to the methyl substituent, while a bond representation terminated with a wavy line and drawn into a structure without any particular indication of an atom to which it is bonded indicates that the moiety may be bonded to a substrate via any of the atoms in the moiety which are available for bonding as described in the examples above.

The line —, as a bond generally indicates a mixture of, or either of, the possible isomers, e.g., containing (R)- and (S)-stereochemical configuration. For example:

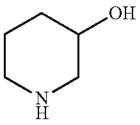

encompasses

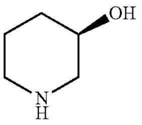

and/or

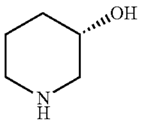

Furthermore, unwedged-bolded or unwedged-hashed lines are used in structures containing multiple stereocenters in order to depict relative configuration where it is known. For example:

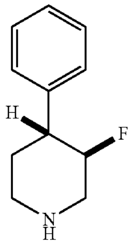

means that the fluorine and hydrogen atoms are on the same face of the piperidine ring, but represents a mixture of, or one of, the possible isomers at right

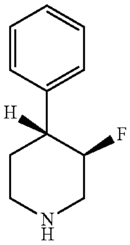

and/or

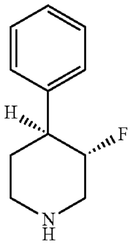

whereas:

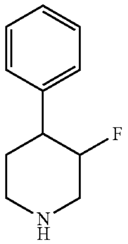 [SMILES: FC1CNCCC1c1ccccc1]

represents a mixture of, or one of, the possible isomers at right

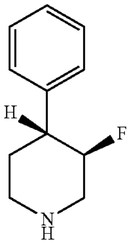

and/or

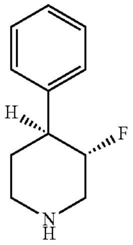

and/or

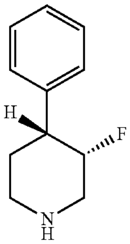

and/or

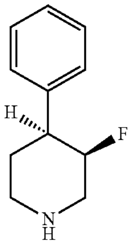

In all cases, compound name(s) accompany the structure drawn and are intended to capture each of the stereochemical permutations that are possible for a given structural isomer based on the synthetic operations employed in its preparation. Lists of discrete stereoisomers that are conjoined using or indicate that the presented compound (e.g. 'Example number') was isolated as a single stereoisomer, and that the identity of that stereoisomer corresponds to one of the possible configurations listed. Lists of discrete stereoisomers that are conjoined using and indicate that the presented compound was isolated as a racemic mixture or diastereomeric mixture.

A specific absolute configuration is indicated by use of a wedged-bolded or wedged-hashed line. Unless a specific absolute configuration is indicated, the present invention is meant to encompass all such stereoisomeric forms of these compounds.

In this specification, where there are multiple oxygen and/or sulfur atoms in a ring system, there cannot be any adjacent oxygen and/or sulfur present in said ring system.

As well known in the art, a bond drawn from a particular atom wherein no moiety is depicted at the terminal end of the bond indicates a methyl group bound through that bond to the atom, unless stated otherwise. For example:

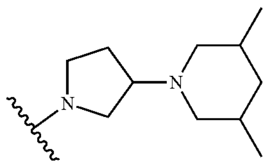

represents

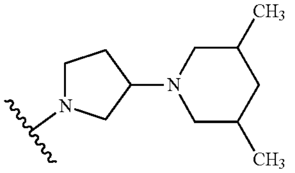

Unsatisfied valences in the text, schemes, examples, structural formulae, and any Tables herein is assumed to have a hydrogen atom or atoms of sufficient number to satisfy the valences. One or more compounds of the invention may also exist as, or optionally be converted to, a solvate. Preparation of solvates is generally known. Thus, for example, M. Caira et al, *J Pharmaceutical Sci.,* 93(3), 601-611 (2004) describe the preparation of the solvates of the antifungal fluconazole in ethyl acetate as well as from water. Similar preparations of solvates, and hemisolvate, including hydrates (where the solvent is water or aqueous-based) and the like are described by E. C. van Tonder et al, *AAPS PharmSciTech.,* 5(1), article 12 (2004); and A. L. Bingham et al, *Chem. Commun.,* 603-604 (2001). A typical, non-limiting, process involves dissolving the inventive compound in desired amounts of the desired solvent (for example, an organic solvent, an aqueous solvent, water or mixtures of two or more thereof) at a higher than ambient temperature, and cooling the solution, with or without an antisolvent present, at a rate sufficient to form crystals which are then isolated by standard methods. Analytical techniques such as, for example I.R. spectroscopy, show the presence of the solvent (including water) in the crystals as a solvate (or hydrate in the case where water is incorporated into the crystalline form).

This invention also includes the compounds of this invention in isolated and purified form obtained by routine techniques. Polymorphic forms of the compounds of Formula I, or Formula II, and of the salts, solvates and prodrugs of the compounds of Formula I, or Formula II are intended to be included in the present invention. Certain compounds of the invention may exist in different isomeric forms (e.g., enantiomers, diastereoisomers, atropisomers). The inventive compounds include all isomeric forms thereof, both in pure form and admixtures of two or more, including racemic mixtures.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives wherein the parent compound is modified by making acid or base salts thereof. Salts in the solid form may exist in more than one crystal structure and may also be in the form of hydrates. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. Salts derived from inorganic bases include aluminum, ammonium, calcium, copper, ferric, ferrous, lithium, magnesium, manganic salts, manganous, potassium, sodium, zinc, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. In one aspect of the invention the salts are citric, hydrobromic, hydrochloric, maleic, phosphoric, sulfuric, fumaric, and tartaric acids. Similarly, the salts of the acidic compounds are formed by reactions with the appropriate inorganic or organic base.

The terms "treating" or "treatment" (of, e.g., a disease, disorder, or conditions or associated symptoms, which together or individually may be referred to as "indications") as used herein include: inhibiting the disease, disorder or condition, i.e., arresting or reducing the development of the disease or its biological processes or progression or clinical symptoms thereof; or relieving the disease, i.e., causing regression of the disease or its biological processes or progression and/or clinical symptoms thereof. "Treatment" as used herein also refers to control, amelioration, or reduction of risks to the subject afflicted with a disease, disorder or condition in which LRRK2 is involved. The terms "preventing" or "prevention" or "prophylaxis" of a disease, disorder or condition as used herein includes: impeding the development or progression of clinical symptoms of the disease, disorder, or condition in a mammal that may be exposed to or predisposed to the disease, disorder or condition but does not yet experience or display symptoms of the disease, and the like.

As would be evident to those skilled in the art, subjects treated by the methods described herein are generally mammals, including humans and non-human animals (e.g., laboratory animals and companion animals), in whom the inhibition of LRRK2 kinase activity is indicated or desired. The term "therapeutically effective amount" means the amount of the subject compound that will elicit the biological or medical response of a tissue, system, animal or human that is being sought by the researcher, veterinarian, medical doctor or other clinician.

The term "composition" as used herein is intended to encompass a product comprising a compound of the invention or a pharmaceutically acceptable salt thereof, together with one or more additional specified ingredients in the specified amounts, as well as any product which results, directly or indirectly, from combination of the specified ingredients in the specified amounts. Such term in relation to a pharmaceutical composition, is intended to encompass a product comprising the active ingredient(s), which include a compound of the invention or a pharmaceutically acceptable salt thereof, optionally together with one or more additional active ingredients, and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention, or a pharmaceutically acceptable salt thereof, and a pharmaceutically acceptable carrier.

As noted above, additional embodiments of the present invention are each directed to a method for the treatment a disease, disorder, or condition, or one or more symptoms thereof ("indications") in which the LRRK2 kinase is involved and for which the inhibition of LRRK2 kinase is desired, which method comprises administering to a subject in need of such treatment a therapeutically effective amount of a compound of the invention, or a pharmaceutically acceptable salt thereof, or a pharmaceutical composition comprising said compound or salt thereof.

In another embodiment, the present invention is directed to a method for the manufacture of a medicament for inhibition of LRRK2 receptor activity in a subject comprising combining a compound of the present invention, or a pharmaceutically acceptable salt thereof, with a pharmaceutical carrier or diluent.

One such embodiment provides a method of treating Parkinson's disease in a subject in need thereof, said method comprising administering to a subject in need of such treatment a therapeutically effective amount of a compound of the invention, or a pharmaceutically acceptable salt thereof, or a pharmaceutical composition comprising said compound or salt thereof. In one such embodiment, the subject is a human.

Another embodiment provides a method for the treatment or prophylaxis of neurologic damage associated with Parkinson's disease in a subject in need thereof. Another embodiment provides a method of treating or improving dopaminergic tone to provide symptomatic relief in a subject in need thereof, for example, in treating, alleviating, ameliorating, or managing motor and non-motor symptoms of Parkinson's disease.

Another embodiment provides a method for the treatment or prophylaxis of abnormal motor symptoms associated with Parkinson's disease (including but not limited to bradykinesia, rigidity and resting tremor). Another embodiment provides a method for the treatment or prophylaxis of abnormal non-motor symptoms associated with Parkinson's disease (including but not limited to cognitive dysfunction, autonomic dysfunction, emotional changes and sleep disruption); Lewy body dementia; and L-Dopa induced dyskinesias. Each said method independently comprises administering to a patient in need of such treatment an effective amount of a compound of the invention, or a pharmaceutically acceptable salt thereof, or pharmaceutically acceptable composition thereof.

Non-limiting examples of additional indications in which LRRK2 is involved and in which the treatment or prophylaxis of said indications in a subject in need thereof are contemplated include the following, each of which, alone or in combination, comprise additional embodiments of the invention: Alzheimer's disease, mild cognitive impairment, the transition from mild cognitive impairment to Alzheimer's disease, tauopathy disorders characterized by hyperphosphorylation of tau such as argyrophilic grain disease, Pick's disease, corticobasal degeneration, progressive supranuclear palsy, inherited frontotemporal dementia, and Parkinson's disease linked to chromosome 17.

Additional indications include neuroinflammation, including neuroinflammation associated with of microglial inflammatory responses associated with multiple sclerosis, HIV-induced dementia, ALS, ischemic stroke, traumatic brain injury and spinal cord injury.

Additional indications include diseases of the immune system including lymphomas, leukemias, multiple sclerosis, rheumatoid arthritis, systemic lupus erythematosus, autoimmune hemolytic anemia, pure red cell aplasia, idiopathic thrombocytopenic pupura (ITP), Evans Syndrome, vasculitis, bullous skin disorder, type I diabetes mellitus, Sjorgen's syndrome, Delvic's disease, inflammatory myopathies, and ankylosing spondylitis.

Additional indications include renal cancer, breast cancer, lung cancer, prostate cancer, and acute myelogenous leukemia (AML) in subjects expressing the LRRK2 G2019S mutation.

Additional indications include papillary renal and thyroid carcinomas in a subject in whom LRRK2 is amplified or overexpressed.

Additional indications include chronic autoimmune diseases including Crohn's disease and leprosy.

The compounds of the present invention may be used in combination with one or more other drugs in the treatment, prevention, control, amelioration, or reduction of risk of diseases or conditions for which compounds of Formula I and Formula II, or the other drugs may have utility, where the combination of the drugs together are safer or more effective than either drug alone. Such other drug(s) may be administered, by a route and in an amount commonly used therefore, contemporaneously or sequentially with a compound of Formula I. When a compound Formula I or Formula II is used contemporaneously with one or more other drugs, a pharmaceutical composition in unit dosage form containing such other drugs and the compound of Formula I or Formula II is preferred. However, the combination therapy may also include therapies in which the compound of Formula I or Formula II and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of Formula I or Formula II.

For example, the present compounds may be used in conjunction with one or more additional therapeutic agents, for example: L-DOPA; dopaminergic agonists such as quinpirole, ropinirole, pramipexole, pergolide and bromocriptine; MAO-B inhibitors such as rasagiline, deprenyl and selegiline; DOPA decarboxylase inhibitors such as carbidopa and benserazide; and COMT inhibitors such as tolcapone and entacapone; or potential therapies such as an adenosine A2a antagonists, metabotropic glutamate receptor 4 modulators, or growth factors such as brain derived neurotrophic factor (BDNF), and a pharmaceutically acceptable carrier.

The above combinations include combinations of a compound of the present invention not only with one other active compound, but also with two or more other active compounds. Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefore, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

The weight ratio of the compound of the present invention to the other active ingredient(s) may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, or from about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s), and via the same or different routes of administration.

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, buccal or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, solutions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia; and lubricating agents, for example magnesium stearate, stearic acid or talc. The tablets may be uncoated, or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release. Oral tablets may also be formulated for immediate release, such as fast melt tablets or wafers, rapid dissolve tablets or fast dissolve films.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or acetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions and the like, containing the compounds of the present invention are employed. Similarly, transdermal patches may also be used for topical administration.

The pharmaceutical composition and method of the present invention may further comprise other therapeutically active compounds as noted herein which are usually applied in the treatment of the above-mentioned pathological conditions.

In the treatment, prevention, control, amelioration, or reduction of risk of conditions which require inhibition of LRRK2 kinase activity an appropriate dosage level will generally be about 0.01 to 500 mg per kg patient body weight per day which can be administered in single or multiple doses. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions may be provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day or may be administered once or twice per day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Methods for preparing the compounds of this invention are illustrated in the following Schemes and Examples. Starting materials are made according to procedures known in the art or as illustrated herein.

PREPARATIVE EXAMPLES

The compounds of the present invention can be prepared according to the following schemes and specific examples, or modifications thereof, using readily available starting materials, reagents and conventional synthesis procedures. It is also possible to make use of variants which are themselves known to those of ordinary skill in this art but are not mentioned in detail. The general procedures for making the compounds claimed in this invention can be readily understood by one skilled in the art from viewing the following schemes and descriptions. Abbreviations used in the experimentals may include, but are not limited to the following:

| | |
|---|---|
| Aq | Aqueous |
| BHT | Butylated hydroxytoluene |
| Bpy | 2,2'-Bipyridine |
| calc'd | Calculated |
| COMU | (1-Cyano-2-ethoxy-2-oxoethylidenaminooxy)dimethylamino-morpholino-carbenium hexafluorophosphate |
| DCE | 1,2-Dichloroethane |
| DIAD | Diisopropyl azodicarboxylate |
| DMAP | 4-(Dimethylamino)pyridine |

-continued

| | |
|---|---|
| DMF | N,N-Dimethylformamide |
| DMSO | Dimethyl sulfoxide |
| ESI | Electrospray ionization |
| EtOAc | Ethyl acetate |
| H | Hour(s) |
| HATU | N-[(Dimethylamino)-1H-1,2,3-triazolo-[4,5-b]pyridin-1-ylmethylene]-N-methylmethanaminium hexafluorophosphate N-oxide |
| HPLC | High performance liquid chromatography |
| LiHMDS | Lithium bis(trimethylsilyl)amide |
| m/z | Mass-to-charge ratio |
| 2-MeTHF | 2-Methyltetrahydrofuran |
| min | Minute(s) |
| MS | Mass spectrometry |
| Ms | Methanesulfonyl, mesyl |
| NMR | Nuclear magnetic resonance |
| $PdCl_2$(dppf) | [1,1'-Bis(diphenylphosphino)ferrocene]dichloropalladium(II) |
| PS-$PPh_3$ | Polystyrene-bound triphenylphosphine |
| PyAOP | (7-Azabenzotriazol-1-yloxy)trispyrrolidinophosphonium hexafluorophosphate |
| rac-BINAP-Pd-G3 | Racemic methanesulfonato[2,2'-bis(diphenylphosphino)-1,1'-binaphthyl](2'-amino-1,1'-biphenyl-2-yl)palladium(II) |
| rt | Room temperature |
| RuPhos-Pd-G2 | Chloro(2-dicyclohexylphosphino-2',6'-diisopropoxy-1,1'-biphenyl)[2-(2'-amino-1,1'-biphenyl)]palladium(II) |
| SEM | [2-(Trimethylsilyl)ethoxy]methyl acetal |
| SFC | Supercritical fluid chromatography |
| TFA | Trifluoroacetic acid |
| THF | Tetrahydrofuran |
| tR | Retention time |
| w/v | Weight by volume |
| wt % | Weight percent |

General Experimental Information:

Unless otherwise noted, all reactions are magnetically stirred. Unless otherwise noted, when diethyl ether is used in the experiments described below, it is Fisher ACS certified material and is stabilized with BHT. Unless otherwise noted, "concentrated" and/or "solvent removed under reduced pressure" means evaporating the solvent from a solution or mixture using a rotary evaporator or vacuum pump. Unless otherwise noted, flash chromatography is carried out on a Teledyne Isco (Lincoln, NE), Analogix (Burlington, WI), or Biotage (Stockholm, SWE) automated chromatography system using a commercially available cartridge as the column. Columns may be purchased from Teledyne Isco, Analogix, Biotage, Varian (Palo Alto, CA), or Supelco (Bellefonte, PA) and are usually filled with silica gel as the stationary phase. Reversed phase preparative HPLC conditions, where used, can be found at the end of each experimental section. Aqueous solutions were concentrated on a Genevac (Ipswich, ENG) or by freeze-drying/lyophilization. Unless otherwise noted, all LRRK2 pIC50 data presented in tables refers to the LRRK2 G2019S Km ATP LanthaScreen™ assay (Life Technologies Corp., Carlsbad, CA) that is described in the Biological Assay section.

General Synthetic Schemes

The compounds of the invention may be prepared by methods known in the art of organic synthesis as set forth in part by the following general synthetic schemes and specific preparative examples. Starting materials are available commercially or may be prepared by known methods.

General Scheme 1

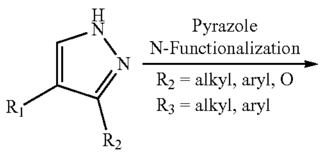

-continued

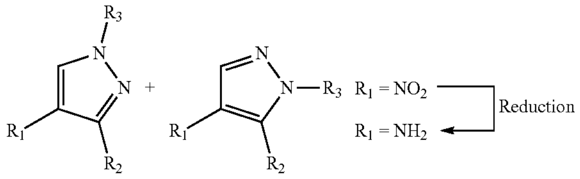

In General Scheme 1, commercially available or synthetically prepared 4-substituted pyrazoles could be substituted using a number of synthetic transformations commonly known to those skilled in the art, including, but not limited to, base-mediated alkylation, a Mitsunobu reaction, an epoxide-opening reaction, or a Chan-Lam coupling to afford N-substituted pyrazoles. In instances where $R^1$=$NO_2$, reduction to the corresponding 4-aminopyrazole was performed either early or later in the synthesis, depending on the needs of the operator. In instances where $R^2 \neq H$, a mixture of 1,3,4- and 1,4,5-trisubstituted pyrazoles can be formed. Representative preparative examples are described in more detail below.

General Scheme 2

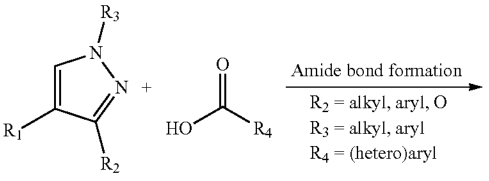

-continued

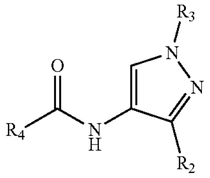

In General Scheme 2, commercially available or synthetically prepared carboxylic acids were coupled with the aforementioned 4-aminopyrazoles (General Scheme 1). Representative preparative examples are described in more detail below.

General Scheme 3

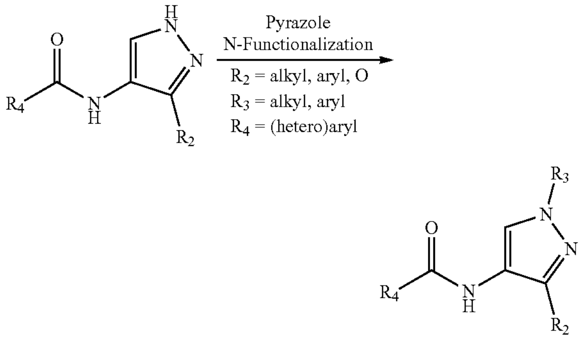

In General Scheme 3, N-unsubstituted (hetero)aroyl 4-aminopyrazoles (General Scheme 2) are alkylated using a number of synthetic transformations commonly known to those skilled in the art, including, but not limited to, base-mediated alkylation, a Mitsunobu reaction, an epoxide-opening reaction, or a Chan-Lam coupling reaction to afford N-substituted (hetero)aroyl 4-aminopyrazoles. Representative preparative examples are described in more detail below.

General Scheme 4

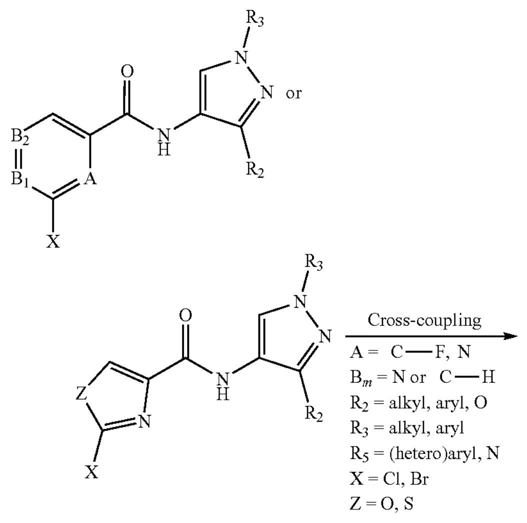

-continued

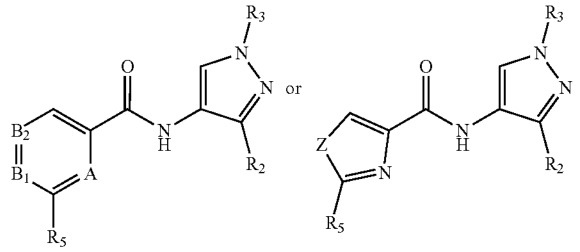

In General Scheme 4, halogenated (hetero)aroyl 4-aminopyrazoles (General Scheme 2) are substituted with (hetero)aryl or alkyl groups. While not exclusive, the most common reactions employed are C—C cross-coupling reactions (e.g., Suzuki reaction, Stille reaction, etc.) using Pd or Cu catalysts. Building blocks are commonly known to those skilled in the art, including, but not limited to, boronic acids, boronate esters, or aliphatic nitriles. Representative preparative examples are described in more detail below.

Synthesis of Common Intermediates

Scheme 1. Syntheis of 3-(difluoromethyl)-1H-pyrazol-4-amine

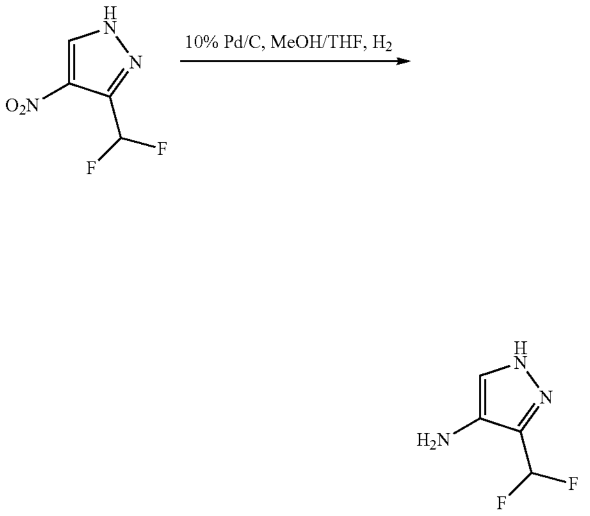

3-(Difluoromethyl)-1H-pyrazol-4-amine (Intermediate 1)

To a mixture of 3-(difluoromethyl)-4-nitro-1H-pyrazole (500 mg, 3.07 mmol), 2-MeTHF (5 mL), and MeOH (5 mL) was added 10 wt % Pd/C (131 mg, 0.061 mmol). The reaction vessel was evacuated and backfilled thrice with $N_2$, and then thrice with $H_2$. The resulting suspension was stirred at rt for 2 h. The reaction vessel was evacuated and backfilled thrice with $N_2$, and the reaction mixture was sparged with $N_2$ for 5 min. The reaction mixture was filtered through a plug of CELITE diatomaceous earth, and the filtrate was concentrated to dryness in vacuo to afford 3-(difluoromethyl)-1H-pyrazol-4-amine, which was used without further purification. MS (ESI) m/z $C_4H_6F_2N_3$ $[M+H]^+$ calc'd 134. found 134. $^1H$ NMR (500 MHz, $CDCl_3$) δ 11.62 (s, 1H), 8.39 (s, 1H), 7.23 (t, J=54.9 Hz, 1H).

Scheme 2. Synthesis of 1,3-dicyclopropyl-1H-pyrazol-4-amine

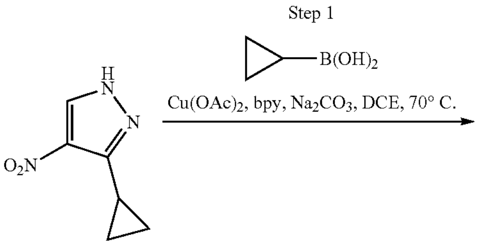

-continued

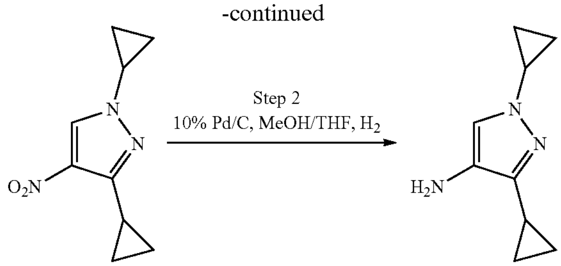

1,3-Dicyclopropyl-1H-pyrazol-4-amine
(Intermediate 2)

Step 1: A reaction vessel containing a mixture of 3-cyclopropyl-4-nitro-1H-pyrazole (236 mg, 1.54 mmol), cyclopropylboronic acid (264 mg, 3.08 mmol), $Cu(OAc)_2$ (279 mg, 1.54 mmol), 2,2'-bipyridine (240 mg, 1.54 mmol), and $Na_2CO_3$ (326 mg, 3.08 mmol) was put under an atmosphere of $N_2$. To this vessel was added DCE (12 mL). The resulting suspension was heated to 70° C. overnight, and then cooled to rt. The reaction mixture was filtered through a plug of CELITE. The filtrate was diluted with EtOAc, and the organic layer was washed with aqueous 1 M HCl, dried over $MgSO_4$, filtered, and concentrated to dryness in vacuo to afford crude 1,3-dicyclopropyl-4-nitro-1H-pyrazole. MS (ESI) m/z $C_9H_{12}N_3O_2$ $[M+H]^+$ calc'd 194. found 194.

Step 2: To crude 1,3-dicyclopropyl-4-nitro-1H-pyrazole was added THF (4 mL), 10 wt % Pd/C (164 mg, 0.15 mmol), and MeOH (4 mL). The resulting suspension was put under an atmosphere of $H_2$ and was stirred at rt overnight. The reaction mixture was filtered through a plug of CELITE, and the filtrate was concentrated to dryness in vacuo to afford 1,3-dicyclopropyl-1H-pyrazol-4-amine, which was used without further purification. MS (ESI) $C_9H_{14}N_3$ $[M+H]^+$ calc'd 164. found 164.

Intermediates in Table 1 below were prepared using procedures analogous to those described in Scheme 2.

TABLE 1

| Intermediate | Structure | Name | Exact Mass $[M + H]^+$ |
| --- | --- | --- | --- |
| 3 | 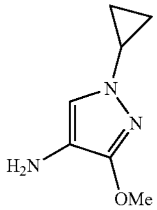 [SMILES: COc1nn(C2CC2)cc1N] | 1-cyclopropyl-3-methoxy-1H-pyrazol-4-amine | calc'd 154, found 154 |
| 4 | 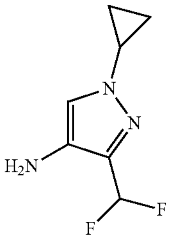 [SMILES: Nc1cn(C2CC2)nc1C(F)F] | 1-cyclopropyl-3-(difluoromethyl)-1H-pyrazol-4-amine | calc'd 174, found 174 |

Scheme 3. Synthesis of 1-cyclobutyl-3-methyl-1H-pyrazol-4-amine

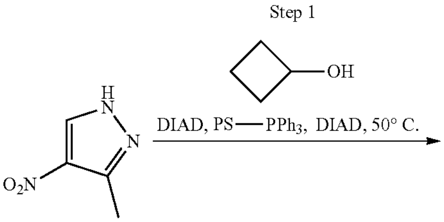

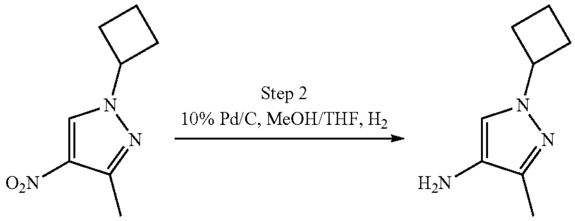

1-Cyclobutyl-3-methyl-1H-pyrazol-4-amine
(Intermediate 5)

Step 1: To a mixture of 3-methyl-4-nitro-1H-pyrazole (195 mg, 1.54 mmol), polystyrene-$PPh_3$ resin (1.12 g, 2.2 mmol/g, 2.46 mmol), and THF (8 mL) were added sequentially cyclobutanol (0.18 mL, 2.3 mmol) and DIAD (0.45 mL, 2.3 mmol). The resulting suspension was heated to 50° C., and then cooled to rt. The reaction mixture was filtered through a plug of Celite™. The filtrate was diluted with EtOAc, and the organic layer was washed with 1:1 brine/water, dried over $MgSO_4$, filtered, and concentrated to dryness in vacuo to afford crude 1-cyclobutyl-3-methyl-4-nitro-1H-pyrazole. MS (ESI) m/z $C_8H_{12}N_3O_2$ $[M+H]^+$ calc'd 182. found 182.

Step 2: To crude 1-cyclobutyl-3-methyl-4-nitro-1H-pyrazole was added THF (4 mL), 10 wt % Pd/C (164 mg, 0.15 mmol) and MeOH (4 mL). The resulting suspension was put under an atmosphere of $H_2$ and was stirred at rt overnight. The reaction mixture was filtered through a plug of Celite™, and the filtrate was concentrated to dryness in vacuo to afford 1-cyclobutyl-3-methyl-1H-pyrazol-4-amine, which was used without further purification. MS (ESI) m/z $C_8H_{14}N_3$ $[M+H]^+$ calc'd 152. found 152.

Intermediates in Table 2 below were prepared using procedures analogous to those described in Scheme 3.

TABLE 2

| Intermediate | Structure | Name | Exact Mass $[M + H]^+$ |
| --- | --- | --- | --- |
| 6 | 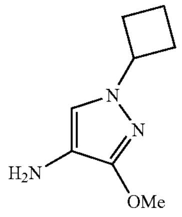 [SMILES: COc1nn(C2CCC2)cc1N] | 1-cyclobutyl-3-methoxy-1H-pyrazol-4-amine | calc'd 168, found 168 |
| 7 | 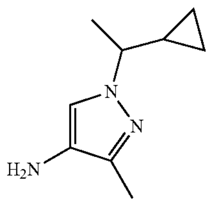 | 1-(1-cyclopropylethyl)-3-methyl-1H-pyrazol-4-amine | calc'd 166, found 166 |
| 8 | 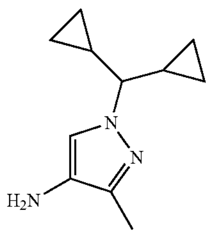 | 1-(dicyclopropylmethyl)-3-methyl-1H-pyrazol-4-amine | calc'd 192, found 192 |

Scheme 4. Synthesis of 1-((3,3-difluorocyclobutyl)methyl)-1H-pyrazol-4-amine

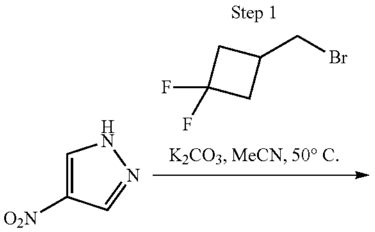

-continued

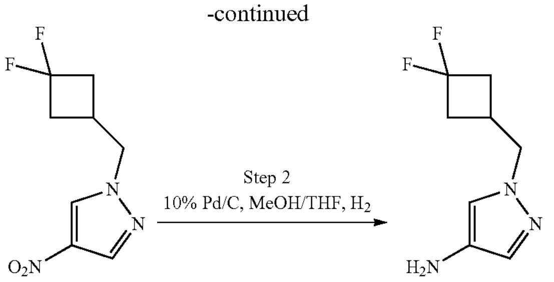

1-((3,3-Difluorocyclobutyl)methyl)-1H-pyrazol-4-amine (Intermediate 9)

Step 1: To a mixture of 4-nitro-1H-pyrazole (53 mg, 0.47 mmol), $K_2CO_3$ (130 mg, 0.94 mmol), and MeCN (2.4 mL) was added 3-(bromomethyl)-1,1-difluorocyclobutane (130 mg, 0.71 mmol). The resulting suspension was heated to 50° C., and then cooled to rt. The reaction mixture was vacuum filtered through a plug of Celite™, and the filtrate was concentrated to dryness in vacuo to afford crude 1-((3,3-difluorocyclobutyl)methyl)-4-nitro-1H-pyrazole. MS (ESI) m/z $C_8H_{10}F_2N_3O_2$ $[M+H]^+$ calc'd 218. found 218.

Step 2: To crude 1-((3,3-difluorocyclobutyl)methyl)-4-nitro-1H-pyrazole was added THF (2 mL), 10 wt % Pd/C (50 mg, 0.047 mmol), and MeOH (2 mL). The resulting suspension was put under an atmosphere of $H_2$ and was stirred at rt overnight. The reaction mixture was filtered through a plug of Celite™, and the filtrate was concentrated to dryness in vacuo to afford 1-((3,3-difluorocyclobutyl)methyl)-1H-pyrazol-4-amine, which was used without further purification. MS (ESI) m/z $C_8H_{12}F_2N_3$ $[M+H]^+$ calc'd 188. found 188.

Intermediates in Table 3 below were prepared using procedures analogous to those described in Scheme 4.

TABLE 3

| Intermediate | Structure | Name | Exact Mass $[M + H]^+$ |
|---|---|---|---|
| 10 | 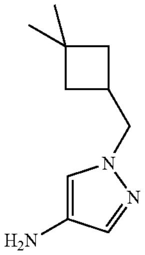 | 1-((3,3-dimethylcyclobutyl)methyl)-1H-pyrazol-4-amine | calc'd 180, found 180 |
| 11 | 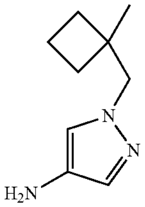 | 1-((1-methylcyclobutyl)methyl)-1H-pyrazol-4-amine | calc'd 166, found 166 |
| 12 | 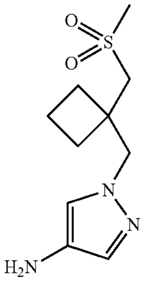 [SMILES: CS(=O)(=O)CC1(Cn2cc(N)cn2)CCC1] | 1-((1-((methylsulfonyl)methyl)cyclobutyl)methyl)-1H-pyrazol-4-amine | calc'd 244, found 244 |
| 13 | 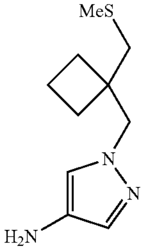 [SMILES: CSCC1(Cn2cc(N)cn2)CCC1] | 1-((1-((methylthio)methyl)cyclobutyl)methyl)-1H-pyrazol-4-amine | calc'd 212, found 212 |
| 14 | 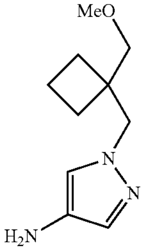 [SMILES: COCC1(Cn2cc(N)cn2)CCC1] | 1-((1-(methoxymethyl)cyclobutyl)methyl)-1H-pyrazol-4-amine | calc'd 196, found 196 |

TABLE 3-continued

| Intermediate | Structure | Name | Exact Mass $[M + H]^+$ |
|---|---|---|---|
| 15 | 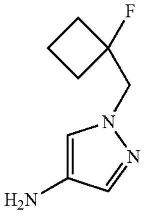 [SMILES: Nc1cnn(CC2(F)CCC2)c1] | 1-((1-fluorocyclobutyl)methyl)-1H-pyrazol-4-amine | calc'd 170, found 170 |

Scheme 5. Synthesis of 2-(1-((2-(trimethylsilyl)ethoxy)methyl)-1H-pyrazol-4-yl)thiazole-4-carboxylic acid

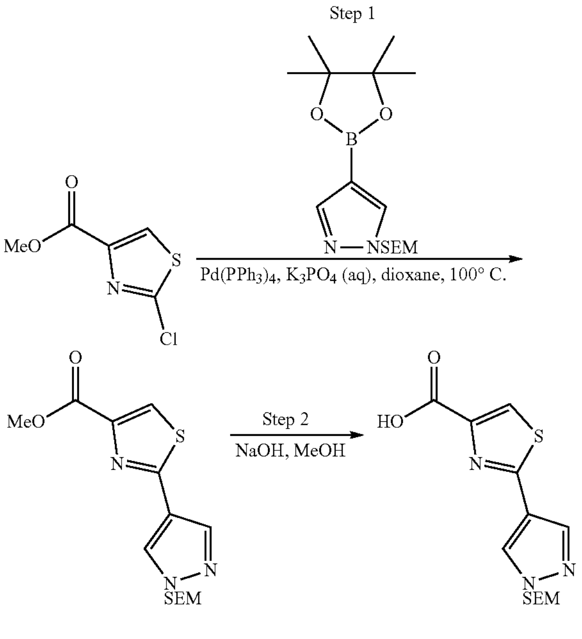

2-(1-((2-(Trimethylsilyl)ethoxy)methyl)-1H-pyrazol-4-yl)thiazole-4-carboxylic acid (Intermediate 16)

Step 1: A stock solution of methyl 2-chlorothiazole-4-carboxylate (17.7 g, 100 mmol) in dioxane (400 mL) was prepared. To a mixture of $Pd(PPh_3)_4$ (11.5 g, 9.97 mmol), 4-(4,4,5,5-tetramethyl-1,3,2-dioxaborolan-2-yl)-1-((2-(trimethylsilyl)ethoxy)methyl)-1H-pyrazole (35.6 g, 110 mmol), and aqueous $K_3PO_4$ (33.0 mL, 1.2 M in water, 399 mmol) was added the aforementioned stock solution portionwise. The reaction vessel was purged thrice with nitrogen and heated to 100° C. for 6 h, and then cooled to rt. The reaction mixture was concentrated to dryness in vacuo. The residue was re-dissolved in $CH_2Cl_2$, and the organic layer was washed with brine, dried over $Na_2SO_4$, filtered, and concentrated to dryness in vacuo. The crude residue was purified by silica gel chromatography (eluent: 0-30% EtOAc/petroleum ether) to afford methyl 2-(1-((2-(trimethylsilyl)ethoxy)methyl)-1H-pyrazol-4-yl)thiazole-4-carboxylate. MS (ESI) m/z $C_{14}H_{22}N_3O_3SSi$ $[M+H]^+$ calc'd 340. found 340. $^1H$ NMR (400 MHz, $CDCl_3$) δ 8.16 (d, J=0.7 Hz, 1H), 8.08 (s, 1H), 8.00 (d, J=0.7 Hz, 1H), 5.45 (s, 2H), 3.96 (s, 3H), 3.61-3.55 (m, 2H), 1.00-0.84 (m, 2H), −0.03 (s, 9H).

Step 2: To methyl 2-(1-((2-(trimethylsilyl)ethoxy)methyl)-1H-pyrazol-4-yl)thiazole-4-carboxylate (7.00 g, 20.6 mmol) was added MeOH (50 mL) and aqueous NaOH (20.6 mL, 2 M in water, 41.2 mmol). The resulting solution was stirred at rt for 16 h. The reaction mixture was concentrated to dryness in vacuo. The residue was re-dissolved in water, and the aqueous layer was extracted with EtOAc. The aqueous layer was acidified until pH 4, at which point precipitate was observed. The suspension was filtered, and the filter cake was washed thrice with water, and dried in vacuo to afford 2-(1-((2-(trimethylsilyl)ethoxy)methyl)-1H-pyrazol-4-yl)thiazole-4-carboxylic acid. MS (ESI) m/z $C_{13}H_{20}N_3O_3SSi$ $[M+H]^+$ calc'd 326. found 326. $^1H$ NMR (400 MHz, DMSO-$d_6$) δ 13.02 (s, 1H), 8.59 (d, J=0.8 Hz, 1H), 8.34 (s, 1H), 8.05 (d, J=0.7 Hz, 1H), 5.45 (s, 2H), 3.57 (dd, J=8.6, 7.5 Hz, 2H), 0.88-0.79 (m, 2H), −0.06 (s, 9H).

Intermediates in Table 4 below were prepared using procedures analogous to those described in Scheme 5.

TABLE 4

| Intermediate | Structure | Name | Exact Mass [M + H]+ |
|---|---|---|---|
| 17 | 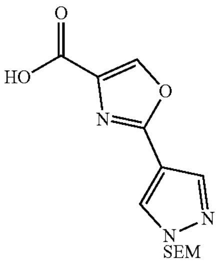 [SMILES: C[Si](C)(C)CCOCn1cc(-c2nc(C(=O)O)co2)cn1] | 2-(1-((2-(trimethylsilyl)ethoxy)methyl)-1H-pyrazol-4-yl)oxazole-4-carboxylic acid | calc'd 310, found 310 |

Scheme 6. Synthesis of 2-(1H-pyrazol-4-yl)thiazole-4-carboxylic acid

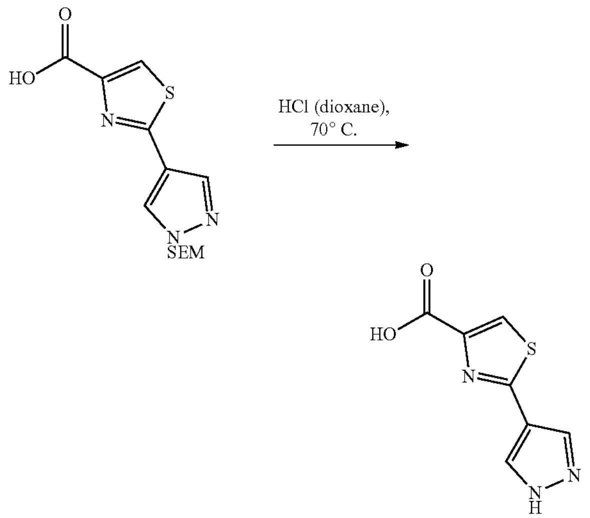

2-(1H-Pyrazol-4-yl)thiazole-4-carboxylic acid (Intermediate 18)

To 2-(1-((2-(trimethylsilyl)ethoxy)methyl)-1H-pyrazol-4-yl)thiazole-4-carboxylic acid (Intermediate 16, 1.0 g, 3.1 mmol) was added HCl (10 mL, 4 N in dioxane, 40 mmol). The reaction mixture was stirred at 70° C. for 1 h, and then cooled to rt. The suspension was filtered, and the filter cake was washed with petroleum ether, and dried in vacuo to afford 2-(1H-pyrazol-4-yl)thiazole-4-carboxylic acid, which was used without further purification. MS (ESI) m/z $C_7H_6N_3O_2S$ $[M+H]^+$ calc'd 196. found 196. $^1H$ NMR (300 MHz, DMSO-$d_6$) δ 8.27 (s, 1H), 8.17 (s, 2H).

Scheme 7. Synthesis of 6-(1-(2,2,2-trifluoroethyl)-1H-pyrazol-4-yl)picolinic acid

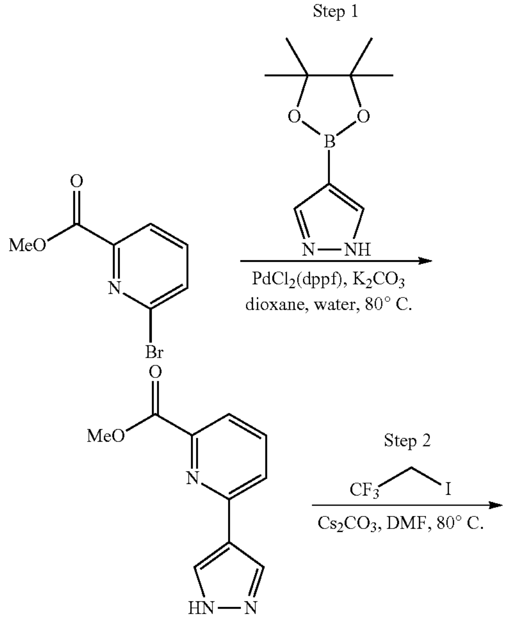

-continued

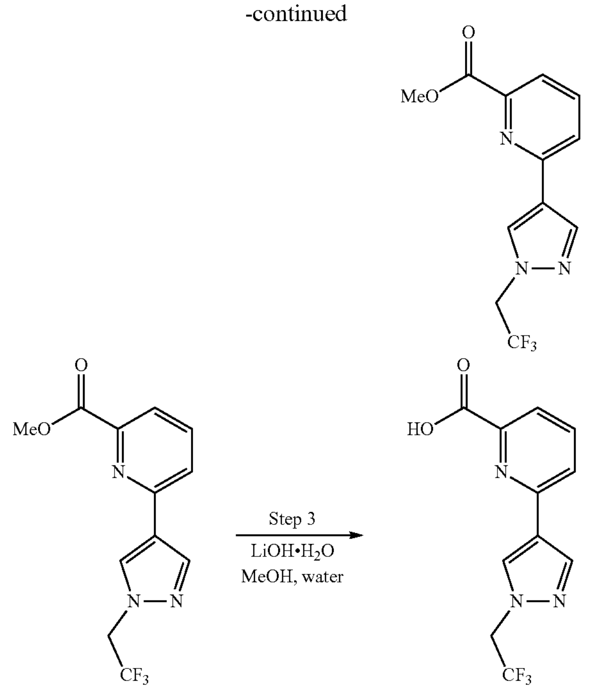

6-(1-(2,2,2-Trifluoroethyl)-1H-pyrazol-4-yl)picolinic acid (Intermediate 19)

Step 1: To a mixture of methyl 6-bromopicolinate (8.00 g, 37.0 mmol), $PdCl_2$(dppf) (1.36 g, 1.85 mmol), 4-(4,4,5,5-tetramethyl-1,3,2-dioxaborolan-2-yl)-1H-pyrazole (8.62 g, 44.4 mmol), $K_2CO_3$ (15.4 g, 111 mmol), and dioxane (100 mL) was added water (20 mL). The reaction vessel was purged with nitrogen and heated to 80° C. overnight, and then cooled to rt, at which point EtOAc and water were added. The phases were separated, and the aqueous layer was extracted twice with EtOAc. The combined organic layers were washed with brine, dried over $Na_2SO_4$, filtered, and concentrated to dryness in vacuo. The crude residue was purified by silica gel chromatography (eluent: 0-50% EtOAc/petroleum ether) to afford methyl 6-(1H-pyrazol-4-yl)picolinate. MS (ESI) m/z $C_{10}H_{10}N_3O_2$ $[M+H]^+$ calc'd 204. found 204. $^1H$ NMR (400 MHz, $CDCl_3$) δ 8.19 (s, 2H), 7.95 (d, J=7.8 Hz, 1H), 7.83 (t, J=7.7 Hz, 1H), 7.68 (dd, J=0.9, 7.9 Hz, 1H), 4.01 (s, 2H).

Step 2: To methyl 6-(1H-pyrazol-4-yl)picolinate (50 mg, 0.25 mmol) were added sequentially DMF (2 mL), 1,1,1-trifluoro-2-iodoethane (258 mg, 1.23 mmol), and then $Cs_2CO_3$ (241 mg, 0.74 mmol). The resulting suspension was heated to 80° C. overnight, and then cooled to rt. The reaction mixture was poured into water and diluted with EtOAc. The layers were separated, and the aqueous layer was extracted thrice with EtOAc. The combined organic layers were dried over $Na_2SO_4$, filtered, and concentrated to dryness in vacuo. The crude residue was purified by preparative TLC (eluent: 33% EtOAc/petroleum ether) to afford 6-(1-(2,2,2-trifluoroethyl)-1H-pyrazol-4-yl)picolinate. MS (ESI) m/z $C_{12}H_{11}F_3N_3O_2$ $[M+H]^+$ calc'd 286. found 286.

Step 3: A stock solution of lithium hydroxide hydrate (36.8 mg, 0.88 mmol) in water (1 mL) was prepared. To 6-(1-(2,2,2-trifluoroethyl)-1H-pyrazol-4-yl)picolinate (50 mg, 0.175 mmol) was added MeOH (1 mL) and the aforementioned stock solution. The resulting solution was stirred at rt for 6 h. The reaction mixture was poured into ice water and acidified with HCl (2 N in water) until pH 2-3. The aqueous layer was extracted thrice with $CH_2Cl_2$. The combined organic layers were dried over $Na_2SO_4$, filtered, and concentrated to dryness in vacuo to afford 6-(1-(2,2,2-trifluoroethyl)-1H-pyrazol-4-yl)picolinic acid, which was used without further purification. MS (ESI) m/z $C_{11}H_9F_3N_3O_2$ $[M+H]^+$ calc'd 272. found 272.

Scheme 8. Synthesis of N-(1H-pyrazol-4-yl)-2-(1-((2-trimethylsilyl) ethoxy)methyl)-1H-pyrazol-4-yl)thiazole-4-carboxamide

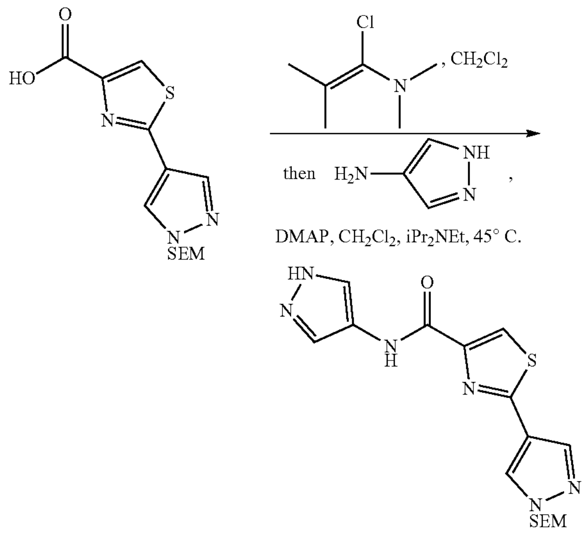

N-(1H-Pyrazol-4-yl)-2-(1-((2-(trimethylsilyl)ethoxy) methyl)-1H-pyrazol-4-yl)thiazole-4-carboxamide (Intermediate 20)

To 2-(1-((2-(trimethylsilyl)ethoxy)methyl)-1H-pyrazol-4-yl)thiazole-4-carboxylic acid (Intermediate 16, 3.50 g, 10.8 mmol) were added sequentially $CH_2Cl_2$ (40 mL) and 1-chloro-N,N,2-trimethyl-1-propenylamine (2.14 mL, 16.1 mmol). The reaction mixture was aged for 30 min, at which point 1H-pyrazol-4-amine hydrochloride (1.67 g, 14.0 mmol), $iPr_2NEt$ (7.51 mL, 43.0 mmol), and DMAP (131 mg, 1.08 mmol) were sequentially added. The reaction mixture was stirred at rt overnight, at which point water was added. The phases were separated, and the aqueous layer was extracted thrice with $CH_2Cl_2$. The combined organic layers were dried over $Na_2SO_4$, filtered, and concentrated to dryness in vacuo. The crude residue was purified by silica gel chromatography (eluent: 0-100% EtOAc/hexanes) to afford N-(1H-pyrazol-4-yl)-2-(1-((2-(trimethylsilyl)ethoxy) methyl)-1H-pyrazol-4-yl)thiazole-4-carboxamide. MS (ESI) m/z $C_{16}H_{23}N_6O_2SSi$ $[M+H]^+$ calc'd 391. found 391. $^1H$ NMR (400 MHz, $CDCl_3$) δ 9.17 (s, 1H), 8.11 (s, 1H), 8.08 (s, 1H), 8.00 (s, 1H), 8.00-7.98 (m, 2H), 5.48 (s, 2H), 3.65-3.59 (m, 2H), 0.97-0.90 (m, 2H), −0.02 (s, 9H).

Intermediates in Table 5 below were prepared from Intermediate 1 using procedures analogous to those described in Scheme 7.

TABLE 5

| Intermediate | Structure | Name | Exact Mass $[M + H]^+$ |
|---|---|---|---|
| 21 | 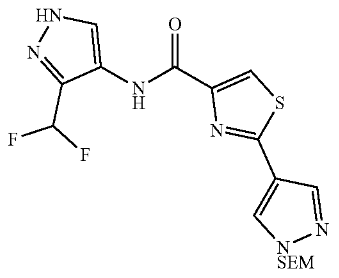 [SMILES: C[Si](C)(C)CCOCn1cc(-c2nc(C(=O)Nc3c[nH]nc3C(F)F)cs2)cn1] | N-(1H-pyrazol-4-yl)-2-(1-((2-(trimethylsilyl)ethoxy)methyl)-1H-pyrazol-4-yl)thiazole-4-carboxamide | calc'd 391, found 391 |
| 22 | 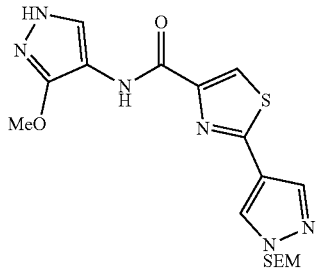 [SMILES: COc1n[nH]cc1NC(=O)c1csc(-c2cnn(COCC[Si](C)(C)C)c2)n1] | N-(3-methoxy-1H-pyrazol-4-yl)-2-(1-((2-(trimethylsilyl)ethoxy)methyl)-1H-pyrazol-4-yl)thiazole-4-carboxamide | calc'd 421, found 421 |

PREPARATIVE EXAMPLES

Preparation of Examples 1-1, 1-2, and 1-3

Scheme 9. Synthesis of N-(1-cyclobutyl-1H-pyrazol-4-yl)-2-(1H-pyrazol-4-yl)thiazole-4-carboxamide

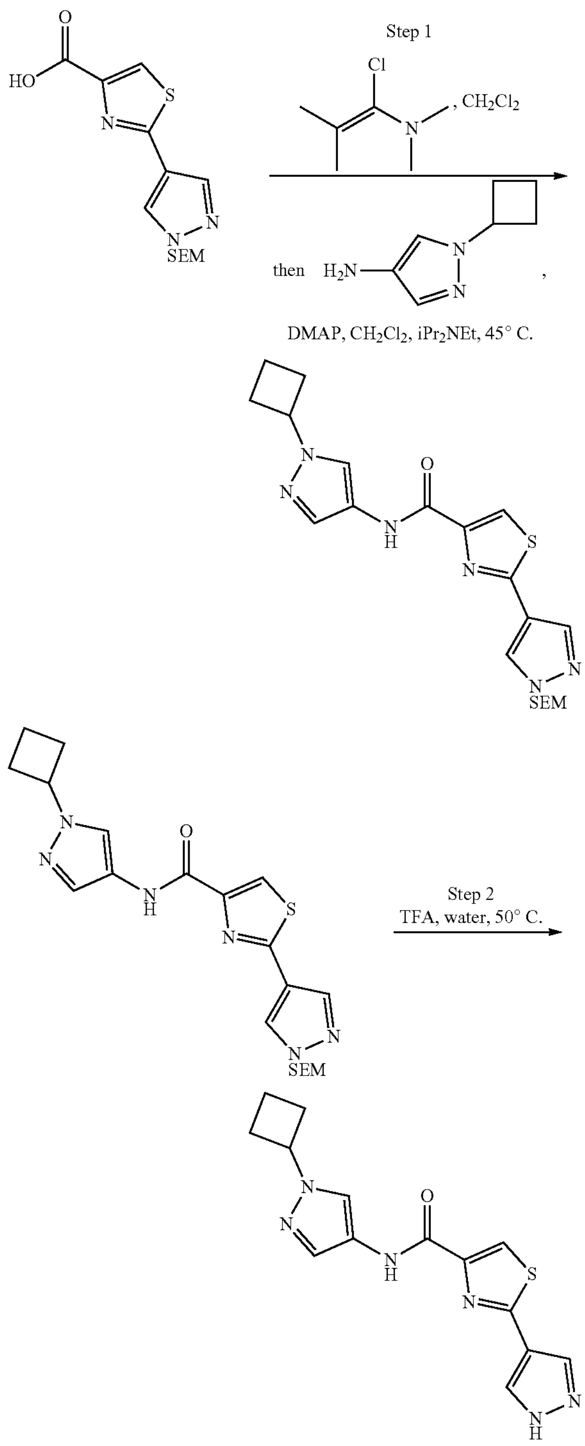

Example 1-1. N-(1-Cyclobutyl-1H-pyrazol-4-yl)-2-(1H-pyrazol-4-yl)thiazole-4-carboxamide Step 1: A stock solution containing 2-(1-((2-(trimethylsilyl)ethoxy)methyl)-1H-pyrazol-4-yl)thiazole-4-carboxylic acid (Intermediate 16, 1.04 g, 3.20 mmol), $CH_2Cl_2$ (24 mL), and 1-chloro-N,N,2-trimethyl-1-propenylamine (550 μL, 4.2 mmol) was prepared and aged for 30 min (stock solution 1). Separately, a 0.1 M stock solution of DMAP in $CH_2Cl_2$ was prepared (stock solution 2). To 1-cyclobutyl-1H-pyrazol-4-amine (20 mg, 0.15 mmol) was added 0.75 mL of stock solution 1 (0.10 mmol Intermediate 16), 0.1 mL of stock solution 2 (0.01 mmol DMAP), followed by $iPr_2NEt$ (52.4 μL, 0.30 mmol). The resulting solution was heated to 45° C. overnight, then cooled to rt. The crude solution containing N-(1-cyclobutyl-1H-pyrazol-4-yl)-2-(1-((2-(trimethylsilyl)ethoxy)methyl)-1H-pyrazol-4-yl)thiazole-4-carboxamide was carried forward without further purification. MS (ESI) m/z $C_{20}H_{29}N_6O_2SSi$ $[M+H]^+$ calc'd 445. found 445.

Step 2: To the above crude solution of N-(1-cyclobutyl-1H-pyrazol-4-yl)-2-(1-((2-(trimethylsilyl)ethoxy)methyl)-1H-pyrazol-4-yl)thiazole-4-carboxamide was added water (50 μL, 2.8 mmol) and TFA (750 μL, 9.7 mmol), and the resulting mixture was heated to 50° C. for 45 min, and then cooled to rt. The reaction mixture was concentrated to dryness in vacuo. The crude residue was re-dissolved in DMSO, filtered, and purified by preparative HPLC (reversed phase, MeCN/water with 0.1% TFA modifier) to afford N-(1-cyclobutyl-1H-pyrazol-4-yl)-2-(1H-pyrazol-4-yl)thiazole-4-carboxamide, TFA. MS (ESI) m/z $C_{14}H_{15}N_6OS$ $[M+H]^+$ calc'd 315, found 315. $^1H$ NMR (500 MHz, DMSO-$d_6$) δ 10.34 (s, 1H), 8.28 (br s, 1H), 8.21 (s, 1H), 8.11 (s, 1H), 7.73 (s, 1H), 4.82 (dt, J=16.7, 8.2 Hz, 1H), 2.48-2.41 (m, 2H), 2.41-2.33 (m, 2H), 1.83-1.71 (m, 2H).

Scheme 10. Synthesis of N-(3-methoxy-1-(2,2,2-trifluoroethyl)-1H-pyrazol-4-yl)-2-(1H-pyrazol-4-yl)thiazole-4-carboxamide

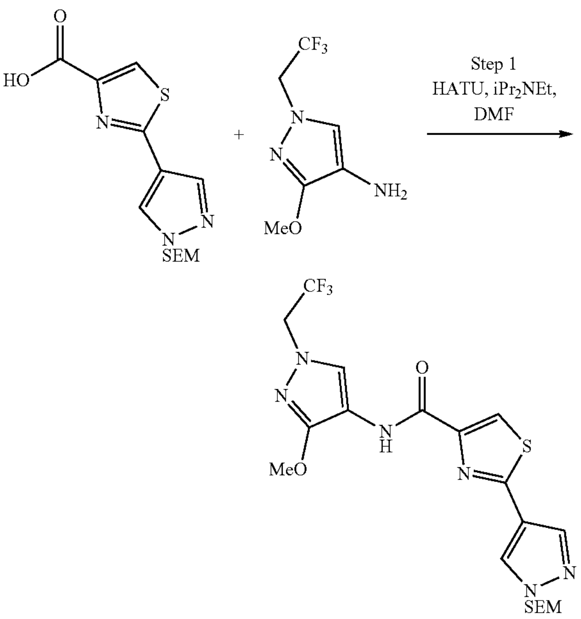

-continued

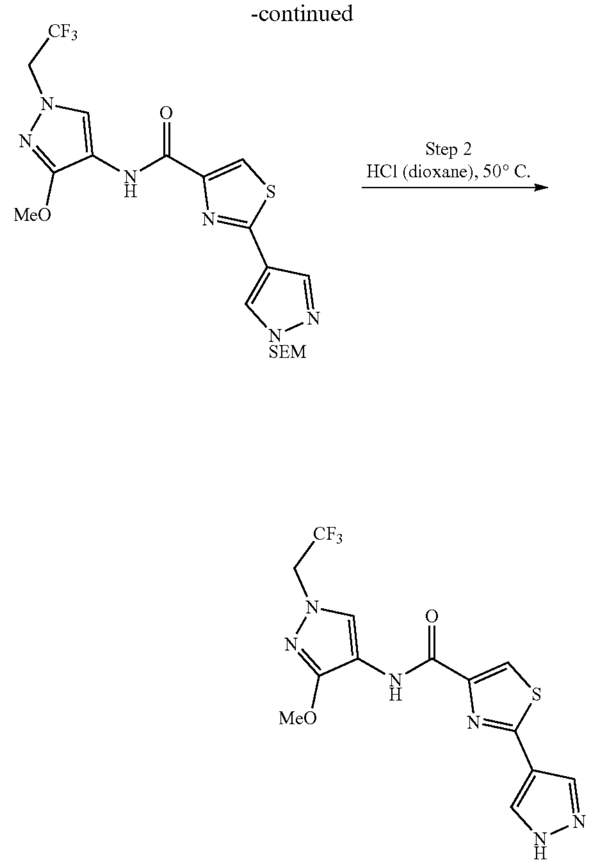

Example 1-2. N-(3-Methoxy-1-(2,2,2-trifluoro-ethyl)-1H-pyrazol-4-yl)-2-(1H-pyrazol-4-yl)thiazole-4-carboxamide Step 1: To a mixture of 2-(1-((2-(trimethylsilyl)ethoxy)methyl)-1H-pyrazol-4-yl)thiazole-4-carboxylic acid (Intermediate 16, 146 mg, 0.45 mmol), 3-methoxy-1-(2,2,2-trifluoroethyl)-1H-pyrazol-4-amine, HCl (104 mg, 0.45 mmol), HATU (171 mg, 0.45 mmol), and DMF (1.5 mL) was added $iPr_2NEt$ (0.30 mL, 1.7 mmol). The resulting mixture was stirred at rt overnight. The crude solution containing N-(3-methoxy-1-(2,2,2-trifluoroethyl)-1H-pyrazol-4-yl)-2-(1-((2-(trimethylsilyl)ethoxy)methyl)-1H-pyrazol-4-yl)thiazole-4-carboxamide was carried forward without further purification. MS (ESI) m/z $C_{19}H_{26}F_3N_6O_3SSi$ $[M+H]^+$ calc'd 503. found 503.

Step 2: To the above crude solution containing N-(3-methoxy-1-(2,2,2-trifluoroethyl)-1H-pyrazol-4-yl)-2-(1-((2-(trimethylsilyl)ethoxy)methyl)-1H-pyrazol-4-yl)thiazole-4-carboxamide was added HCl (1.5 mL, 4 N in dioxane, 6.0 mmol), and the resulting solution was heated to 50° C. overnight, and then cooled to rt. The reaction mixture was concentrated to dryness in vacuo. The crude residue was re-dissolved in 1:1 DMSO/MeOH, filtered, and purified by preparative HPLC (reversed phase, MeCN/water with 0.1% TFA modifier) to afford N-(3-methoxy-1-(2,2,2-trifluoroethyl)-1H-pyrazol-4-yl)-2-(1H-pyrazol-4-yl)thiazole-4-carboxamide, TFA. MS (ESI) m/z $C_{13}H_{12}F_3N_6O_2S$ $[M+H]^+$ calc'd 373. found 373. $^1H$ NMR (600 MHz, DMSO-$d_6$) δ 9.22 (s, 1H), 8.26 (s, 3H), 8.07 (s, 1H), 5.02-4.93 (m, 2H), 3.89 (s, 3H).

Scheme 11. Synthesis of N-(1-cyclobutyl-3-methyl-1H-pyrazol-4-yl)-2-(1H-pyrazol-4-yl)thiazole-4-carboxamide

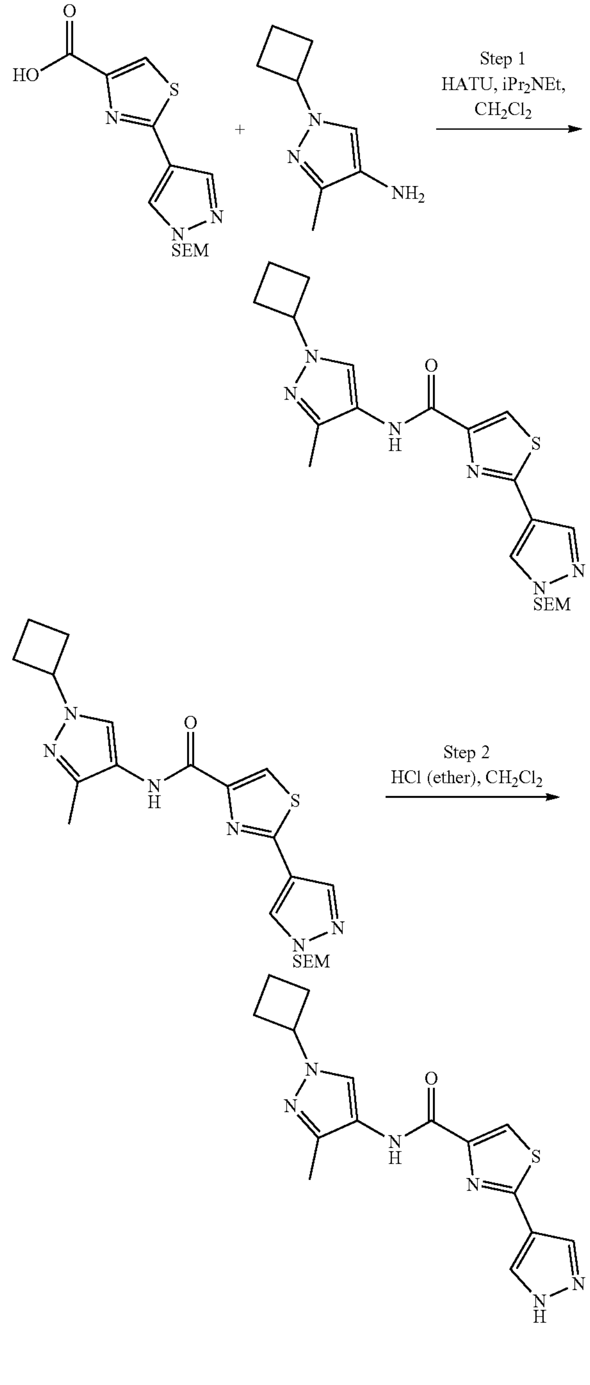

Example 1-3. N-(1-Cyclobutyl-3-methyl-1H-pyrazol-4-yl)-2-(1H-pyrazol-4-yl)thiazole-4-carboxamide Step 1: A stock solution of 1-cyclobutyl-3-methyl-1H-pyrazol-4-amine (Intermediate 5, 233 mg, 1.54 mmol) and $CH_2Cl_2$ (3 mL) was prepared. To 2-(1-((2-(trimethylsilyl)ethoxy)methyl)-1H-pyrazol-4-yl)thiazole-4-carboxylic acid (Intermediate 16, 501 mg, 1.54 mmol) were sequentially added $CH_2Cl_2$ (6 mL), $iPr_2NEt$ (0.81 mL, 4.6 mmol), the aforementioned stock solution, and then HATU (585 mg, 1.54 mmol). The reaction mixture was stirred at rt, at which point additional $CH_2Cl_2$ and water were added. The phases were separated, and the aqueous layer was extracted thrice with $CH_2C_{12}$. The combined organic layers were washed with water, dried over $MgSO_4$, filtered, and concentrated to dryness in vacuo. The crude residue was purified by silica gel chromatography (eluent: 5-40% EtOAc/$CH_2Cl_2$) to afford N-(1-cyclobutyl-3-methyl-1H-pyrazol-4-yl)-2-(1-((2-(trimethylsilyl)ethoxy)methyl)-1H-pyrazol-4-yl)thiazole-4-carboxamide. MS (ESI) m/z $C_{21}H_{31}N_6O_2SSi$ $[M+H]^+$ calc'd 459. found 459.

Step 2: To N-(1-cyclobutyl-3-methyl-1H-pyrazol-4-yl)-2-(1-((2-(trimethylsilyl)ethoxy)methyl)-1H-pyrazol-4-yl)thiazole-4-carboxamide (705 mg, 1.54 mmol) was sequentially added $CH_2Cl_2$ (1 mL), and then HCl (10 mL, 2 N in ether, 20 mmol), at which point precipitate was observed. The suspension was filtered. The residue was re-dissolved in 1:1 DMSO/MeOH, filtered, and purified by preparative HPLC (reversed phase, MeCN with 0.1% TFA modifier) to afford N-(1-cyclobutyl-3-methyl-1H-pyrazol-4-yl)-2-(1H-pyrazol-4-yl)thiazole-4-carboxamide, TFA. MS (ESI) m/z $C_{15}H_{17}N_6OS$ $[M+H]^+$ calc'd 329. found 329. $^1$H NMR (500 MHz, DMSO-$d_6$) δ 9.48 (s, 1H), 8.28 (s, 2H), 8.22 (s, 1H), 7.94 (s, 1H), 4.74 (p, J=8.2 Hz, 1H), 2.47-2.39 (m, 2H), 2.37-2.29 (m, 2H), 2.17 (s, 3H), 1.81-1.70 (m, 2H).

Compounds in Table 6 below were prepared from Intermediates 2-4, 6, and 8-17 using procedures analogous to those described in Examples 1-1, 1-2, and 1-3.

TABLE 6

| Number | Structure | Name | Exact Mass $[M + H]^+$ |
|---|---|---|---|
| 1-4 | 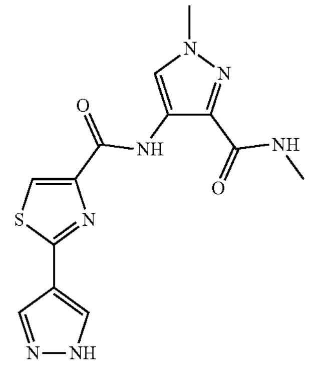 | N-[1-methyl-3-(methylcarbamoyl)-1H-pyrazol-4-yl]-2-(1H-pyrazol-4-yl)-1,3-thiazole-4-carboxamide | calc'd 332, found 332 |
| 1-5 | 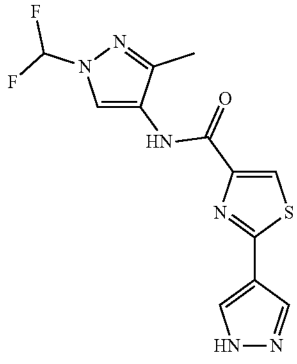 [SMILES: Cc1nn(C(F)F)cc1NC(=O)c1csc(-c2cn[nH]c2)n1] | N-[1-(difluoromethyl)-3-methyl-1H-pyrazol-4-yl]-2-(1H-pyrazol-4-yl)-1,3-thiazole-4-carboxamide | calc'd 325, found 325 |
| 1-6 | 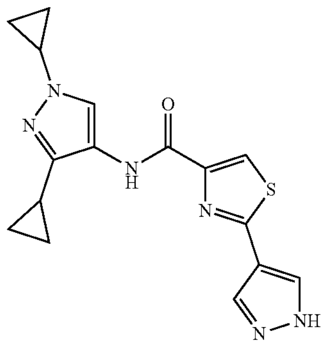 [SMILES: O=C(Nc1cn(C2CC2)nc1C1CC1)c1csc(-c2cn[nH]c2)n1] | N-(1,3-dicyclopropyl-1H-pyrazol-4-yl)-2-(1H-pyrazol-4-yl)-1,3-thiazole-4-carboxamide | calc'd 341, found 341 |

TABLE 6-continued

| Number | Structure | Name | Exact Mass [M + H]$^+$ |
| --- | --- | --- | --- |
| 1-7 | 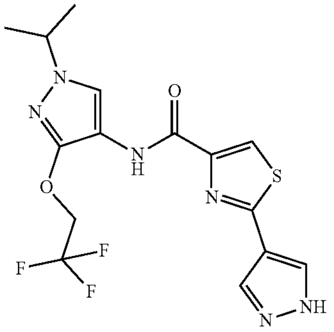 [SMILES: CC(C)n1cc(NC(=O)c2csc(-c3cn[nH]c3)n2)c(OCC(F)(F)F)n1] | N-[1-(1-methylethyl)-3-(2,2,2-trifluoroethoxy)-1H-pyrazol-4-yl]-2-(1H-pyrazol-4-yl)-1,3-thiazole-4-carboxamide | calc'd 401, found 401 |
| 1-8 | 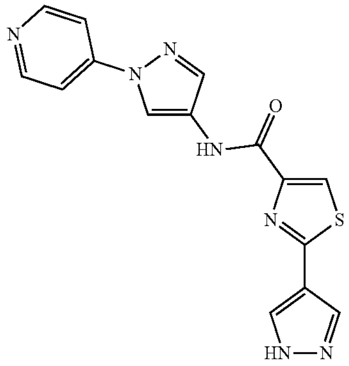 [SMILES: O=C(Nc1cnn(-c2ccncc2)c1)c1csc(-c2cn[nH]c2)n1] | 2-(1H-pyrazol-4-yl)-N-(1-pyridin-4-yl-1H-pyrazol-4-yl)-1,3-thiazole-4-carboxamide | calc'd 338, found 338 |
| 1-9 | 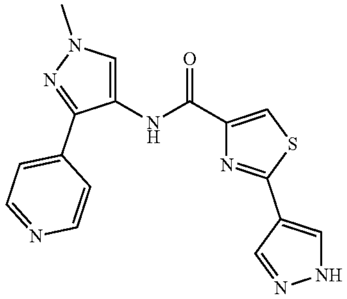 [SMILES: Cn1cc(NC(=O)c2csc(-c3cn[nH]c3)n2)c(-c2ccncc2)n1] | N-(1-methyl-3-pyridin-4-yl-1H-pyrazol-4-yl)-2-(1H-pyrazol-4-yl)-1,3-thiazole-4-carboxamide | calc'd 352, found 352 |
| 1-10 | 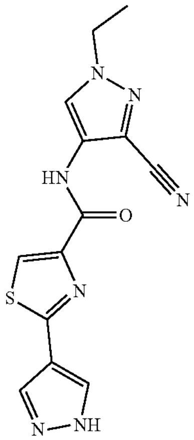 [SMILES: CCn1cc(NC(=O)c2csc(-c3cn[nH]c3)n2)c(C#N)n1] | N-(3-cyano-1-ethyl-1H-pyrazol-4-yl)-2-(1H-pyrazol-4-yl)-1,3-thiazole-4-carboxamide | calc'd 314, found 314 |

TABLE 6-continued

| Number | Structure | Name | Exact Mass [M + H]+ |
|---|---|---|---|
| 1-11 | 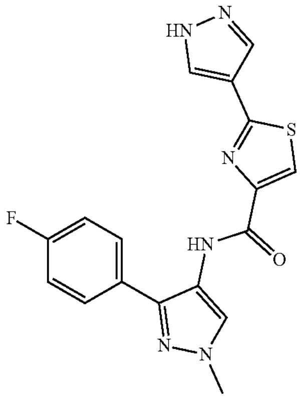 [SMILES: Cn1cc(NC(=O)c2csc(-c3cn[nH]c3)n2)c(-c2ccc(F)cc2)n1] | N-[3-(4-fluorophenyl)-1-methy1-1H-pyrazol-4-yl]-2-(1H-pyrazol-4-yl)-1,3-thiazole-4-carboxamide | calc'd 369, found 369 |
| 1-12 | 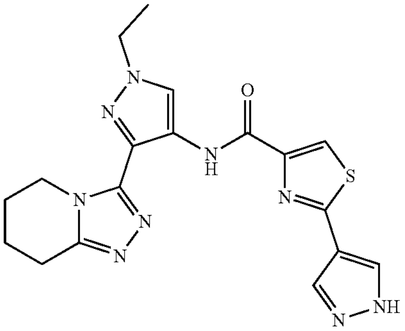 [SMILES: CCn1cc(NC(=O)c2csc(-c3cn[nH]c3)n2)c(-c2nnc3n2CCCC3)n1] | N-[1-ethyl-3-(5,6,7,8-tetrahydro[1,2,4]triazolo[4,3-a]pyridin-3-yl)-1H-pyrazol-4-yl]-2-(1H-pyrazol-4-yl)-1,3-thiazole-4-carboxamide | calc'd 410, found 410 |
| 1-13 | 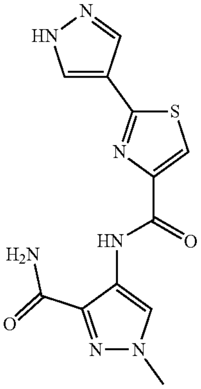 [SMILES: Cn1cc(NC(=O)c2csc(-c3cn[nH]c3)n2)c(C(N)=O)n1] | N-(3-carbamoyl-1-methyl-1H-pyrazol-4-yl)-2-(1H-pyrazol-4-yl)-1,3-thiazole-4-carboxamide | calc'd 318, found 318 |
| 1-14 | 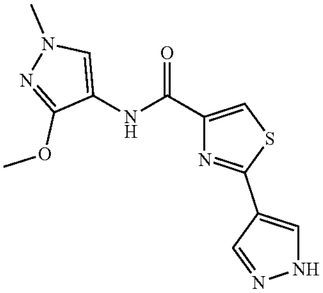 [SMILES: COc1nn(C)cc1NC(=O)c1csc(-c2cn[nH]c2)n1] | N-(3-methoxy-1-methyl-1H-pyrazol-4-yl)-2-(1H-pyrazol-4-yl)-1,3-thiazole-4-carboxamide | calc'd 305, found 305 |

TABLE 6-continued

| Number | Structure | Name | Exact Mass [M + H]$^+$ |
| --- | --- | --- | --- |
| 1-15 | 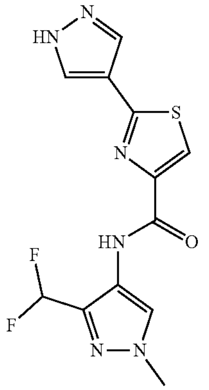 [SMILES: Cn1cc(NC(=O)c2csc(-c3cn[nH]c3)n2)c(C(F)F)n1] | N-[3-(difluoromethyl)-1-methyl-1H-pyrazol-4-yl]-2-(1H-pyrazol-4-yl)-1,3-thiazole-4-carboxamide | calc'd 325, found 325 |
| 1-16 | 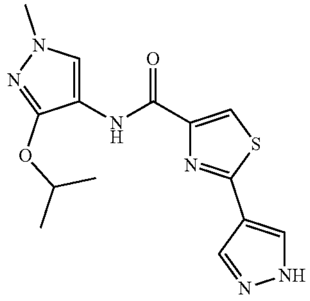 [SMILES: CC(C)Oc1nn(C)cc1NC(=O)c1csc(-c2cn[nH]c2)n1] | N-[1-methyl-3-(1-methylethoxy)-1H-pyrazol-4-yl]-2-(1H-pyrazol-4-yl)-1,3-thiazole-4-carboxamide | calc'd 333, found 333 |
| 1-17 | 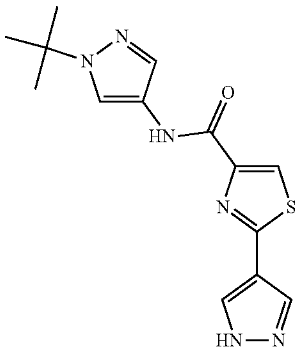 [SMILES: CC(C)(C)n1cc(NC(=O)c2csc(-c3cn[nH]c3)n2)cn1] | N-(1-tert-butyl-1H-pyrazol-4-yl)-2-(1H-pyrazol-4-yl)-1,3-thiazole-4-carboxamide | calc'd 317, found 317 |
| 1-18 | 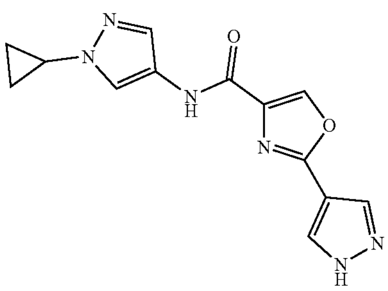 [SMILES: O=C(Nc1cnn(C2CC2)c1)c1coc(-c2cn[nH]c2)n1] | N-(1-cyclopropyl-1H-pyrazol-4-yl)-2-(1H-pyrazol-4-yl)-1,3-oxazole-4-carboxamide | calc'd 285, found 285 |

TABLE 6-continued

| Number | Structure | Name | Exact Mass [M + H]+ |
|---|---|---|---|
| 1-19 | 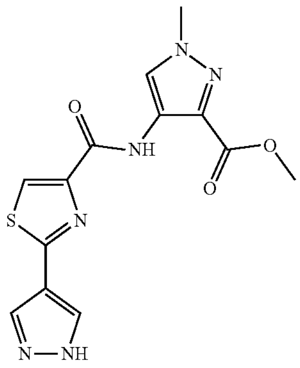 [SMILES: COC(=O)c1nn(C)cc1NC(=O)c1csc(-c2cn[nH]c2)n1] | methyl 1-methyl-4-({[2-(1H-pyrazol-4-yl)-1,3-thiazol-4-yl]carbonyl}amino)-1H-pyrazole-3-carboxylate | calc'd 333, found 333 |
| 1-20 | 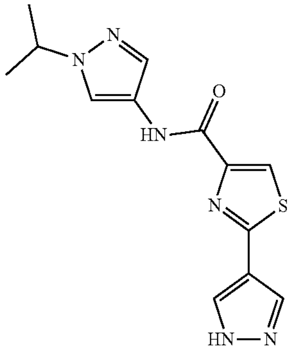 [SMILES: CC(C)n1cc(NC(=O)c2csc(-c3cn[nH]c3)n2)cn1] | N-[1-(1-methylethyl)-1H-pyrazol-4-yl]-2-(1H-pyrazol-4-yl)-1,3-thiazole-4-carboxamide | calc'd 303, found 303 |
| 1-21 | 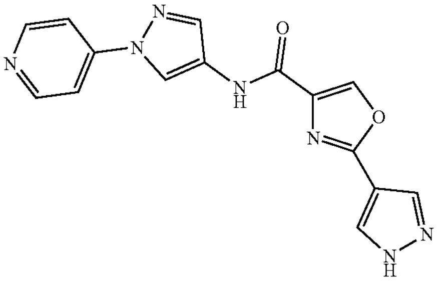 [SMILES: O=C(Nc1cnn(-c2ccncc2)c1)c1coc(-c2cn[nH]c2)n1] | 2-(1H-pyrazol-4-yl)-N-(1-pyridin-4-yl-1H-pyrazol-4-yl)-1,3-oxazole-4-carboxamide | calc'd 322, found 322 |
| 1-22 | 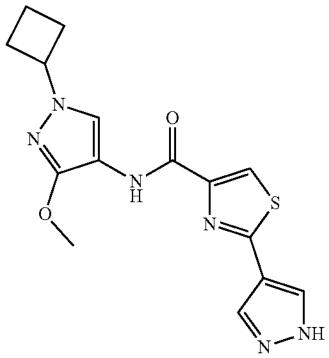 [SMILES: COc1nn(C2CCC2)cc1NC(=O)c1csc(-c2cn[nH]c2)n1] | N-(1-cyclobutyl-3-methoxy-1H-pyrazol-4-yl)-2-(1H-pyrazol-4-yl)-1,3-thiazole-4-carboxamide | calc'd 345, found 345 |

TABLE 6-continued

| Number | Structure | Name | Exact Mass [M + H]$^+$ |
| --- | --- | --- | --- |
| 1-23 | 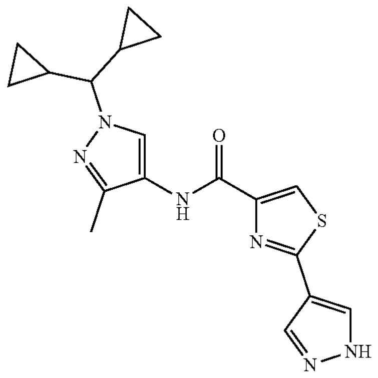 [SMILES: Cc1nn(C(C2CC2)C2CC2)cc1NC(=O)c1csc(-c2cn[nH]c2)n1] | N-[1-(dicyclopropyl-methyl)-3-methyl-1H-pyrazol-4-yl]-2-(1H-pyrazol-4-yl)-1,3-thiazole-4-carboxamide | calc'd 369, found 369 |
| 1-24 | 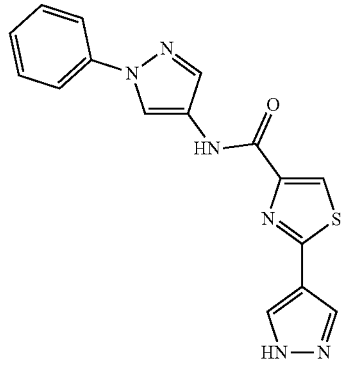 [SMILES: O=C(Nc1cnn(-c2ccccc2)c1)c1csc(-c2cn[nH]c2)n1] | N-(1-phenyl-1H-pyrazol-4-yl)-2-(1H-pyrazol-4-yl)-1,3-thiazole-4-carboxamide | calc'd 337, found 337 |
| 1-25 | 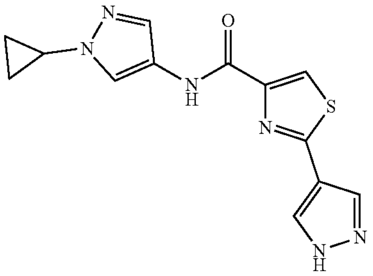 [SMILES: O=C(Nc1cnn(C2CC2)c1)c1csc(-c2cn[nH]c2)n1] | N-(1-cyclopropyl-1H-pyrazol-4-yl)-2-(1H-pyrazol-4-yl)-1,3-thiazole-4-carboxamide | calc'd 301, found 301 |
| 1-26 | 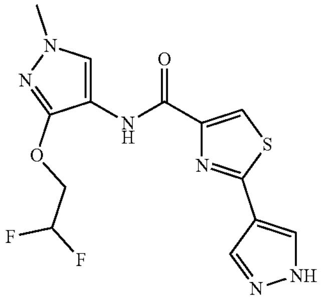 [SMILES: Cn1cc(NC(=O)c2csc(-c3cn[nH]c3)n2)c(OCC(F)F)n1] | N-[3-(2,2-difluoroethoxy)-1-methyl-1H-pyrazol-4-yl]-2-(1H-pyrazol-4-yl)-1,3-thiazole-4-carboxamide | calc'd 355, found 355 |

TABLE 6-continued

| Number | Structure | Name | Exact Mass [M + H]$^+$ |
|---|---|---|---|
| 1-27 | 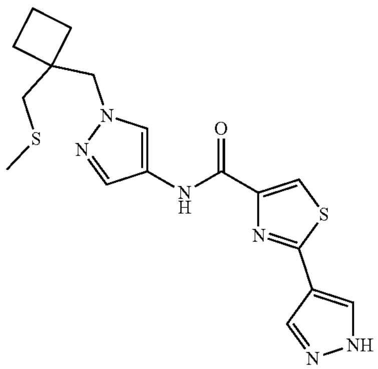 [SMILES: CSCC1(Cn2cc(NC(=O)c3csc(-c4cn[nH]c4)n3)cn2)CCC1] | N-[1-({1-[(methylsulfanyl)methyl]cyclobutyl}methyl)-1H-pyrazol-4-yl]-2-(1H-pyrazol-4-yl)-1,3-thiazole-4-carboxamide | calc'd 389, found 389 |
| 1-28 | 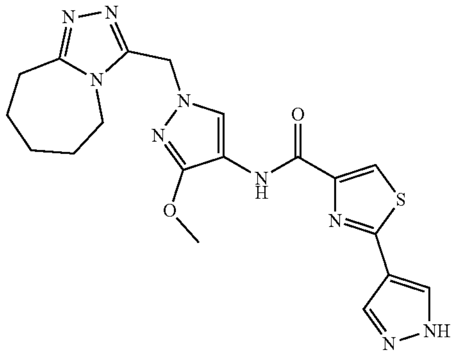 [SMILES: COc1nn(Cc2nnc3n2CCCCC3)cc1NC(=O)c1csc(-c2cn[nH]c2)n1] | N-[3-methoxy-1-(6,7,8,9-tetrahydro-5H-[1,2,4]triazolo[4,3-a]azepin-3-ylmethyl)-1H-pyrazol-4-yl]-2-(1H-pyrazol-4-yl)-1,3-thiazole-4-carboxamide | calc'd 440, found 440 |
| 1-29 | 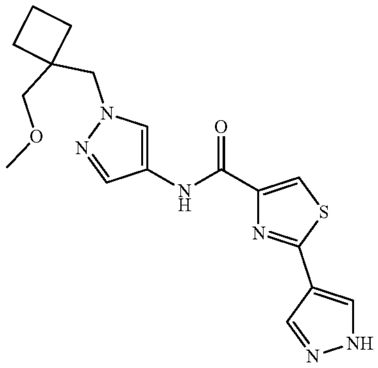 [SMILES: COCC1(Cn2cc(NC(=O)c3csc(-c4cn[nH]c4)n3)cn2)CCC1] | N-(1-{[1-(methoxymethyl)cyclobutyl]methyl}-1H-pyrazol-4-yl)-2-(1H-pyrazol-4-yl)-1,3-thiazole-4-carboxamide | calc'd 373, found 373 |
| 1-30 | 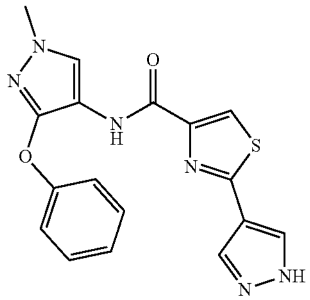 [SMILES: Cn1cc(NC(=O)c2csc(-c3cn[nH]c3)n2)c(Oc2ccccc2)n1] | N-(1-methyl-3-phenoxy-1H-pyrazol-4-yl)-2-(1H-pyrazol-4-yl)-1,3-thiazole-4-carboxamide | calc'd 367, found 367 |

TABLE 6-continued

| Number | Structure | Name | Exact Mass [M + H]+ |
|---|---|---|---|
| 1-31 | 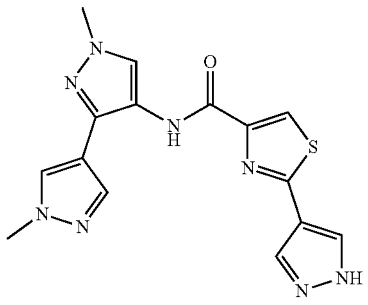 [SMILES: Cn1cc(-c2nn(C)cc2NC(=O)c2csc(-c3cn[nH]c3)n2)cn1] | N-(1,1'-dimethyl-1H,1'H-3,4'-bipyrazol-4-yl)-2-(1H-pyrazol-4-yl)-1,3-thiazole-4-carboxamide | calc'd 355, found 355 |
| 1-32 | 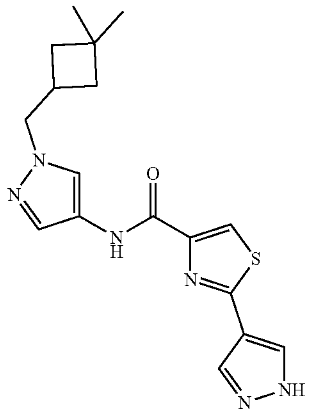 [SMILES: CC1(C)CC(Cn2cc(NC(=O)c3csc(-c4cn[nH]c4)n3)cn2)C1] | N-{1-[(3,3-dimethylcyclobutyl)methyl]-1H-pyrazol-4-yl}-2-(1H-pyrazol-4-yl)-1,3-thiazole-4-carboxamide | calc'd 357, found 357 |
| 1-33 | 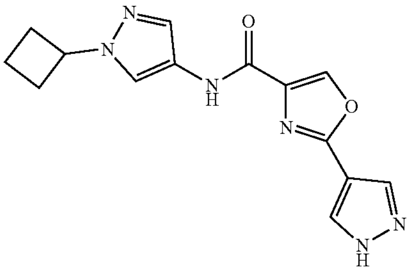 [SMILES: O=C(Nc1cnn(C2CCC2)c1)c1coc(-c2cn[nH]c2)n1] | N-(1-cyclobutyl-1H-pyrazol-4-yl)-2-(1H-pyrazol-4-yl)-1,3-oxazole-4-carboxamide | calc'd 299, found 299 |
| 1-34 | 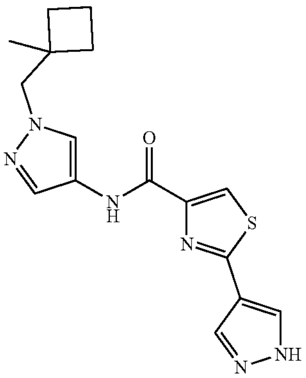 [SMILES: CC1(Cn2cc(NC(=O)c3csc(-c4cn[nH]c4)n3)cn2)CCC1] | N-{1-[(1-methylcyclobutyl)methyl]-1H-pyrazol-4-yl}-2-(1H-pyrazol-4-yl)-1,3-thiazole-4-carboxamide | calc'd 343, found 343 |

TABLE 6-continued

| Number | Structure | Name | Exact Mass [M + H]$^+$ |
|---|---|---|---|
| 1-35 | 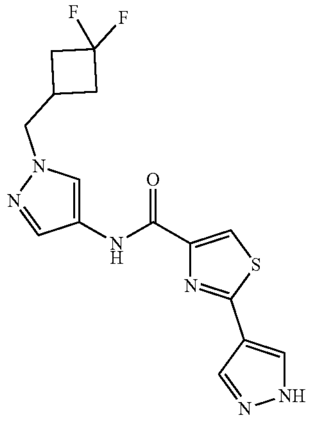 [SMILES: O=C(Nc1cnn(CC2CC(F)(F)C2)c1)c1csc(-c2cn[nH]c2)n1] | N-{1-[(3,3-difluorocyclobutyl)methyl]-1H-pyrazol-4-yl}-2-(1H-pyrazol-4-yl)-1,3-thiazole-4-carboxamide | calc'd 365, found 365 |
| 1-36 | 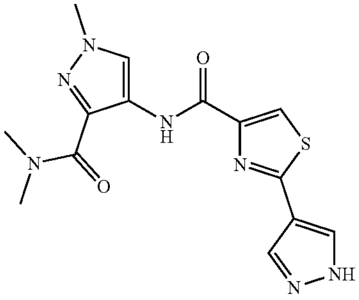 [SMILES: CN(C)C(=O)c1nn(C)cc1NC(=O)c1csc(-c2cn[nH]c2)n1] | N-[3-(dimethylcarbamoyl)-1-methyl-1H-pyrazol-4-yl]-2-(1H-pyrazol-4-yl)-1,3-thiazole-4-carboxamide | calc'd 346, found 346 |
| 1-37 | 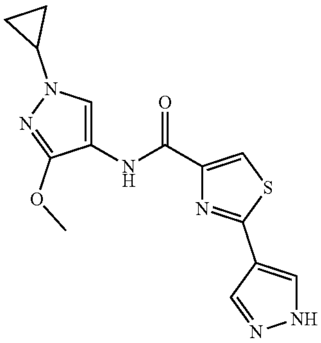 [SMILES: COc1nn(C2CC2)cc1NC(=O)c1csc(-c2cn[nH]c2)n1] | N-(1-cyclopropyl-3-methoxy-1H-pyrazol-4-yl)-2-(1H-pyrazol-4-yl)-1,3-thiazole-4-carboxamide | calc'd 331, found 331 |
| 1-38 | 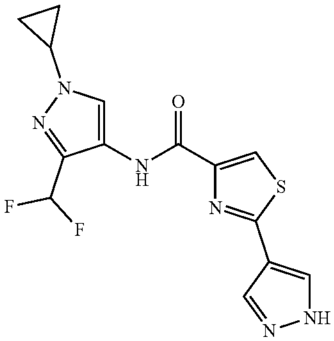 [SMILES: O=C(Nc1cn(C2CC2)nc1C(F)F)c1csc(-c2cn[nH]c2)n1] | N-[1-cyclopropyl-3-(difluoromethyl)-1H-pyrazol-4-yl]-2-(1H-pyrazol-4-yl)-1,3-thiazole-4-carboxamide | calc'd 351, found 351 |

TABLE 6-continued

| Number | Structure | Name | Exact Mass [M + H]$^+$ |
|---|---|---|---|
| 1-39 | 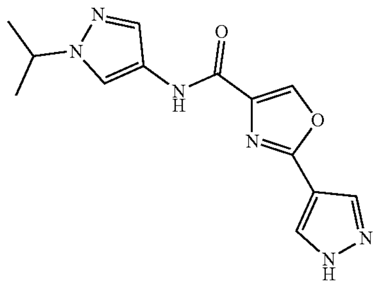 [SMILES: CC(C)n1cc(NC(=O)c2coc(-c3cn[nH]c3)n2)cn1] | N-[1-(1-methylethyl)-1H-pyrazol-4-yl]-2-(1H-pyrazol-4-yl)-1,3-oxazole-4-carboxamide | calc'd 287, found 287 |
| 1-40 | 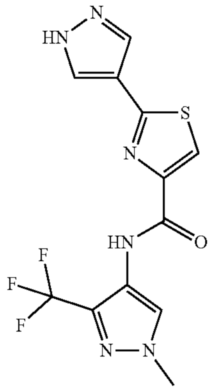 [SMILES: Cn1cc(NC(=O)c2csc(-c3cn[nH]c3)n2)c(C(F)(F)F)n1] | N-[1-methyl-3-(trifluoromethyl)-1H-pyrazol-4-yl]-2-(1H-pyrazol-4-yl)-1,3-thiazole-4-carboxamide | calc'd 343, found 343 |
| 1-41 | 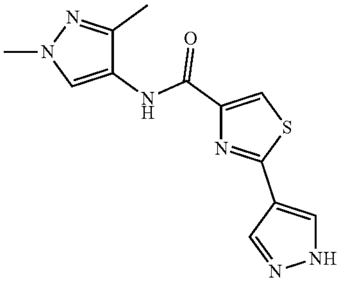 [SMILES: Cc1nn(C)cc1NC(=O)c1csc(-c2cn[nH]c2)n1] | N-(1,3-dimethyl-1H-pyrazol-4-yl)-2-(1H-pyrazol-4-yl)-1,3-thiazole-4-carboxamide | calc'd 289, found 289 |
| 1-42 | 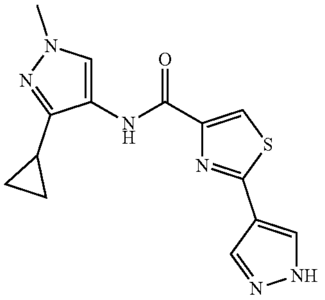 [SMILES: Cn1cc(NC(=O)c2csc(-c3cn[nH]c3)n2)c(C2CC2)n1] | N-(3-cyclopropyl-1-methyl-1H-pyrazol-4-yl)-2-(1H-pyrazol-4-yl)-1,3-thiazole-4-carboxamide | calc'd 315, found 315 |

TABLE 6-continued

| Number | Structure | Name | Exact Mass [M + H]+ |
|---|---|---|---|
| 1-43 | 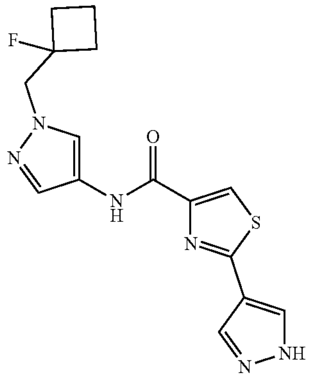 [SMILES: O=C(Nc1cnn(CC2(F)CCC2)c1)c1csc(-c2cn[nH]c2)n1] | N-{1-[(1-fluorocyclobutyl)methyl]-1H-pyrazol-4-yl}-2-(1H-pyrazol-4-yl)-1,3-thiazole-4-carboxamide | calc'd 347, found 347 |
| 1-44 | 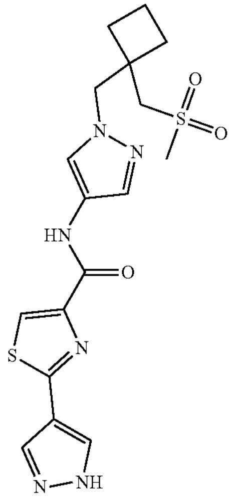 [SMILES: CS(=O)(=O)CC1(Cn2cc(NC(=O)c3csc(-c4cn[nH]c4)n3)cn2)CCC1] | N-[1-({1-[(methylsulfonyl)methyl]cyclobutyl}methyl)-1H-pyrazol-4-yl]-2-(1H-pyrazol-4-yl)-1,3-thiazole-4-carboxamide | calc'd 421, found 421 |
| 1-45 | 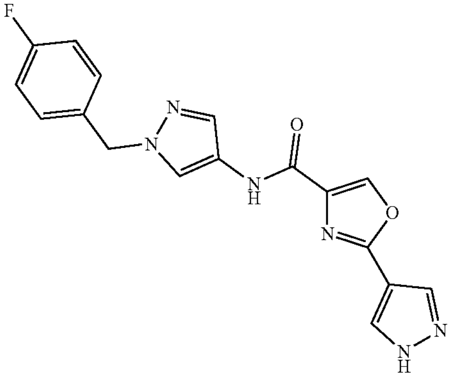 [SMILES: O=C(Nc1cnn(Cc2ccc(F)cc2)c1)c1coc(-c2cn[nH]c2)n1] | N-[1-(4-fluorobenzyl)-1H-pyrazol-4-yl]-2-(1H-pyrazol-4-yl)-1,3-oxazole-4-carboxamide | calc'd 353, found 353 |
| 1-46 | 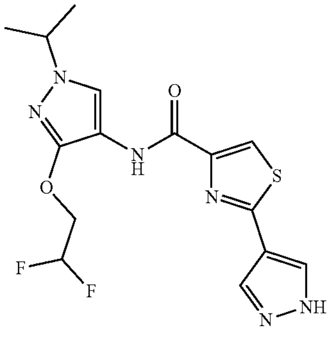 [SMILES: CC(C)n1cc(NC(=O)c2csc(-c3cn[nH]c3)n2)c(OCC(F)F)n1] | N-[3-(2,2-difluoroethoxy)-1-(1-methylethyl)-1H-pyrazol-4-yl]-2-(1H-pyrazol-4-yl)-1,3-thiazole-4-carboxamide | calc'd 383, found 383 |

Preparation of Example 2-1 and 2-2
Scheme 12. Synthesis of (R)- or (S)-N-(1-(1-cyclopropylethyl)-1H-pyrazol-4-yl)-2-(1H-pyrazol-4-yl)thiazole-4-carboxamide
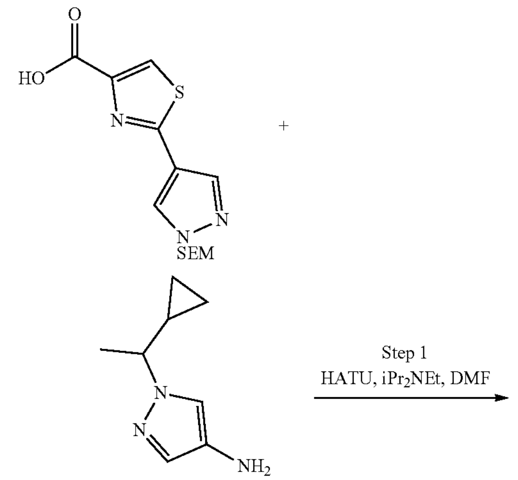
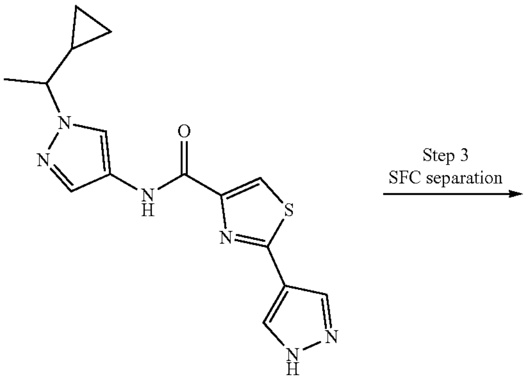
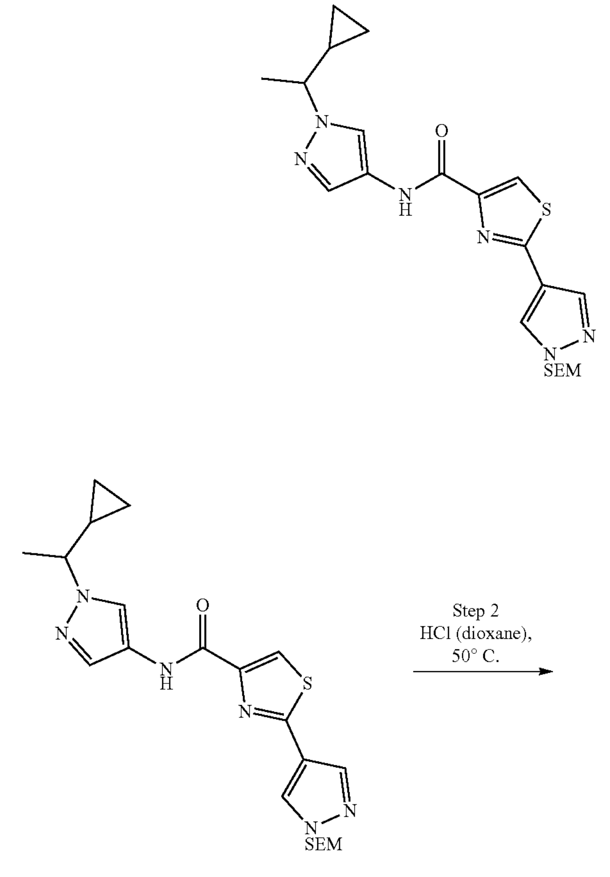
-continued
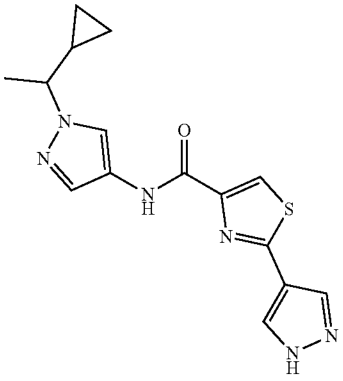
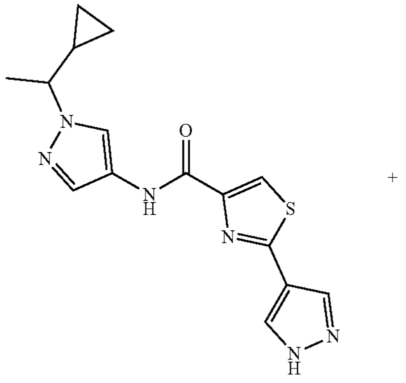
peak 1
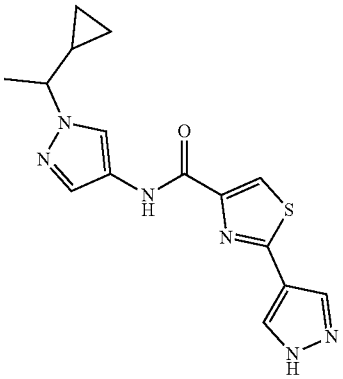
peak 2

Examples 2-1 and 2-2. (R)- or (S)—N-(1-(1-Cyclopropylethyl)-1H-pyrazol-4-yl)-2-(1H-pyrazol-4-yl)thiazole-4-carboxamide Step 1: To a mixture of 2-(1-((2-(trimethylsilyl)ethoxy)methyl)-1H-pyrazol-4-yl)thiazole-4-carboxylic acid (Intermediate 16, 180 mg, 0.55 mmol), 1-(1-cyclopropylethyl)-1H-pyrazol-4-amine (84 mg, 0.55 mmol), HATU (231 mg, 0.61 mmol), and DMF (2.8 mL) was added $iPr_2NEt$ (0.29 mL, 1.7 mmol). The resulting mixture was stirred at rt overnight. The crude solution containing N-(1-(1-cyclopropylethyl)-1H-pyrazol-4-yl)-2-(1-((2-(trimethylsilyl)ethoxy)methyl)-1H-pyrazol-4-yl)thiazole-4-carboxamide was carried forward without further purification. MS (ESI) m/z $C_{21}H_{31}N_6O_2SSi$ $[M+H]^+$ calc'd 459. found 459.

Step 2: To the above crude solution containing N-(1-(1-cyclopropylethyl)-1H-pyrazol-4-yl)-2-(1-((2-(trimethylsilyl)ethoxy)methyl)-1H-pyrazol-4-yl)thiazole-4-carboxamide was added HCl (1.0 mL, 4 N in dioxane, 4.0 mmol), and the resulting solution was stirred at rt. The crude reaction mixture was diluted with DMSO, filtered, and purified by preparative HPLC (reversed phase, MeCN/water with 0.1% TFA modifier) to afford N-(1-(1-cyclopropylethyl)-1H-pyrazol-4-yl)-2-(1H-pyrazol-4-yl)thiazole-4-carboxamide, TFA. MS (ESI) m/z $C_{15}H_{17}N_6OS$ $[M+H]^+$ calc'd 329, found 329.

Step 3: Racemic N-(1-(1-cyclopropylethyl)-1H-pyrazol-4-yl)-2-(1H-pyrazol-4-yl)thiazole-4-carboxamide, TFA was resolved to its component enantiomers by chiral preparative SFC (column: LUX-2, mobile phase A: $CO_2$, mobile phase B: MeOH with 0.25% dimethylethylamine) to afford (R)- or (S)—N-(1-(1-cyclopropylethyl)-1H-pyrazol-4-yl)-2-(1H-pyrazol-4-yl)thiazole-4-carboxamide (Example 2-1, peak 1, tR=6.45 min) and (S)- or (R)—N-(1-(1-cyclopropylethyl)-1H-pyrazol-4-yl)-2-(1H-pyrazol-4-yl)thiazole-4-carboxamide (Example 2-2, peak 2, tR=7.85 min). MS (ESI) m/z $C_{15}H_{17}N_6OS$ $[M+H]^+$ calc'd 329. found 329. $^1H$ NMR (500 MHz, DMSO-$d_6$) δ 13.33 (s, 1H), 10.34 (s, 1H), 8.27 (s, 1H), 8.20 (s, 1H), 8.13 (s, 1H), 7.71 (s, 1H), 3.70-3.56 (m, 1H), 1.58-1.40 (m, 3H), 1.29-1.11 (m, 2H), 0.64-0.53 (m, 1H), 0.48-0.38 (m, 1H), 0.37-0.27 (m, 1H).

Compounds in Table 7 below were prepared from Intermediate 16 using procedures analogous to those described in Scheme 12.

TABLE 7

| Number | Structure | Name | Exact Mass $[M + H]^+$ |
| --- | --- | --- | --- |
| 2-3 | 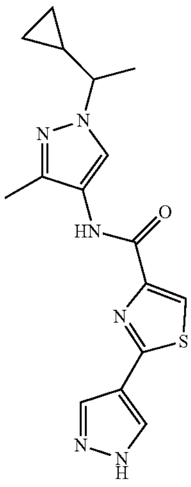 [SMILES: Cc1nn(C(C)C2CC2)cc1NC(=O)c1csc(-c2cn[nH]c2)n1] | (R)- or (S)-N-{1-[1-cyclopropylethyl]-3-methyl-1H-pyrazol-4-yl}-2-(1H-pyrazol-4-yl)-1,3-thiazole-4-carboxamide | calc'd 343, found 343 |

TABLE 7-continued

| Number | Structure | Name | Exact Mass $[M + H]^+$ |
| --- | --- | --- | --- |
| 2-4 | 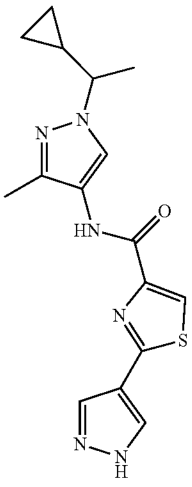 [SMILES: Cc1nn(C(C)C2CC2)cc1NC(=O)c1csc(-c2cn[nH]c2)n1] | (S)- or (R)-N-{1-[1-cyclopropylethyl]-3-methyl-1H-pyrazol-4-yl}-2-(1H-pyrazol-4-yl)-1,3-thiazole-4-carboxamide | calc'd 343, found 343 |

Preparation of Example 3-1

Scheme 13. Synthesis of N-(1-(1-cyclopropylethyl)-3-(difluoromethyl)-1H-pyrazol-4-yl)-2-(1H-pyrazol-4-yl)thiazole-4-carboxamide and N-(1-(1-cyclopropylethyl)-5-(difluoromethyl)-1H-pyrazol-4-yl)-2-(1H-pyrazol-4-yl)thiazole-4-carboxamide

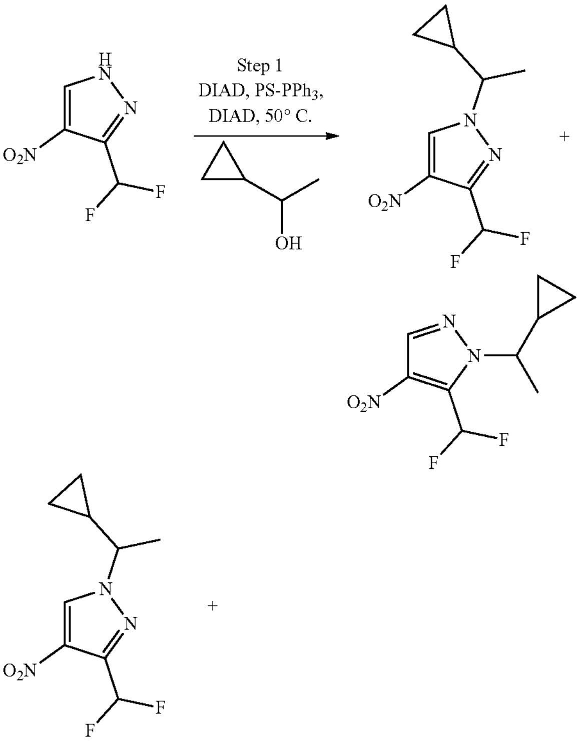

-continued

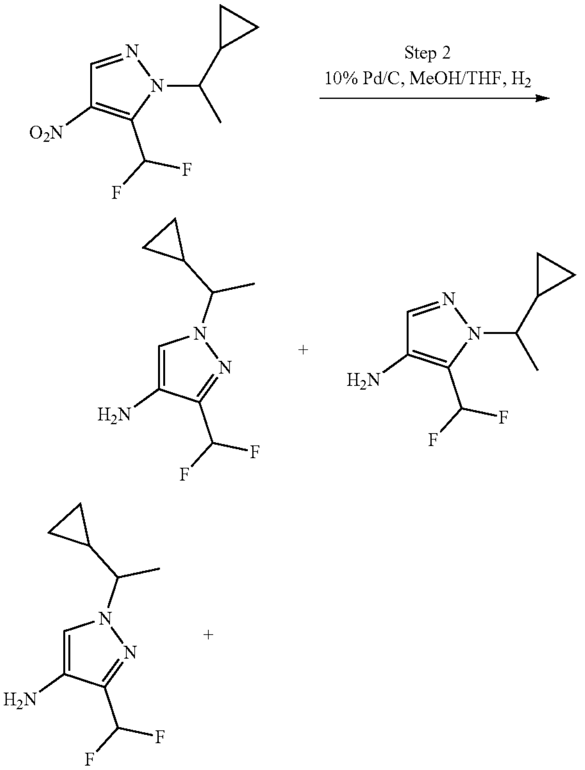

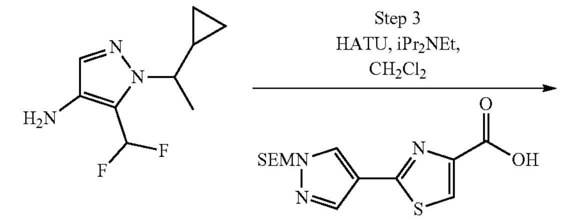

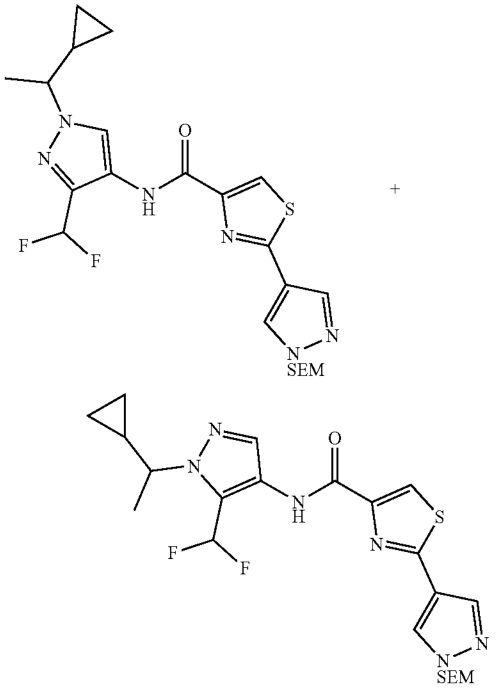

-continued

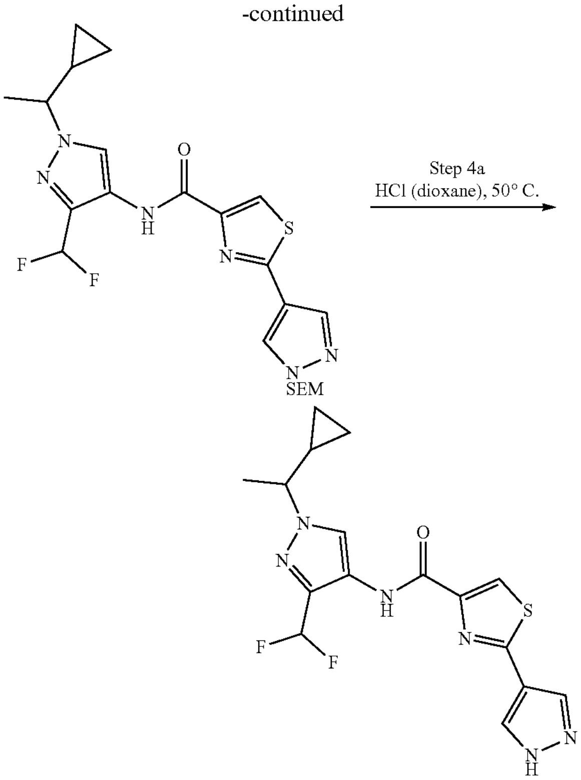

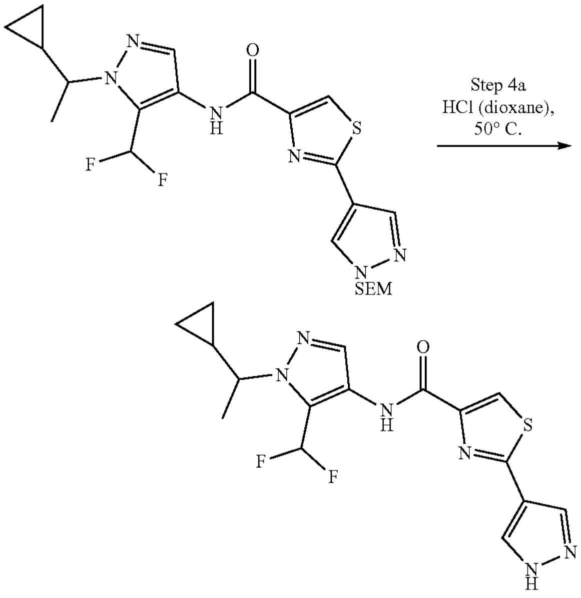

Example 3-1. N-(1-(1-Cyclopropylethyl)-3-(difluoromethyl)-1H-pyrazol-4-yl)-2-(1H-pyrazol-4-yl)thiazole-4-carboxamide Step 1: To a mixture of 3-(difluoromethyl)-4-nitro-1H-pyrazole (251 mg, 1.54 mmol), $PPh_3$ (605 mg, 2.31 mmol), and THF (7.7 mL) were added sequentially 1-cyclopropylethanol (0.23 mL, 2.3 mmol) and DIAD (0.45 mL, 2.3 mmol). The resulting solution was heated to 50° C., and then cooled to rt, at which point EtOAc, water, and brine were added. The phases were separated, and the aqueous layer was extracted twice with EtOAc. The combined organic layers were washed with brine, dried over $MgSO_4$, filtered, and concentrated to dryness in vacuo to afford a mixture of crude 1-(1-cyclopropylethyl)-3-(difluoromethyl)-4-nitro-1H-pyrazole and crude 1-(1-cyclopropylethyl)-5-(difluoromethyl)-4-nitro-1H-pyrazole. MS (ESI) m/z $C_9H_{12}F_2N_3O_2$ [M+H]+ 232. found 232.

Step 2: To a mixture of 1-(1-cyclopropylethyl)-3-(difluoromethyl)-4-nitro-1H-pyrazole and 1-(1-cyclopropylethyl)-5-(difluoromethyl)-4-nitro-1H-pyrazole was added THF (5 mL), 10 wt % Pd/C (164 mg, 0.15 mmol) and MeOH (5 mL). The resulting suspension was put under an atmosphere of $H_2$ and was stirred at rt. The reaction mixture was filtered through a plug of Celiter™, and the filtrate was concentrated to dryness in vacuo to afford a mixture of crude 1-(1-cyclopropylethyl)-3-(difluoromethyl)-1H-pyrazol-4-amine and crude 1-(1-cyclopropylethyl)-5-(difluoromethyl)-1H-pyrazol-4-amine. MS (ESI) m/z $C_9H_{14}F_2N_3$ $[M+H]^+$ calc'd 202. found 202.

Step 3: A stock solution of the mixture of 1-(1-cyclopropylethyl)-3-(difluoromethyl)-1H-pyrazol-4-amine and crude 1-(1-cyclopropylethyl)-5-(difluoromethyl)-1H-pyrazol-4-amine and $CH_2Cl_2$ (7.5 mL) was prepared. To a mixture of 2-(1-((2-(trimethylsilyl)ethoxy)methyl)-1H-pyrazol-4-yl)thiazole-4-carboxylic acid (Intermediate 16, 501 mg, 1.54 mmol) and HATU (585 mg, 1.54 mmol) were sequentially added $CH_2Cl_2$ (7.5 mL), $iPr_2NEt$ (0.81 mL, 4.6 mmol), and the aforementioned stock solution. The reaction mixture was stirred at rt, at which point additional $CH_2Cl_2$ and water were added. The phases were separated, and the aqueous layer was extracted twice with $CH_2Cl_2$. The combined organic layers were washed with water, dried over $MgSO_4$, filtered, and concentrated to dryness in vacuo. The crude residue was purified by silica gel chromatography (eluent: 5-40% EtOAc/$CH_2Cl_2$) to afford N-(1-(1-cyclopropylethyl)-3-(difluoromethyl)-1H-pyrazol-4-yl)-2-(1-((2-(trimethylsilyl)ethoxy)methyl)-1H-pyrazol-4-yl)thiazole-4-carboxamide (peak 1) and N-(1-(1-cyclopropylethyl)-5-(difluoromethyl)-1H-pyrazol-4-yl)-2-(1-((2-(trimethylsilyl)ethoxy)methyl)-1H-pyrazol-4-yl)thiazole-4-carboxamide (peak 2). MS (ESI) m/z $C_{22}H_{31}F_2N_6O_2SSi$ $[M+H]^+$ calc'd 509. found 509.

Step 4a: To N-(1-(1-cyclopropylethyl)-3-(difluoromethyl)-1H-pyrazol-4-yl)-2-(1-((2-(trimethylsilyl)ethoxy)methyl)-1H-pyrazol-4-yl)thiazole-4-carboxamide (peak 1, 464 mg, 0.91 mmol) were sequentially added $CH_2Cl_2$ (5 mL), and then HCl (2.3 mL, 2 N in ether, 4.6 mmol), at which point precipitate was observed. The suspension was diluted with ether, and the precipitate was collected by filtration to afford N-(1-(1-cyclopropylethyl)-3-(difluoromethyl)-1H-pyrazol-4-yl)-2-(1H-pyrazol-4-yl)thiazole-4-carboxamide. MS (ESI) m/z $C_{16}H_{17}F_2N_6OS$ $[M+H]^+$ calc'd 379. found 379. $^1H$ NMR (500 MHz, DMSO-$d_6$) δ 9.75 (s, 1H), 8.40-8.14 (m, 4H), 7.18 (t, J=54.1 Hz, 1H), 3.81-3.62 (m, 1H), 1.62-1.39 (m, 3H), 1.39-1.14 (m, 2H), 0.67-0.55 (m, 1H), 0.51-0.41 (m, 1H), 0.41-0.29 (m, 1H).

Step 4b: To N-(1-(1-cyclopropylethyl)-5-(difluoromethyl)-1H-pyrazol-4-yl)-2-(1-((2-(trimethylsilyl)ethoxy)methyl)-1H-pyrazol-4-yl)thiazole-4-carboxamide (peak 2, 344 mg, 0.68 mmol) were sequentially added $CH_2Cl_2$ (5 mL), and then HCl (1.7 mL, 2 N in ether, 3.4 mmol), at which point precipitate was observed. The suspension was diluted with ether, and the precipitate was collected by filtration to afford N-(1-(1-cyclopropylethyl)-5-(difluoromethyl)-1H-pyrazol-4-yl)-2-(1H-pyrazol-4-yl)thiazole-4-carboxamide (Intermediate 23). MS (ESI) m/z $C_{16}H_{17}F_2N_6OS$ $[M+H]^+$ calc'd 379. found 379.

Compounds in Table 8 below were prepared from Intermediate 16 using procedures analogous to those described in Scheme 13.

TABLE 8

| Number | Structure | Name | Exact Mass $[M + H]^+$ |
|---|---|---|---|
| 3-2 | 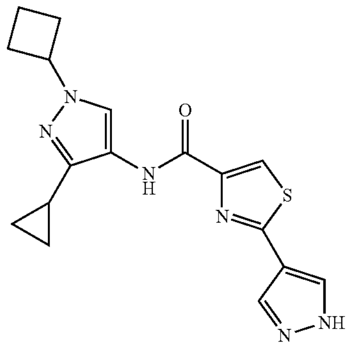 [SMILES: O=C(Nc1cn(C2CCC2)nc1C1CC1)c1csc(-c2cn[nH]c2)n1] | N-(1-cyclobutyl-3-cyclopropyl-1H-pyrazol-4-yl)-2-(1H-pyrazol-4-yl)-1,3-thiazole-4-carboxamide | calc'd 355, found 355 |
| 3-3 | 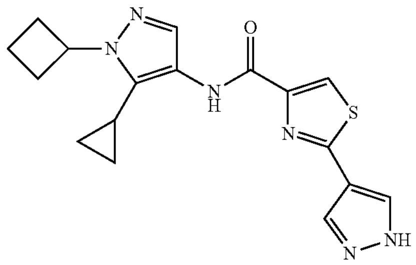 [SMILES: O=C(Nc1cnn(C2CCC2)c1C1CC1)c1csc(-c2cn[nH]c2)n1] | N-(1-cyclobutyl-5-cyclopropyl-1H-pyrazol-4-yl)-2-(1H-pyrazol-4-yl)-1,3-thiazole-4-carboxamide | calc'd 355, found 355 |

Preparation of Examples 3-4 and 3-5

Scheme 14. Synthesis of (R)- or (S)—N-(1-(1-cyclopropylethyl)-5-(difluoromethyl)-1H-pyrazol-4-yl)-2-(1H-pyrazol-4-yl)thiazole-4-carboxamide

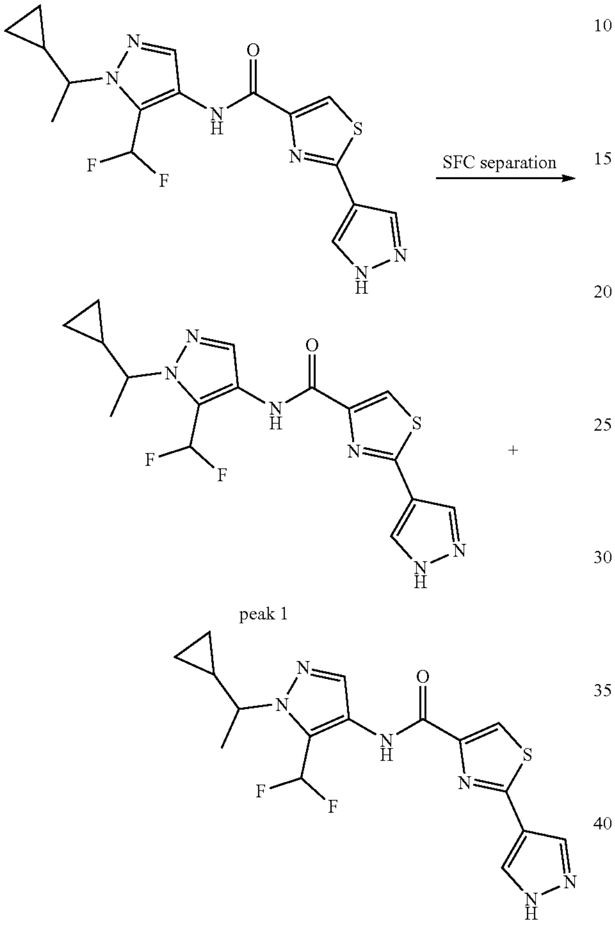

Examples 3-4 and 3-5. (R)- or (S)—N-(1-(1-Cyclopropylethyl)-5-(difluoromethyl)-1H-pyrazol-4-yl)-2-(1H-pyrazol-4-yl)thiazole-4-carboxamide Racemic N-(1-(1-cyclopropylethyl)-5-(difluoromethyl)-1H-pyrazol-4-yl)-2-(1H-pyrazol-4-yl)thiazole-4-carboxamide, TFA (Intermediate 23, 344 mg, 0.68 mmol) was resolved into its component enantiomers by chiral preparative SFC (column: LUX-2, mobile phase A: $CO_2$, mobile phase B: MeOH with 0.25% dimethylethylamine) to afford (R)- or (S)—N-(1-(1-cyclopropylethyl)-5-(difluoromethyl)-1H-pyrazol-4-yl)-2-(1H-pyrazol-4-yl)thiazole-4-carboxamide (Example 3-4, peak 1, tR=4.45 min) and (S)- or (R)—N-(1-(1-cyclopropylethyl)-5-(difluoromethyl)-1H-pyrazol-4-yl)-2-(1H-pyrazol-4-yl)thiazole-4-carboxamide (Example 3-5, peak 2, tR=5.53 min). MS (ESI) m/z $C_{16}H_{17}F_2N_6OS$ $[M+H]^+$ calc'd 379. found 379. $^1H$ NMR (600 MHz, DMSO-$d_6$) δ 13.40 (s, 1H), 10.00 (s, 1H), 8.46 (s, 1H), 8.29 (s, 1H), 8.07 (s, 1H), 7.85 (s, 1H), 7.30 (t, J=51.9 Hz, 1H), 3.86-3.71 (m, 1H), 1.51 (d, J=6.6 Hz, 3H), 1.47-1.37 (m, 2H), 0.65-0.59 (m, 1H), 0.43-0.35 (m, 1H), 0.31-0.25 (m, 1H).

Preparation of Example 4-1

Scheme 15. Synthesis of N-(1-cyclopropyl-1H-pyrazol-4-yl)-6-(1-(2,2,2-trifluoroethyl)-1H-pyrazol-4-yl)picolinamide

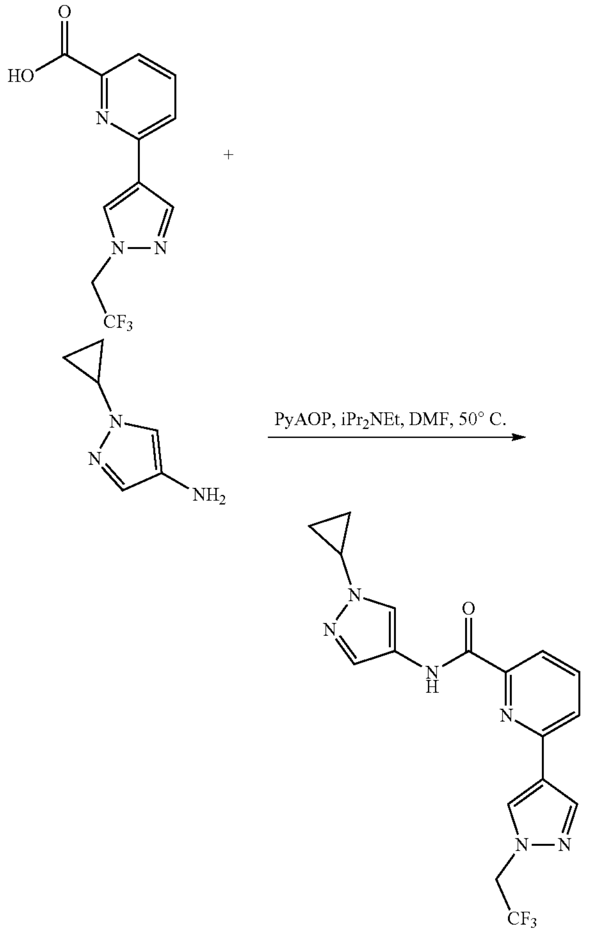

Example 4-1. N-(1-Cyclopropyl-1H-pyrazol-4-yl)-6-(1-(2,2,2-trifluoroethyl)-1H-pyrazol-4-yl)picolinamide To a mixture of 6-(1-(2,2,2-trifluoroethyl)-1H-pyrazol-4-yl)picolinic acid (Intermediate 19, 54.2 mg, 0.20 mmol), PyAOP (104 mg, 0.20 mmol), 1-cyclopropyl-1H-pyrazol-4-amine, HCl (31.9 mg, 0.20 mmol) and DMF (1 mL) was added $iPr_2NEt$ (0.11 mL, 0.60 mmol). The resulting mixture was heated to 50 NC overnight, and then cooled to a. The crude reaction mixture was diluted with 1:1 DMSO/MeOH, filtered, and purified by preparative HPLC (reversed-phase, MeCN/water with 0.100 $NH_4OH$ modifier) to afford N-(1-cyclopropyl-1H-pyrazol-4-yl)-6-(1-(2,2,2-trifluoroethyl)-1H-pyrazol-4-yl)picolinamide. MS (ESI) m/z $C_{17}H_{16}F_3N_6O$ $[M+H]^+$ calc'd 377. found 377. $^1H$ NMR (600 MHz, DMSO-$d_6$) δ 10.63 (s, 1H), 8.72 (s, 1H), 8.52 (s, 1H), 8.17

(s, 1H), 8.04-7.98 (m, 1H), 7.95-7.90 (m, 2H), 7.74 (s, 1H), 5.24 (q, J=8.8 Hz, 2H), 3.77-3.72 (m, 1H), 1.07-1.01 (m, 2H), 0.992-0.94 (n, 2H).

Compounds in Table 9 below were prepared from commercial carboxylic acids or Intermediate 18 using procedures analogous to those described in Scheme 15.

TABLE 9

| Number | Structure | Name | Exact Mass [M + H]$^+$ |
|---|---|---|---|
| 4-2 | 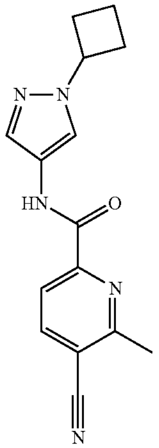 [SMILES: Cc1nc(C(=O)Nc2cnn(C3CCC3)c2)ccc1C#N] | 5-cyano-N-(1-cyclobutyl-1H-pyrazol-4-yl)-6-methylpyridine-2-carboxamide | calc'd 282, found 282 |
| 4-3 | 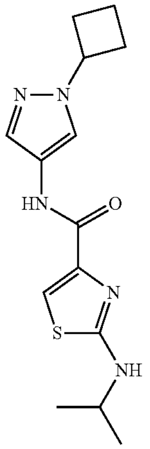 [SMILES: CC(C)Nc1nc(C(=O)Nc2cnn(C3CCC3)c2)cs1] | N-(1-cyclobutyl-1H-pyrazol-4-yl)-2-[(1-methylethyl)amino]-1,3-thiazole-4-carboxamide | calc'd 306, found 306 |
| 4-4 | 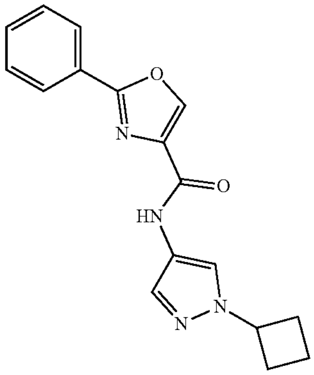 [SMILES: O=C(Nc1cnn(C2CCC2)c1)c1coc(-c2ccccc2)n1] | N-(1-cyclobutyl-1H-pyrazol-4-yl)-2-phenyl-1,3-oxazole-4-carboxamide | calc'd 309, found 309 |

TABLE 9-continued
| Number | Structure | Name | Exact Mass [M + H]$^+$ |
|---|---|---|---|
| 4-5 | 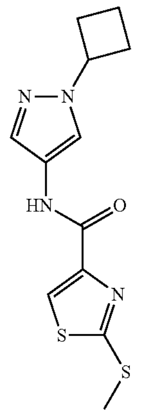 [SMILES: CSc1nc(C(=O)Nc2cnn(C3CCC3)c2)cs1] | N-(1-cyclobutyl-1H-pyrazol-4-yl)-2-(methylsulfanyl)-1,3-thiazole-4-carboxamide | calc'd 295, found 295 |
| 4-6 | 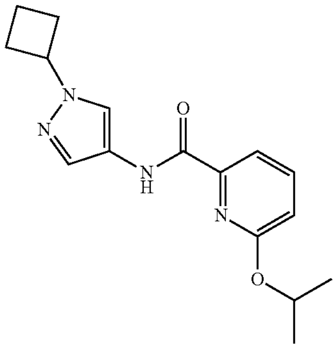 [SMILES: CC(C)Oc1cccc(C(=O)Nc2cnn(C3CCC3)c2)n1] | N-(1-cyclobutyl-1H-pyrazol-4-yl)-6-(1-methylethoxy) pyridine-2-carboxamide | calc'd 301, found 301 |
| 4-7 | 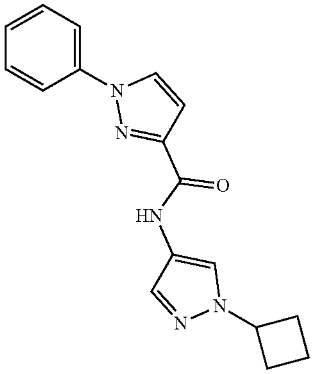 [SMILES: O=C(Nc1cnn(C2CCC2)c1)c1ccn(-c2ccccc2)n1] | N-(1-cyclobutyl-1H-pyrazol-4-yl)-1-phenyl-1H-pyrazole-3-carboxamide | calc'd 308, found 308 |
| 4-8 | 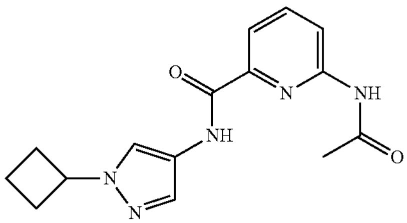 [SMILES: CC(=O)Nc1cccc(C(=O)Nc2cnn(C3CCC3)c2)n1] | 6-(acetylamino)-N-(1-cyclobutyl-1H-pyrazol-4-yl)pyridine-2-carboxamide | calc'd 300, found 300 |

TABLE 9-continued
| Number | Structure | Name | Exact Mass [M + H]$^+$ |
|---|---|---|---|
| 4-9 | 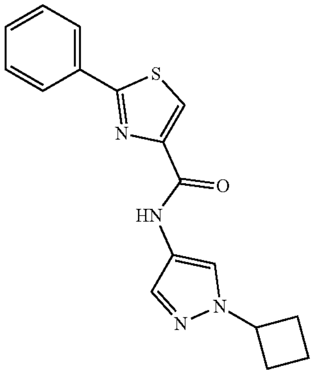 [SMILES: O=C(Nc1cnn(C2CCC2)c1)c1csc(-c2ccccc2)n1] | N-(1-cyclobutyl-1H-pyrazol-4-yl)-2-phenyl-1,3-thiazole-4-carboxamide | calc'd 325, found 325 |
| 4-10 | 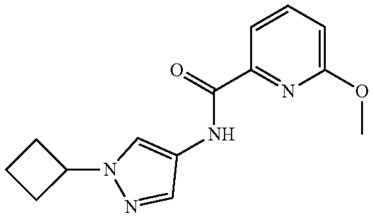 [SMILES: COc1cccc(C(=O)Nc2cnn(C3CCC3)c2)n1] | N-(1-cyclobutyl-1H-pyrazol-4-yl)-6-methoxypyridine-2-carboxamide | calc'd 273, found 273 |
| 4-11 | 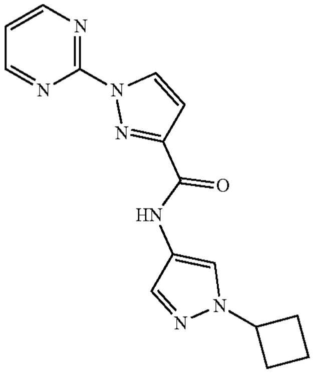 [SMILES: O=C(Nc1cnn(C2CCC2)c1)c1ccn(-c2ncccn2)n1] | N-(1-cyclobutyl-1H-pyrazol-4-yl)-1-pyrimidin-2-yl-1H-pyrazole-3-carboxamide | calc'd 310, found 310 |
| 4-12 | 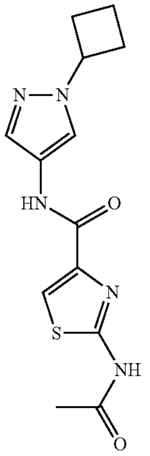 [SMILES: CC(=O)Nc1nc(C(=O)Nc2cnn(C3CCC3)c2)cs1] | 2-(acetylamino)-N-(1-cyclobutyl-1H-pyrazol-4-yl)-1,3-thiazole-4-carboxamide | calc'd 306, found 306 |

TABLE 9-continued
| Number | Structure | Name | Exact Mass [M + H]$^+$ |
| --- | --- | --- | --- |
| 4-13 | 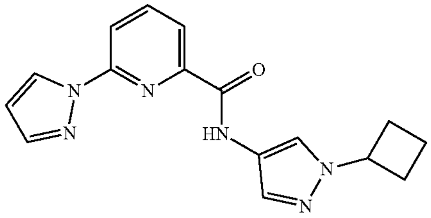 [SMILES: O=C(Nc1cnn(C2CCC2)c1)c1cccc(-n2cccn2)n1] | N-(1-cyclobutyl-1H-pyrazol-4-yl)-6-(1H-pyrazol-1-yl)pyridine-2-carboxamide | calc'd 309, found 309 |
| 4-14 | 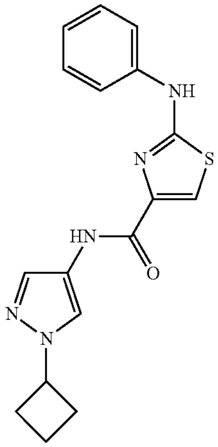 [SMILES: O=C(Nc1cnn(C2CCC2)c1)c1csc(Nc2ccccc2)n1] | N-(1-cyclobutyl-1H-pyrazol-4-yl)-2-(phenylamino)-1,3-thiazole-4-carboxamide | calc'd 340, found 340 |
| 4-15 | 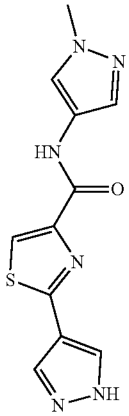 [SMILES: Cn1cc(NC(=O)c2csc(-c3cn[nH]c3)n2)cn1] | N-(1-methyl-1H-pyrazol-4-yl)-2-(1H-pyrazol-4-yl)thiazole-4-carboxamide | calc'd 275, found 275 |
| 4-16 | 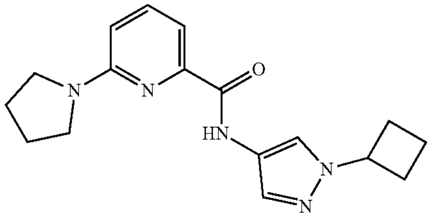 [SMILES: O=C(Nc1cnn(C2CCC2)c1)c1cccc(N2CCCC2)n1] | N-(1-cyclobutyl-1H-pyrazol-4-yl)-6-(pyrrolidin-1-yl)picolinamide | calc'd 312, found 312 |

TABLE 9-continued

| Number | Structure | Name | Exact Mass [M + H]$^+$ |
|---|---|---|---|
| 4-17 | 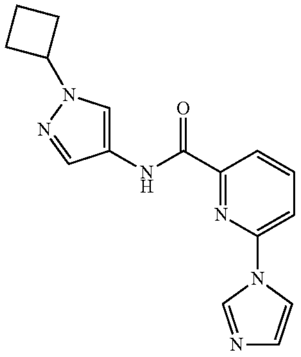 [SMILES: O=C(Nc1cnn(C2CCC2)c1)c1cccc(-n2ccnc2)n1] | N-(1-cyclobutyl-1H-pyrazol-4-yl)-6-(1H-imidazol-1-yl)picolinamide | calc'd 309, found 309 |
| 4-18 | 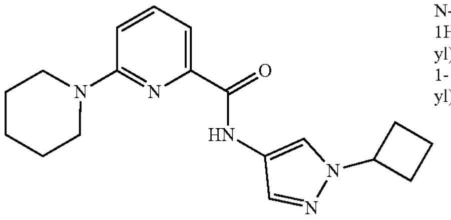 | N-(1-cyclobutyl-1H-pyrazol-4-yl)-6-(piperidin-1-yl)picolinamide | calc'd 326, found 326 |

Preparation of Example 5-1

Scheme 16. Synthesis of N-(1-((3-fluorooxetan-3-yl)methyl)-1H-pyrazol-4-yl)-2-(1H-pyrazol-4-yl) thiazole-4-carboxamide

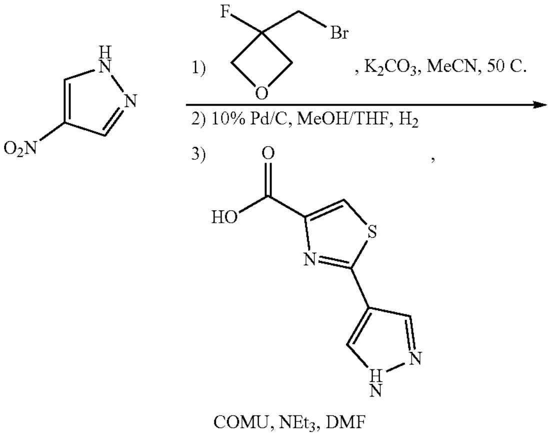

-continued

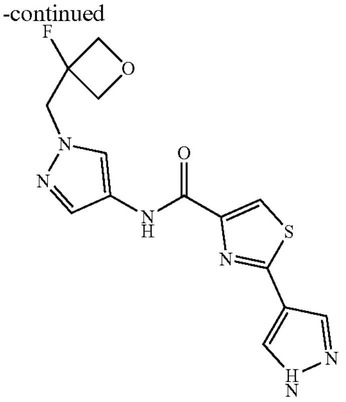

Example 5-1. N-(1-((3-Fluorooxetan-3-yl)methyl)-1H-pyrazol-4-yl)-2-(1H-pyrazol-4-yl)thiazole-4-carboxamide To a mixture of 4-nitro-1H-pyrazole (53 mg, 0.47 mmol), $K_2CO_3$ (130 mg, 0.94 mmol), and MeCN (2.4 mL) was added 3-(bromomethyl)-3-fluorooxetane (79 mg, 0.71 mmol). The resulting suspension was heated to 50° C., and then cooled to rt. The reaction mixture was vacuum filtered through a plug of Celiter™, and the filtrate was concentrated to dryness in vacuo. To the residue was added THF (2 mL), 10 wt % Pd/C (50 mg, 0.047 mmol), and MeOH (2 mL). The resulting suspension was put under an atmosphere of $H_2$ and was stirred at rt overnight. The reaction mixture was filtered through a plug of Celite™ and the filtrate was concentrated to dryness in vacuo. The crude residue was re-dissolved in $CH_2Cl_2$ (1 mL), and a vigorously stirred suspension of 2-(1H-pyrazol-4-yl)thiazole-4-carboxylic acid (Intermediate 18, 92 mg, 0.47 mmol), COMU (201 mg, 0.47 mmol), $CH_2Cl_2$ (1.5 mL), and $NEt_3$ (197 µL, 1.4 mmol) was subsequently added, followed by additional $CH_2Cl_2$ (1 mL).

The resulting suspension was stirred at rt overnight. To the reaction mixture was added 1:1 DMSO/MeOH, and the mixture was concentrated to dryness in vacuo. The crude residue was re-dissolved in DMSO, filtered, and purified by preparative HPLC (reversed phase, MeCN/water with 0.1% TFA modifier) to afford N-(1-((3-Fluorooxetan-3-yl)methyl)-1H-pyrazol-4-yl)-2-(1H-pyrazol-4-yl)thiazole-4-carboxamide, TFA. MS (ESI) m/z $C_{14}H_{14}FN_6O_2S$ $[M+H]^+$ calc'd 349. found 349. $^1H$ NMR (500 MHz, DMSO-$d_6$) δ 10.42 (s, 1H), 8.27 (s, 1H), 8.23 (s, 1H), 8.13 (s, 1H), 7.77 (s, 1H), 4.84-4.52 (m, 6H).

Preparation of Example 6-1

Scheme 17. Synthesis of N-(3-(hydroxymethyl)-1-methyl-1H-pyrazol-4-yl)-2-(1H-pyrazol-4-yl)thiazole-4-carboxamide

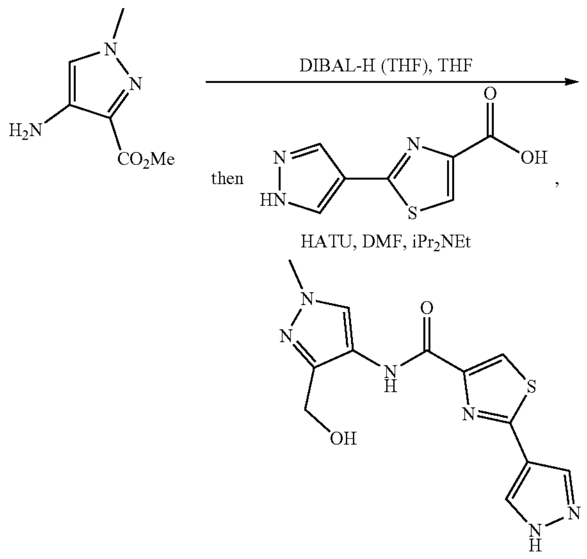

Example 6-1. N-(3-(Hydroxymethyl)-1-methyl-1H-pyrazol-4-yl)-2-(1H-pyrazol-4-yl)thiazole-4-carboxamide To methyl 4-amino-1-methyl-1H-pyrazole-3-carboxylate (50 mg, 0.32 mmol) was added THF (1.3 mL) and then dropwise DIBAL-H (1.3 mL, 1 M in THF, 1.3 mmol). The resulting solution was stirred at rt overnight. To the reaction mixture were added sequentially EtOAc dropwise, water (52 μL), 15% w/v NaOH (52 μL), and water (129 μL). The reaction mixture was dried over $MgSO_4$, filtered through a plug of Celite, and concentrated to dryness in vacuo. To the crude residue were added sequentially 2-(1H-pyrazol-4-yl)thiazole-4-carboxylic acid (Intermediate 18, 62.9 mg, 0.32 mmol), HATU (122 mg, 0.32 mmol), DMF (1.5 mL), and then $iPr_2NEt$ (0.17 mL, 0.97 mmol). The resulting solution was stirred at rt overnight. The reaction mixture was diluted with DMSO, filtered, and purified by preparative HPLC (reversed phase, MeCN/water with 0.1% TFA modifier) to afford N-(3-(hydroxymethyl)-1-methyl-1H-pyrazol-4-yl)-2-(1H-pyrazol-4-yl)thiazole-4-carboxamide, TFA. MS (ESI) m/z $C_{12}H_{13}N_6O_2S$ [M+H]'calc'd 305. found 305. $^1H$ NMR (500 MHz, DMSO-$d_6$) δ 10.17 (s, 1H), 8.30-8.18 (m, 2H), 8.12 (s, 1H), 4.68 (s, 2H), 3.79 (s, 3H).

Preparation of Example 7-1

Scheme 18. Synthesis of N-(1-(cyclobutylmethyl)-1H-pyrazol-4-yl)-2-(1H-pyrazol-4-yl)thiazole-4-carboxamide

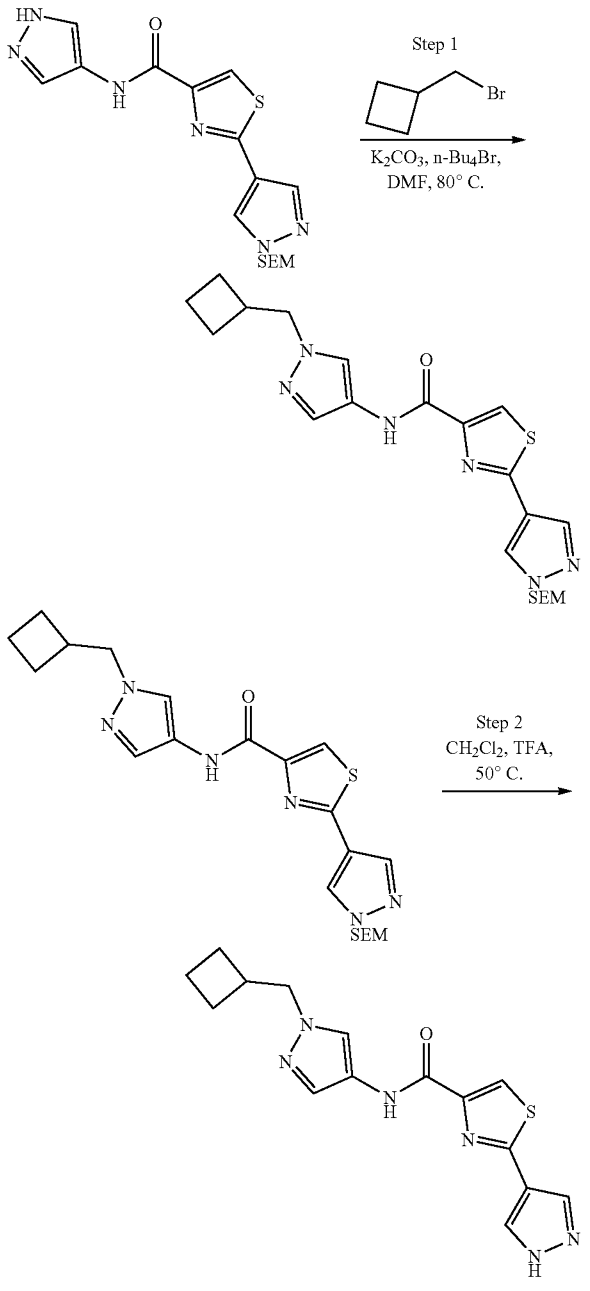

Example 7-1. N-(1-(Cyclobutylmethyl)-1H-pyrazol-4-yl)-2-(1H-pyrazol-4-yl)thiazole-4-carboxamide Step 1: To (bromomethyl)cyclobutane (19 mg, 0.13 mmol) was added N-(1H-pyrazol-4-yl)-2-(1-((2-(trimethylsilyl)ethoxy)methyl)-1H-pyrazol-4-yl)thiazole-4-carboxamide (Intermediate 20, 25 mg, 0.064 mmol) in DMF (1 mL), $K_2CO_3$ (26.5 mg, 0.19 mmol), and $n-Bu_4Br$ (2.4 mg, 0.006 mmol). The resulting suspension was heated to 80° C. for 16 h, and then cooled to rt. The reaction mixture was concentrated to dryness in vacuo to afford crude N-(1-(cyclobutylmethyl)-1H-pyrazol-4-yl)-2-(1-((2-(trimethylsilyl)ethoxy)methyl)-1H-pyrazol-4-yl)thiazole-4-carboxamide. MS (ESI) m/z $C_{21}H_{31}N_6O_2SSi$ $[M+H]^+$ calc'd 459. found 459.

Step 2: To crude N-(1-(cyclobutylmethyl)-1H-pyrazol-4-yl)-2-(1-((2-(trimethylsilyl)ethoxy)methyl)-1H-pyrazol-4-yl)thiazole-4-carboxamide was added $CH_2Cl_2$ (0.8 mL) and TFA (0.74 mL, 9.6 mmol). The reaction mixture was heated to 50° C. for 1 h, then cooled to rt, and then concentrated to dryness in vacuo. The crude residue was re-dissolved in DMSO, filtered, and purified by preparative HPLC (reversed phase, MeCN/water with 0.1% TFA modifier) to afford N-(1-(cyclobutylmethyl)-1H-pyrazol-4-yl)-2-(1H-pyrazol-4-yl)thiazole-4-carboxamide, TFA. MS (ESI) m/z $C_{15}H_{17}N_6OS$ $[M+H]^+$ calc'd 329. found 329. $^1H$ NMR (500 MHz, DMSO-$d_6$) δ 10.33 (s, 1H), 8.45 (br s, 1H), 8.20 (s, 1H), 8.09 (br s, 1H), 8.04 (s, 1H), 7.69 (s, 1H), 4.11 (d, J=7.3 Hz, 2H), 2.77-2.68 (m, 1H), 2.01-1.93 (m, 2H), 1.89-1.81 (m, 2H), 1.80-1.72 (m, 2H).

Compounds in Table 10 below were prepared from Intermediates 20-22 using procedures analogous to those described in Scheme 18.

TABLE 10

| Number | Structure | Name | Exact Mass $[M + H]^+$ |
|---|---|---|---|
| 7-2 | 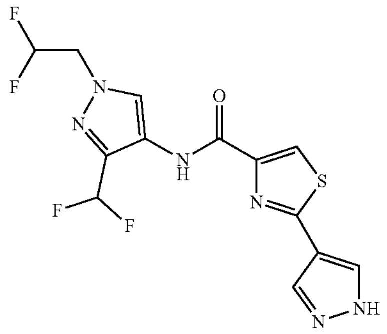 [SMILES: O=C(Nc1cn(CC(F)F)nc1C(F)F)c1csc(-c2cn[nH]c2)n1] | N-[1-(2,2-difluoroethyl)-3-(difluoromethyl)-1H-pyrazol-4-yl]-2-(1H-pyrazol-4-yl)-1,3-thiazole-4-carboxamide | calc'd 375, found 375 |
| 7-3 | 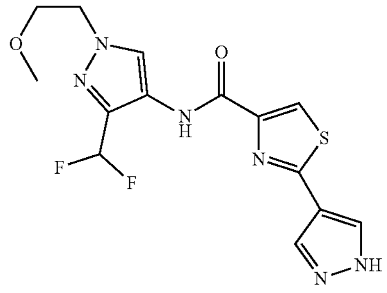 | N-[3-(difluoromethyl)-1-(2-methoxyethyl)-1H-pyrazol-4-yl]-2-(1H-pyrazol-4-yl)-1,3-thiazole-4-carboxamide | calc'd 369, found 369 |
| 7-4 | 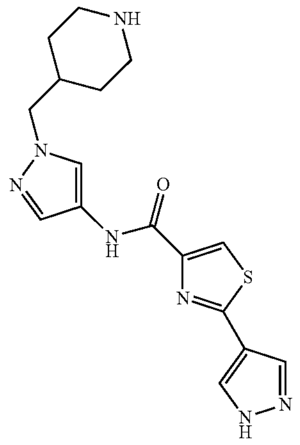 [SMILES: O=C(Nc1cnn(CC2CCNCC2)c1)c1csc(-c2cn[nH]c2)n1] | N-{1-[(piperidin-4-yl)methyl]-1H-pyrazol-4-yl}-2-(1H-pyrazol-4-yl)-1,3-thiazole-4-carboxamide | calc'd 358, found 358 |

TABLE 10-continued

| Number | Structure | Name | Exact Mass [M + H]+ |
|---|---|---|---|
| 7-5 | 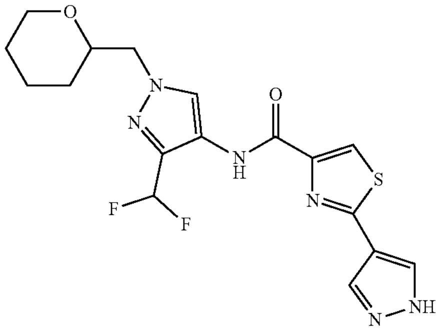 [SMILES: O=C(Nc1cn(CC2CCCCO2)nc1C(F)F)c1csc(-c2cn[nH]c2)n1] | N-[3-(difluoromethyl)-1-(tetrahydro-2H-pyran-2-ylmethyl)-1H-pyrazol-4-yl]-2-(1H-pyrazol-4-yl)-1,3-thiazole-4-carboxamide | calc'd 409, found 409 |
| 7-6 | 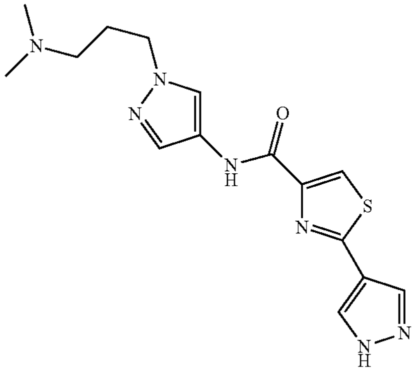 [SMILES: CN(C)CCCn1cc(NC(=O)c2csc(-c3cn[nH]c3)n2)cn1] | N-{1-[3-(dimethylamino)propyl]-1H-pyrazol-4-yl}-2-(1H-pyrazol-4-yl)-1,3-thiazole-4-carboxamide | calc'd 346, found 346 |
| 7-7 | 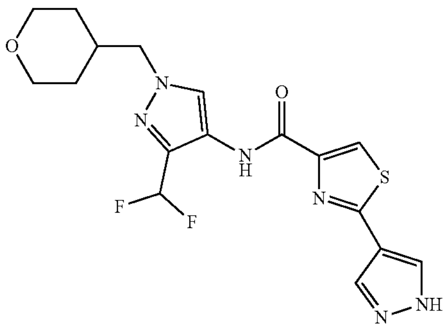 [SMILES: O=C(Nc1cn(CC2CCOCC2)nc1C(F)F)c1csc(-c2cn[nH]c2)n1] | N-[3-(difluoromethyl)-1-(tetrahydro-2H-pyran-4-ylmethyl)-1H-pyrazol-4-yl]-2-(1H-pyrazol-4-yl)-1,3-thiazole-4-carboxamide | calc'd 409, found 409 |
| 7-8 | 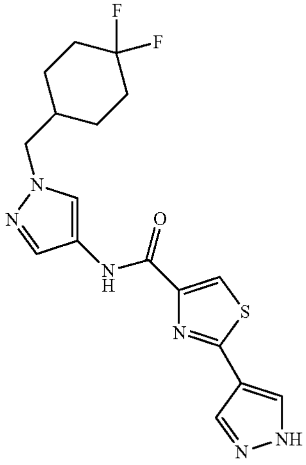 [SMILES: O=C(Nc1cnn(CC2CCC(F)(F)CC2)c1)c1csc(-c2cn[nH]c2)n1] | N-{1-[(4,4-difluorocyclohexyl)methyl]-1H-pyrazol-4-yl}-2-(1H-pyrazol-4-yl)-1,3-thiazole-4-carboxamide | calc'd 393, found 393 |

TABLE 10-continued

| Number | Structure | Name | Exact Mass [M + H]+ |
|---|---|---|---|
| 7-9 | 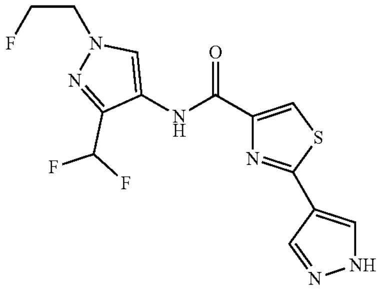 [SMILES: O=C(Nc1cn(CCF)nc1C(F)F)c1csc(-c2cn[nH]c2)n1] | N-[3-(difluoromethyl)-1-(2-fluoroethyl)-1H-pyrazol-4-yl]-2-(1H-pyrazol-4-yl)-1,3-thiazole-4-carboxamide | calc'd 357, found 357 |
| 7-10 | 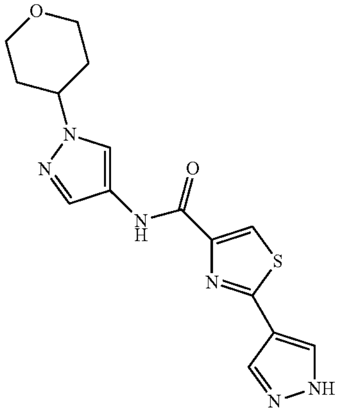 [SMILES: O=C(Nc1cnn(C2CCOCC2)c1)c1csc(-c2cn[nH]c2)n1] | 2-(1H-pyrazol-4-yl)-N-[1-(tetrahydro-2H-pyran-4-yl)-1H-pyrazol-4-yl]-1,3-thiazole-4-carboxamide | calc'd 345, found 345 |
| 7-11 | 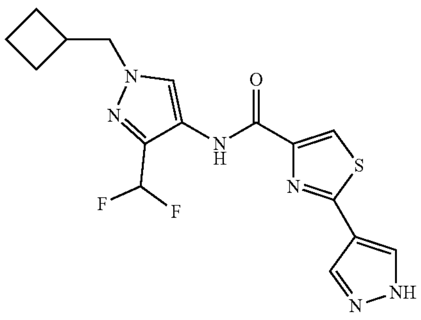 [SMILES: O=C(Nc1cn(CC2CCC2)nc1C(F)F)c1csc(-c2cn[nH]c2)n1] | N-[1-(cyclobutylmethyl)-3-(difluoromethyl)-1H-pyrazol-4-yl]-2-(1H-pyrazol-4-yl)-1,3-thiazole-4-carboxamide | calc'd 379, found 379 |
| 7-12 | 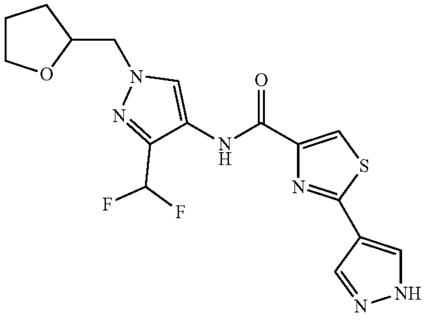 [SMILES: O=C(Nc1cn(CC2CCCO2)nc1C(F)F)c1csc(-c2cn[nH]c2)n1] | N-[3-(difluoromethyl)-1-(tetrahydrofuran-2-ylmethyl)-1H-pyrazol-4-yl]-2-(1H-pyrazol-4-yl)-1,3-thiazole-4-carboxamide | calc'd 395, found 395 |

TABLE 10-continued

| Number | Structure | Name | Exact Mass [M + H]$^+$ |
|---|---|---|---|
| 7-13 | 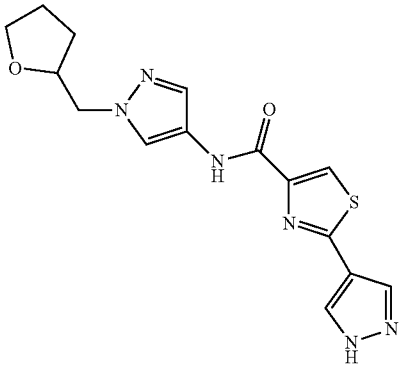 [SMILES: O=C(Nc1cnn(CC2CCCO2)c1)c1csc(-c2cn[nH]c2)n1] | 2-(1H-pyrazol-4-yl)-N-[1-(tetrahydrofuran-2-ylmethyl)-1H-pyrazol-4-yl]-1,3-thiazole-4-carboxamide | calc'd 345, found 345 |
| 7-14 | 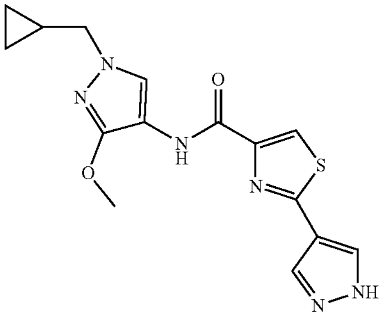 [SMILES: COc1nn(CC2CC2)cc1NC(=O)c1csc(-c2cn[nH]c2)n1] | N-[1-(cyclopropylmethyl)-3-methoxy-1H-pyrazol-4-yl]-2-(1H-pyrazol-4-yl)-1,3-thiazole-4-carboxamide | calc'd 345, found 345 |
| 7-15 | 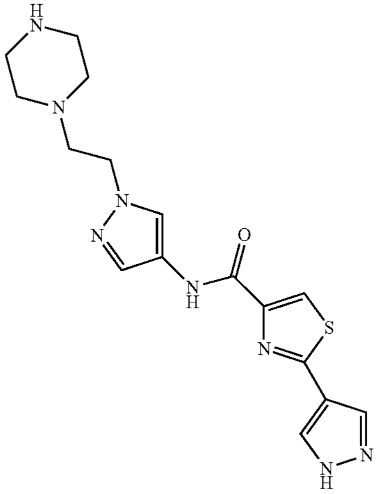 | N-{1-[2-(piperazin-1-yl)ethyl]-1H-pyrazol-4-yl}-2-(1H-pyrazol-4-yl)-1,3-thiazole-4-carboxamide | calc'd 373, found 373 |
| 7-16 | 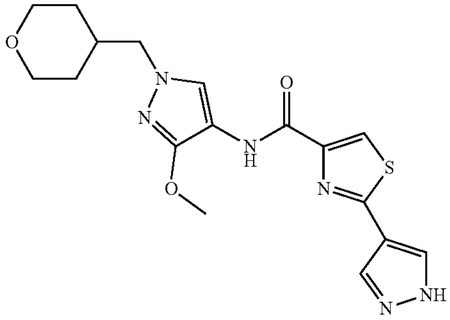 [SMILES: COc1nn(CC2CCOCC2)cc1NC(=O)c1csc(-c2cn[nH]c2)n1] | N-[3-methoxy-1-(tetrahydro-2H-pyran-4-ylmethyl)-1H-pyrazol-4-yl]-2-(1H-pyrazol-4-yl)-1,3-thiazole-4-carboxamide | calc'd 389, found 389 |

TABLE 10-continued

| Number | Structure | Name | Exact Mass [M + H]$^+$ |
|---|---|---|---|
| 7-17 | 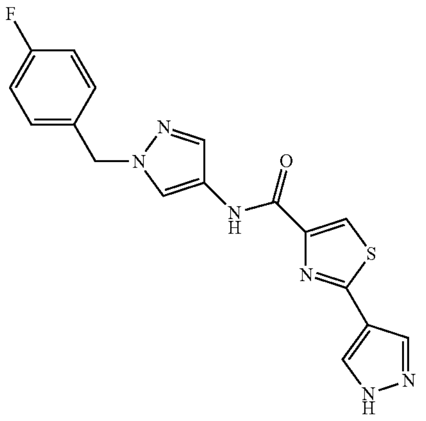 [SMILES: O=C(Nc1cnn(Cc2ccc(F)cc2)c1)c1csc(-c2cn[nH]c2)n1] | N-[1-(4-fluorobenzyl)-1H-pyrazol-4-yl]-2-(1H-pyrazol-4-yl)-1,3-thiazole-4-carboxamide | calc'd 369, found 369 |
| 7-18 | 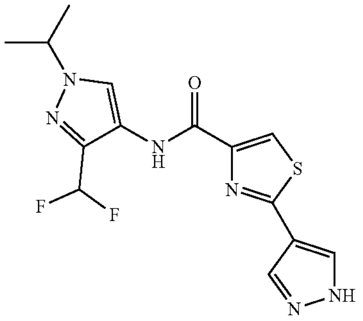 [SMILES: CC(C)n1cc(NC(=O)c2csc(-c3cn[nH]c3)n2)c(C(F)F)n1] | N-[3-(difluoromethyl)-1-(1-methylethyl)-1H-pyrazol-4-yl]-2-(1H-pyrazol-4-yl)-1,3-thiazole-4-carboxamide | calc'd 353, found 353 |
| 7-19 | 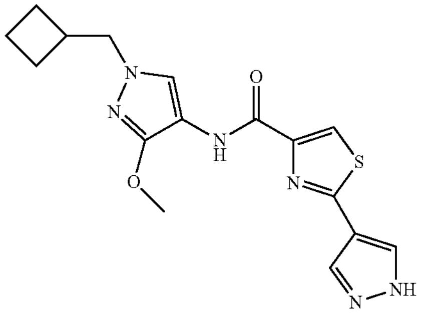 [SMILES: COc1nn(CC2CCC2)cc1NC(=O)c1csc(-c2cn[nH]c2)n1] | N-[1-(cyclobutylmethyl)-3-methoxy-1H-pyrazol-4-yl]-2-(1H-pyrazol-4-yl)-1,3-thiazole-4-carboxamide | calc'd 359, found 359 |
| 7-20 | 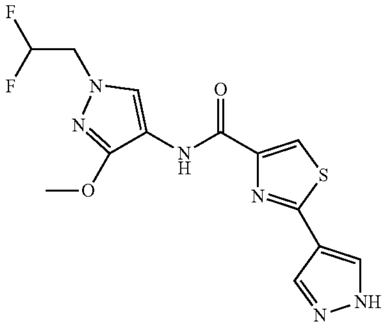 [SMILES: COc1nn(CC(F)F)cc1NC(=O)c1csc(-c2cn[nH]c2)n1] | N-[1-(2,2-difluoroethyl)-3-methoxy-1H-pyrazol-4-yl]-2-(1H-pyrazol-4-yl)-1,3-thiazole-4-carboxamide | calc'd 355, found 355 |

TABLE 10-continued

| Number | Structure | Name | Exact Mass [M + H]$^+$ |
|---|---|---|---|
| 7-21 | 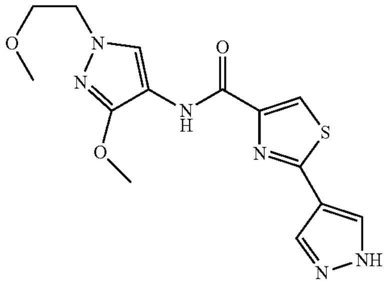 [SMILES: COCCn1cc(NC(=O)c2csc(-c3cn[nH]c3)n2)c(OC)n1] | N-[3-methoxy-1-(2-methoxyethyl)-1H-pyrazol-4-yl]-2-(1H-pyrazol-4-yl)-1,3-thiazole-4-carboxamide | calc'd 349, found 349 |
| 7-22 | 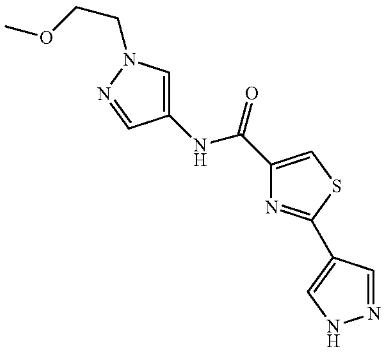 [SMILES: COCCn1cc(NC(=O)c2csc(-c3cn[nH]c3)n2)cn1] | N-[1-(2-methoxyethyl)-1H-pyrazol-4-yl]-2-(1H-pyrazol-4-yl)-1,3-thiazole-4-carboxamide | calc'd 319, found 319 |
| 7-23 | 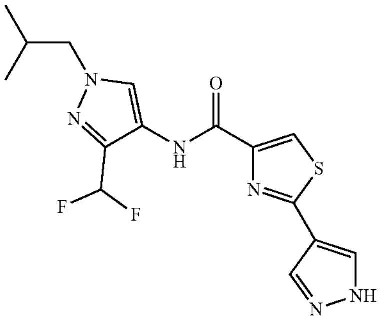 [SMILES: CC(C)Cn1cc(NC(=O)c2csc(-c3cn[nH]c3)n2)c(C(F)F)n1] | N-[3-(difluoromethyl)-1-(2-methylpropyl)-1H-pyrazol-4-yl]-2-(1H-pyrazol-4-yl)-1,3-thiazole-4-carboxamide | calc'd 367, found 367 |
| 7-24 | 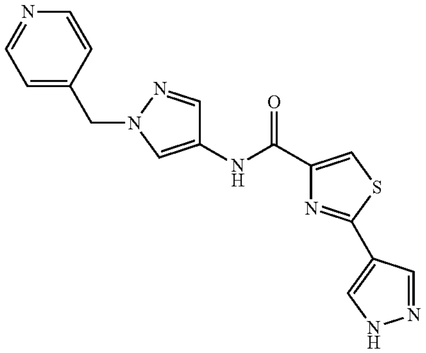 [SMILES: O=C(Nc1cnn(Cc2ccncc2)c1)c1csc(-c2cn[nH]c2)n1] | 2-(1H-pyrazol-4-yl)-N-[1-(pyridin-4-ylmethyl)-1H-pyrazol-4-yl]-1,3-thiazole-4-carboxamide | calc'd 352, found 352 |

TABLE 10-continued

| Number | Structure | Name | Exact Mass [M + H]$^+$ |
|---|---|---|---|
| 7-25 | 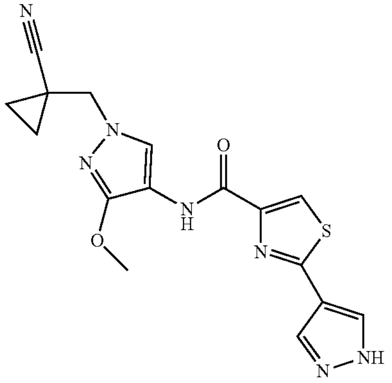 [SMILES: COc1nn(CC2(C#N)CC2)cc1NC(=O)c1csc(-c2cn[nH]c2)n1] | N-{1-[(1-cyanocyclopropyl) methyl]-3-methoxy-1H-pyrazol-4-yl}-2-(1H-pyrazol-4-yl)-1,3-thiazole-4-carboxamide | calc'd 370, found 370 |
| 7-26 | 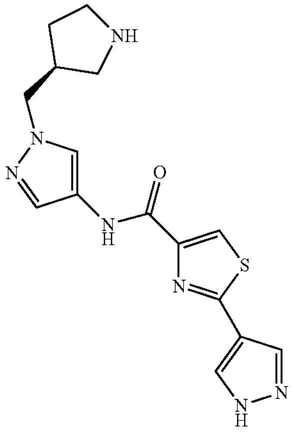 [SMILES: O=C(Nc1cnn(C[C@H]2CCNC2)c1)c1csc(-c2cn[nH]c2)n1] | 2-(1H-pyrazol-4-yl)-N-(1-{[(3S)-pyrrolidin-3-yl]methyl}-1H-pyrazol-4-yl)-1,3-thiazole-4-carboxamide | calc'd 344, found 344 |
| 7-27 | 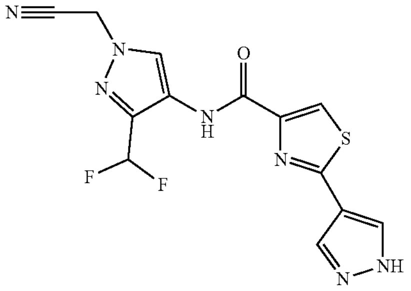 [SMILES: N#CCn1cc(NC(=O)c2csc(-c3cn[nH]c3)n2)c(C(F)F)n1] | N-[1-(cyanomethyl)-3-(difluoromethyl)-1H-pyrazol-4-yl]-2-(1H-pyrazol-4-yl)-1,3-thiazole-4-carboxamide | calc'd 350, found 350 |
| 7-28 | 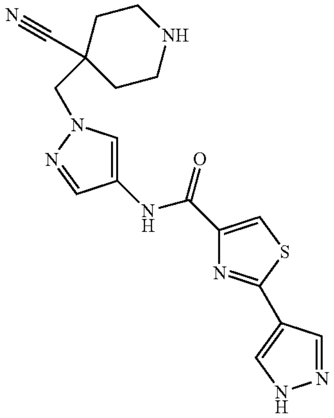 [SMILES: N#CC1(Cn2cc(NC(=O)c3csc(-c4cn[nH]c4)n3)cn2)CCNCC1] | N-{1-[(4-cyanopiperidin-4-yl)methyl]-1H-pyrazol-4-yl}-2-(1H-pyrazol-4-yl)-1,3-thiazole-4-carboxamide | calc'd 383, found 383 |

TABLE 10-continued

| Number | Structure | Name | Exact Mass [M + H]$^+$ |
|---|---|---|---|
| 7-29 | 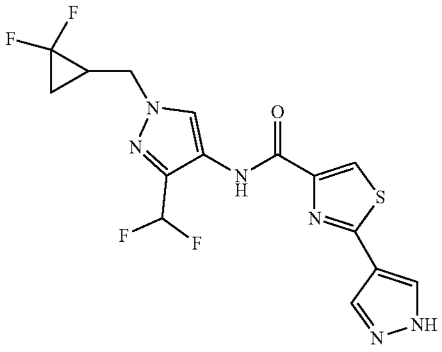 [SMILES: O=C(Nc1cn(CC2CC2(F)F)nc1C(F)F)c1csc(-c2cn[nH]c2)n1] | N-{1-[(2,2-difluorocyclopropyl)methyl]-3-(difluoromethyl)-1H-pyrazol-4-yl}-2-(1H-pyrazol-4-yl)-1,3-thiazole-4-carboxamide | calc'd 401, found 401 |
| 7-30 | 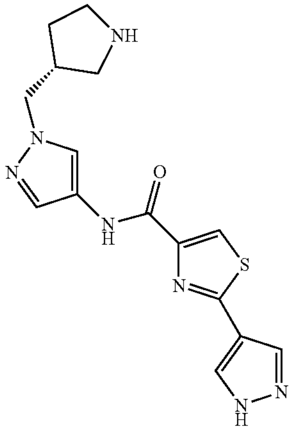 [SMILES: O=C(Nc1cnn(C[C@@H]2CCNC2)c1)c1csc(-c2cn[nH]c2)n1] | 2-(1H-pyrazol-4-yl)-N-(1-{[(3R)-pyrrolidin-3-yl]methyl}-1H-pyrazol-4-yl)-1,3-thiazole-4-carboxamide | calc'd 344, found 344 |
| 7-31 | 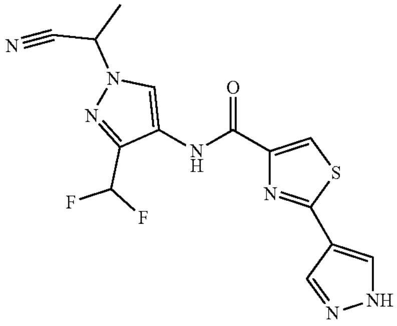 [SMILES: CC(C#N)n1cc(NC(=O)c2csc(-c3cn[nH]c3)n2)c(C(F)F)n1] | N-[1-(1-cyanoethyl)-3-(difluoromethyl)-1H-pyrazol-4-yl]-2-(1H-pyrazol-4-yl)-1,3-thiazole-4-carboxamide | calc'd 364, found 364 |
| 7-32 | 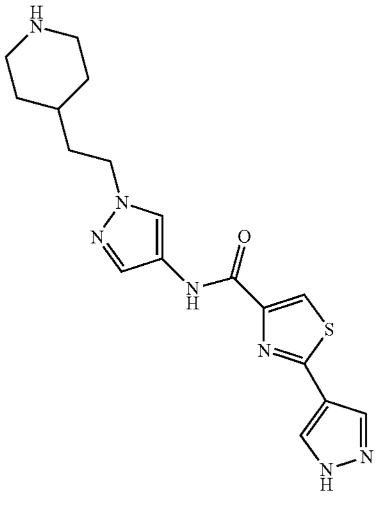 [SMILES: O=C(Nc1cnn(CCC2CCNCC2)c1)c1csc(-c2cn[nH]c2)n1] | N-{1-[2-(piperidin-4-yl)ethyl]-1H-pyrazol-4-yl}-2-(1H-pyrazol-4-yl)-1,3-thiazole-4-carboxamide | calc'd 372, found 372 |

TABLE 10-continued
| Number | Structure | Name | Exact Mass [M + H]+ |
|---|---|---|---|
| 7-33 | 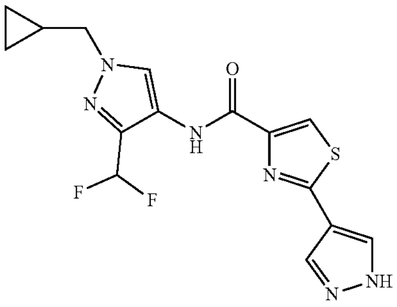 [SMILES: O=C(Nc1cn(CC2CC2)nc1C(F)F)c1csc(-c2cn[nH]c2)n1] | N-[1-(cyclopropylmethyl)-3-(difluoromethyl)-1H-pyrazol-4-yl]-2-(1H-pyrazol-4-yl)-1,3-thiazole-4-carboxamide | calc'd 365, found 365 |
| 7-34 | 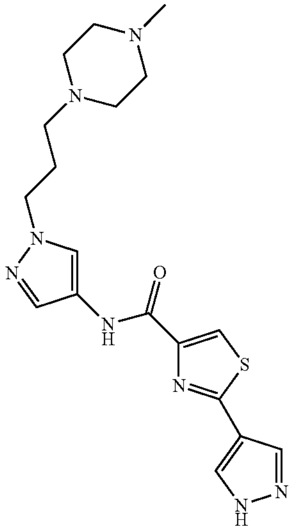 [SMILES: CN1CCN(CCCn2cc(NC(=O)c3csc(-c4cn[nH]c4)n3)cn2)CC1] | N-{1-[3-(4-methylpiperazin-1-yl)propyl]-1H-pyrazol-4-yl}-2-(1H-pyrazol-4-yl)-1,3-thiazole-4-carboxamide | calc'd 401, found 401 |
| 7-35 | 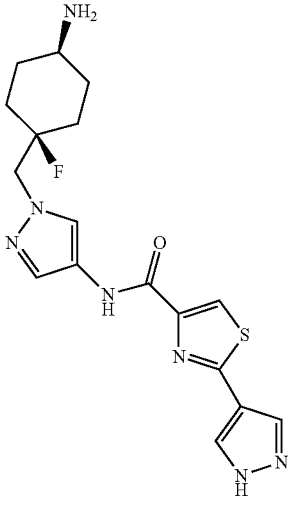 [SMILES: N[C@H]1CC[C@](F)(Cn2cc(NC(=O)c3csc(-c4cn[nH]c4)n3)cn2)CC1] | N-{1-[(cis-4-amino-1-fluorocyclohexyl)methyl]-1H-pyrazol-4-yl}-2-(1H-pyrazol-4-yl)-1,3-thiazole-4-carboxamide | calc'd 390, found 390 |

TABLE 10-continued
| Number | Structure | Name | Exact Mass [M + H]+ |
|---|---|---|---|
| 7-36 | 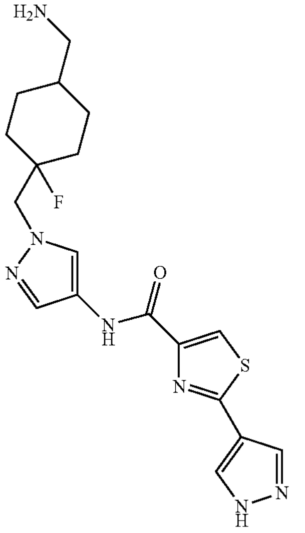 [SMILES: NCC1CCC(F)(Cn2cc(NC(=O)c3csc(-c4cn[nH]c4)n3)cn2)CC1] | N-(1-{[4-(aminomethyl)-1-fluorocyclohexyl]methyl}-1H-pyrazol-4-yl)-2-(1H-pyrazol-4-yl)-1,3-thiazole-4-carboxamide | calc'd 404, found 404 |
| 7-37 | 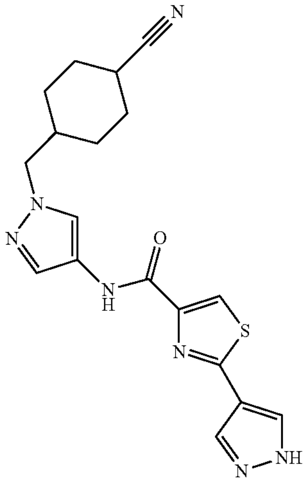 [SMILES: N#CC1CCC(Cn2cc(NC(=O)c3csc(-c4cn[nH]c4)n3)cn2)CC1] | N-{1-[(4-cyanocyclohexyl)methyl]-1H-pyrazol-4-yl}-2-(1H-pyrazol-4-yl)-1,3-thiazole-4-carboxamide | calc'd 382, found 382 |
| 7-38 | 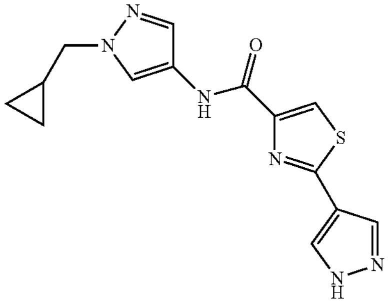 [SMILES: O=C(Nc1cnn(CC2CC2)c1)c1csc(-c2cn[nH]c2)n1] | N-[1-(cyclopropylmethyl)-1H-pyrazol-4-yl]-2-(1H-pyrazol-4-yl)-1,3-thiazole-4-carboxamide | calc'd 315, found 315 |

TABLE 10-continued

| Number | Structure | Name | Exact Mass [M + H]+ |
|---|---|---|---|
| 7-39 | 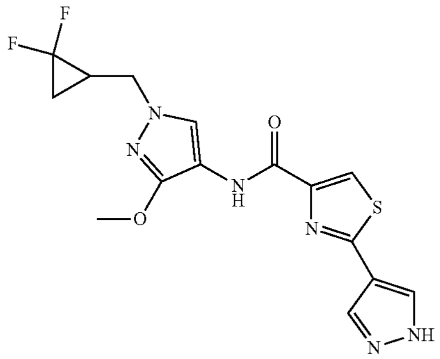 [SMILES: COc1nn(CC2CC2(F)F)cc1NC(=O)c1csc(-c2cn[nH]c2)n1] | N-{1-[(2,2-difluorocyclopropyl)methyl]-3-methoxy-1H-pyrazol-4-yl}-2-(1H-pyrazol-4-yl)-1,3-thiazole-4-carboxamide | calc'd 381, found 381 |
| 7-40 | 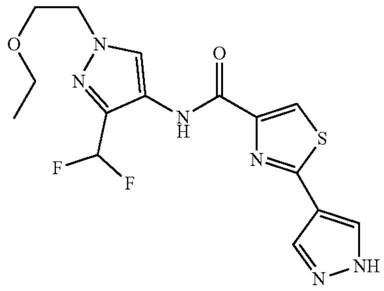 [SMILES: CCOCCn1cc(NC(=O)c2csc(-c3cn[nH]c3)n2)c(C(F)F)n1] | N-[3-(difluoromethyl)-1-(2-ethoxyethyl)-1H-pyrazol-4-yl]-2-(1H-pyrazol-4-yl)-1,3-thiazole-4-carboxamide | calc'd 383, found 383 |
| 7-41 | 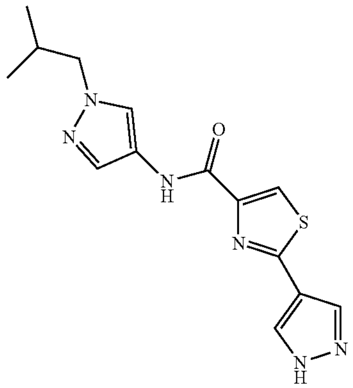 [SMILES: CC(C)Cn1cc(NC(=O)c2csc(-c3cn[nH]c3)n2)cn1] | N-[1-(2-methylpropyl)-1H-pyrazol-4-yl]-2-(1H-pyrazol-4-yl)-1,3-thiazole-4-carboxamide | calc'd 317, found 317 |
| 7-42 | 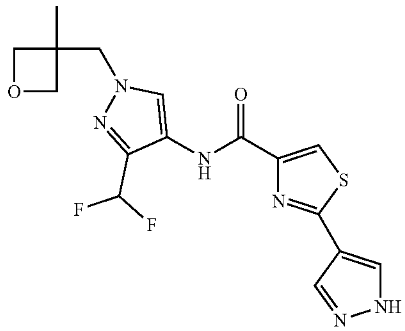 [SMILES: CC1(Cn2cc(NC(=O)c3csc(-c4cn[nH]c4)n3)c(C(F)F)n2)COC1] | N-{3-(difluoromethyl)-1-[(3-methyloxetan-3-yl)methyl]-1H-pyrazol-4-yl}-2-(1H-pyrazol-4-yl)-1,3-thiazole-4-carboxamide | calc'd 395, found 395 |

TABLE 10-continued

| Number | Structure | Name | Exact Mass [M + H]+ |
|---|---|---|---|
| 7-43 | 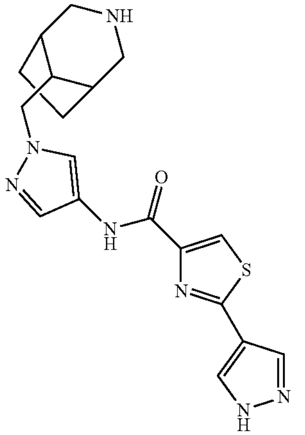 [SMILES: O=C(Nc1cnn(CC2C3CCC2CNC3)c1)c1csc(-c2cn[nH]c2)n1] | N-{1-[(3-azabicyclo[3.2.1]octan-8-yl)methyl]-1H-pyrazol-4-yl}-2-(1H-pyrazol-4-yl)-1,3-thiazole-4-carboxamide | calc'd 384, found 384 |

Preparation of Example 8-1

Scheme 19. Synthesis of N-(1-(2-methylpyridin-4-yl)-1H-pyrazol-4-yl)-2-(1H-pyrazol-4-yl)thiazole-4-carboxamide

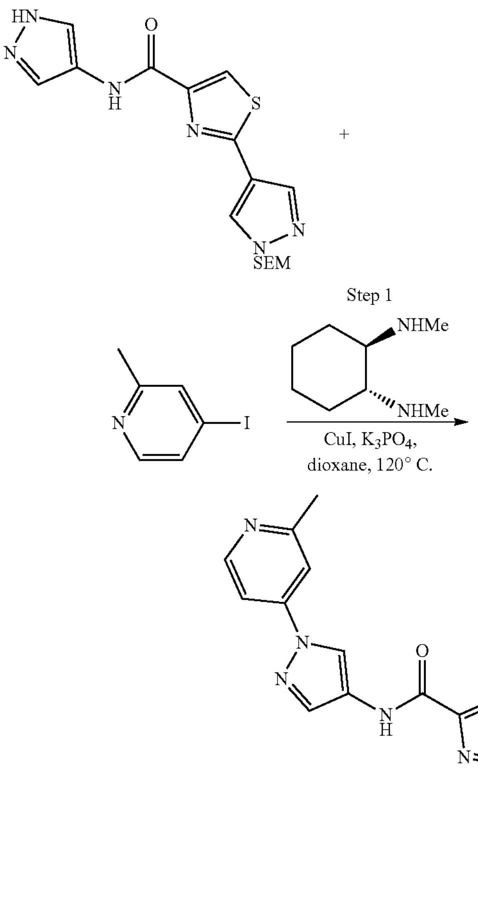

-continued

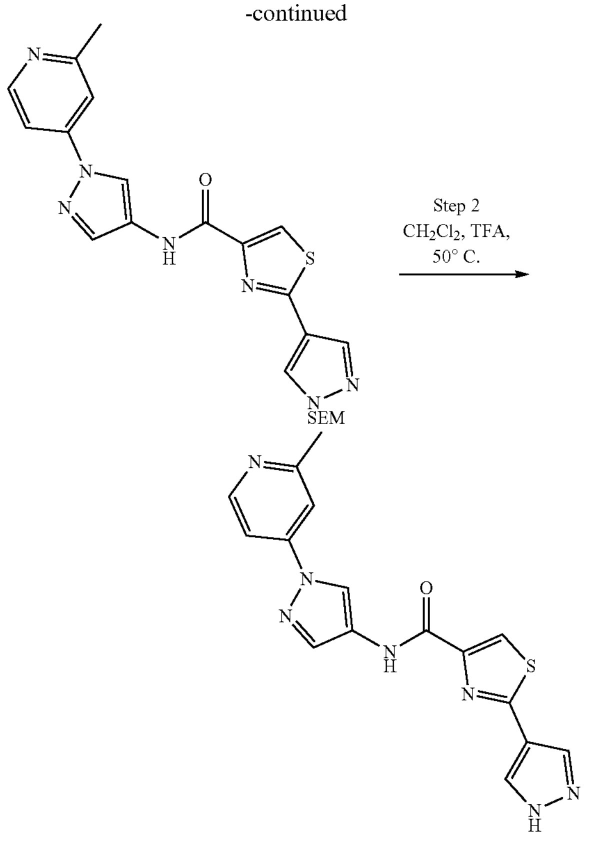

Example 8-1. N-(1-(2-Methylpyridin-4-yl)-1H-pyrazol-4-yl)-2-(1H-pyrazol-4-yl)thiazole-4-carboxamide Step 1: To a mixture of 4-bromo-2-methylpyridine (22 mg, 0.13 mmol), CuI (1.2 mg, 0.006 mmol), $K_3PO_4$ (40.8 mg, 0.19 mmol), (S,S)-(−)-N,N'-dimethyl-1,2-cyclohexane-diamine (1.8 mg, 0.013 mmol), and N-(1H-pyrazol-4-yl)-2-(1-((2-(trimethylsilyl)ethoxy)methyl)-1H-pyrazol-4-yl)thiazole-4-carboxamide (Intermediate 20, 25 mg, 0.064 mmol) was added dioxane (1 mL). The resulting suspension was put under an atmosphere of $N_2$ and was heated to 120° C. for 16 h, and then cooled to rt. The reaction mixture was concentrated to dryness in vacuo to afford crude N-(1-(2-methylpyridin-4-yl)-1H-pyrazol-4-yl)-2-(1-((2-(trimethylsilyl)ethoxy)methyl)-1H-pyrazol-4-yl)thiazole-4-carboxamide. MS (ESI) m/z $C_{22}H_{28}N_7O_2SSi$ $[M+H]^+$ calc'd 482. found 482.

Step 2: To crude N-(1-(2-methylpyridin-4-yl)-1H-pyrazol-4-yl)-2-(1-((2-(trimethylsilyl)ethoxy)methyl)-1H-pyrazol-4-yl)thiazole-4-carboxamide was added $CH_2Cl_2$ (0.8 mL) and TFA (0.74 mL, 9.6 mmol), and the reaction mixture was heated to 50° C. for 1.5 h, and then cooled to rt. The reaction mixture was concentrated to dryness in vacuo. The crude residue was re-dissolved in DMSO, filtered, and purified by preparative HPLC (reversed phase, MeCN/water with 0.1% TFA modifier) to afford N-(1-(2-methylpyridin-4-yl)-1H-pyrazol-4-yl)-2-(1H-pyrazol-4-yl)thiazole-4-carboxamide, TFA. MS (ESI) m/z $C_{16}H_{14}N_7OS$ $[M+H]^+$ calc'd 352. found 352. $^1H$ NMR (500 MHz, DMSO-$d_6$) δ 10.79 (s, 1H), 9.09 (s, 1H), 8.73 (s, 1H), 8.33 (s, 1H), 8.30 (s, 1H), 8.26 (s, 1H), 8.23-8.17 (m, 1H), 8.11-8.04 (m, 1H), 2.68 (s, 3H).

Compounds in Table 11 below were prepared from Intermediate 20 using procedures analogous to those described in Scheme 19.

TABLE 11

| Number | Structure | Name | Exact Mass $[M + H]^+$ |
|---|---|---|---|
| 8-2 | 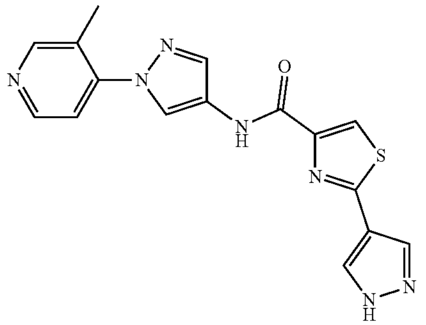 [SMILES: Cc1cnccc1-n1cc(NC(=O)c2csc(-c3cn[nH]c3)n2)cn1] | N-[1-(3-methylpyridin-4-yl)-1H-pyrazol-4-yl]-2-(1H-pyrazol-4-yl)-1,3-thiazole-4-carboxamide | calc'd 352, found 352 |
| 8-3 | 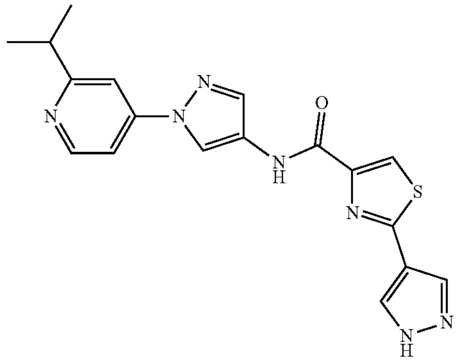 [SMILES: CC(C)c1cc(-n2cc(NC(=O)c3csc(-c4cn[nH]c4)n3)cn2)ccn1] | N-{1-[2-(1-methylethyl)pyridin-4-yl]-1H-pyrazol-4-yl}-2-(1H-pyrazol-4-yl)-1,3-thiazole-4-carboxamide | calc'd 380, found 380 |
| 8-4 | 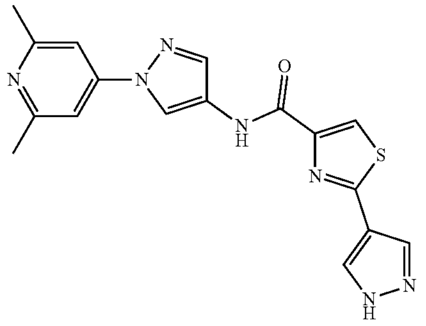 [SMILES: Cc1cc(-n2cc(NC(=O)c3csc(-c4cn[nH]c4)n3)cn2)cc(C)n1] | N-[1-(2,6-dimethylpyridin-4-yl)-1H-pyrazol-4-yl]-2-(1H-pyrazol-4-yl)-1,3-thiazole-4-carboxamide | calc'd 366, found 366 |

Preparation of Example 9-1

Scheme 20. Synthesis of N-(1-cyclobutyl-1H-pyrazol-4-yl)-6-(1-methyl-1H-pyrazol-4-yl)picolinamide

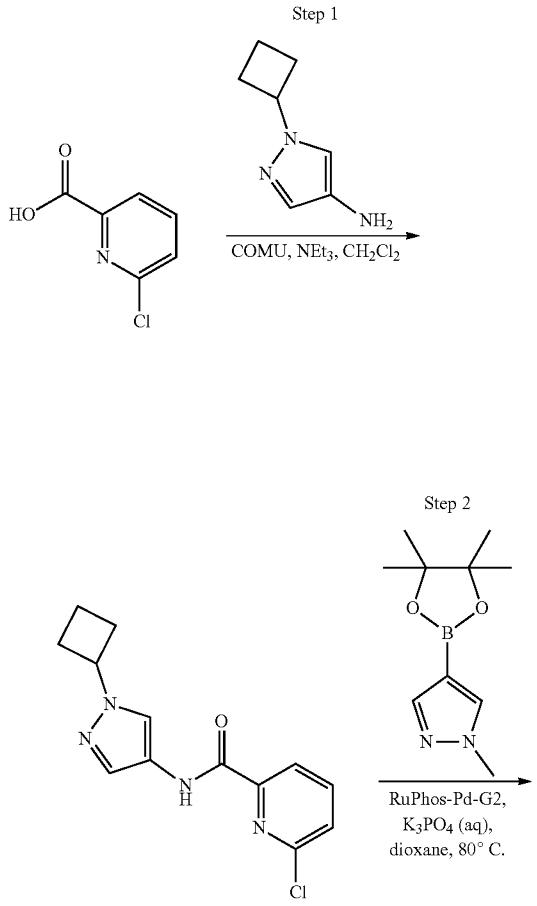

-continued

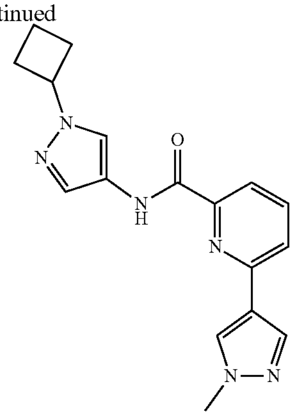

Example 9-1. N-(1-Cyclobutyl-1H-pyrazol-4-yl)-6-(1-methyl-1H-pyrazol-4-yl)picolinamide Step 1: To a mixture of 6-chloropicolinic acid (24 mg, 0.15 mmol), COMU (64 mg, 0.15 mmol), and $CH_2Cl_2$ (1 mL) was added $NEt_3$ (84 μL, 0.60 mmol). The resulting solution was stirred at rt for 2 h. To the crude reaction mixture was added water. The phases were separated, and the aqueous layer was extracted thrice with $CH_2Cl_2$. The combined organic layers were dried over $Na_2SO_4$, filtered, and concentrated to dryness in vacuo to afford crude 6-chloro-N-(1-cyclobutyl-1H-pyrazol-4-yl)picolinamide. MS (ESI) m/z $C_{13}H_{14}ClN_4O$ $[M+H]^+$ calc'd 277. found 277.

Step 2: To a mixture of crude 6-chloro-N-(1-cyclobutyl-1H-pyrazol-4-yl)picolinamide (41.5 mg, 0.15 mmol), RuPhos-Pd-G2 (11.8 mg, 0.015 mmol), 1-methyl-4-(4,4,5,5-tetramethyl-1,3,2-dioxaborolan-2-yl)-1H-pyrazole (46.8 mg, 0.23 mmol), and dioxane (0.75 mL) was added aqueous $K_3PO_4$ (0.23 mL, 2 M in water, 0.45 mmol). The reaction vessel was purged with nitrogen thrice, and then heated to 80° C. overnight, and then cooled to rt. The crude reaction mixture was diluted with DMSO, filtered, and purified by preparative HPLC (reversed phase, MeCN/water with 0.1% TFA modifier) to afford N-(1-cyclobutyl-1H-pyrazol-4-yl)-6-(1-methyl-1H-pyrazol-4-yl)picolinamide, TFA. MS (ESI) m/z $C_{17}H_{19}N_6O$ $[M+H]^+$ calc'd 323. found 323. $^1H$ NMR (500 MHz, DMSO-$d_6$) δ 10.58 (s, 1H), 8.59 (s, 1H), 8.34 (s, 1H), 8.20 (s, 1H), 7.97 (s, 1H), 7.86 (s, 1H), 7.81 (s, 1H), 4.90-4.76 (m, 1H), 3.93 (s, 3H), 2.47-2.30 (m, 4H), 1.86-1.70 (m, 2H).

Compounds in Table 12 below were prepared using procedures analogous to those described in Scheme 20.

TABLE 12

| Number | Structure | Name | Exact Mass $[M + H]^+$ |
|---|---|---|---|
| 9-2 | 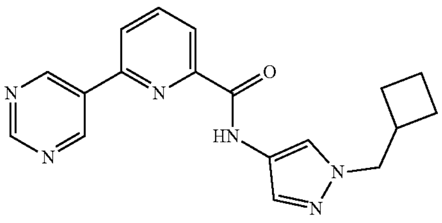 [SMILES: O=C(Nc1cnn(CC2CCC2)c1)c1cccc(-c2cncnc2)n1] | N-[1-(cyclobutylmethyl)-1H-pyrazol-4-yl]-6-pyrimidin-5-ylpyridine-2-carboxamide | calc'd 335, found 335 |

TABLE 12-continued

| Number | Structure | Name | Exact Mass [M + H]$^+$ |
|---|---|---|---|
| 9-3 | 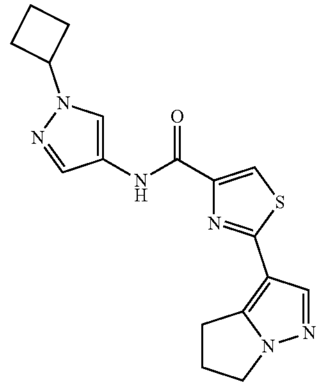 [SMILES: O=C(Nc1cnn(C2CCC2)c1)c1csc(-c2cnn3c2CCC3)n1] | N-(1-cyclobutyl-1H-pyrazol-4-yl)-2-(5,6-dihydro-4H-pyrrolo[1,2-b]pyrazol-3-yl)-1,3-thiazole-4-carboxamide | calc'd 355, found 355 |
| 9-4 | 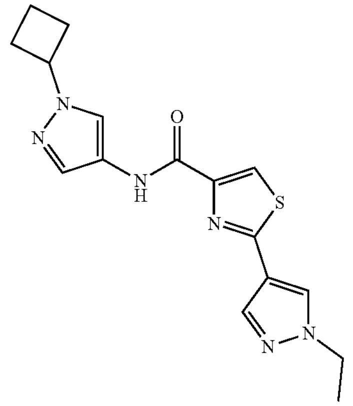 [SMILES: CCn1cc(-c2nc(C(=O)Nc3cnn(C4CCC4)c3)cs2)cn1] | N-(1-cyclobutyl-1H-pyrazol-4-yl)-2-(1-ethyl-1H-pyrazol-4-yl)-1,3-thiazole-4-carboxamide | calc'd 343, found 343 |
| 9-5 | 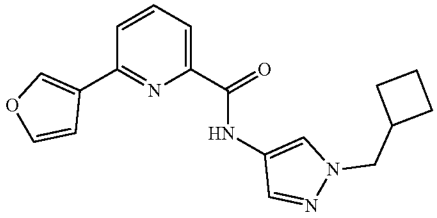 [SMILES: O=C(Nc1cnn(CC2CCC2)c1)c1cccc(-c2ccoc2)n1] | N-[1-(cyclobutylmethyl)-1H-pyrazol-4-yl]-6-furan-3-ylpyridine-2-carboxamide | calc'd 323, found 323 |
| 9-6 | 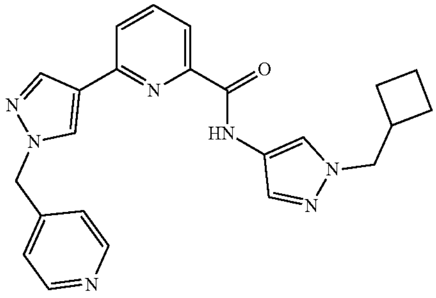 [SMILES: O=C(Nc1cnn(CC2CCC2)c1)c1cccc(-c2cnn(Cc3ccncc3)c2)n1] | N-[1-(cyclobutylmethyl)-1H-pyrazol-4-yl]-6-[1-(pyridin-4-ylmethyl)-1H-pyrazol-4-yl]pyridine-2-carboxamide | calc'd 414, found 414 |

TABLE 12-continued

| Number | Structure | Name | Exact Mass [M + H]$^+$ |
|---|---|---|---|
| 9-7 | 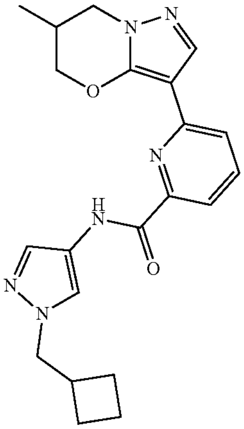 [SMILES: CC1COc2c(-c3cccc(C(=O)Nc4cnn(CC5CCC5)c4)n3)cnn2C1] | N-[1-(cyclobutylmethyl)-1H-pyrazol-4-yl]-6-(6-methyl-6,7-dihydro-5H-pyrazolo[5,1-b][1,3]oxazin-3-yl)pyridine-2-carboxamide | calc'd 393, found 393 |
| 9-8 | 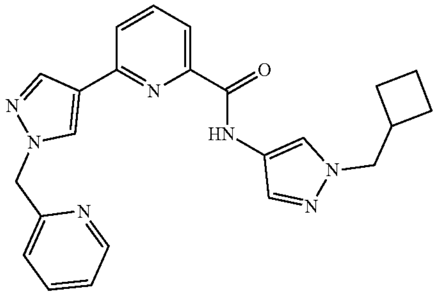 [SMILES: O=C(Nc1cnn(CC2CCC2)c1)c1cccc(-c2cnn(Cc3ccccn3)c2)n1] | N-[1-(cyclobutylmethyl)-1H-pyrazol-4-yl]-6-[1-(pyridin-2-ylmethyl)-1H-pyrazol-4-yl]pyridine-2-carboxamide | calc'd 414, found 414 |
| 9-9 | 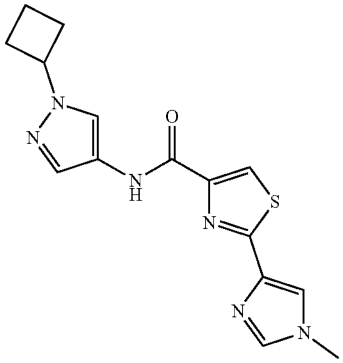 [SMILES: Cn1cnc(-c2nc(C(=O)Nc3cnn(C4CCC4)c3)cs2)c1] | N-(1-cyclobutyl-1H-pyrazol-4-yl)-2-(1-methyl-1H-imidazol-4-yl)-1,3-thiazole-4-carboxamide | calc'd 329, found 329 |
| 9-10 | 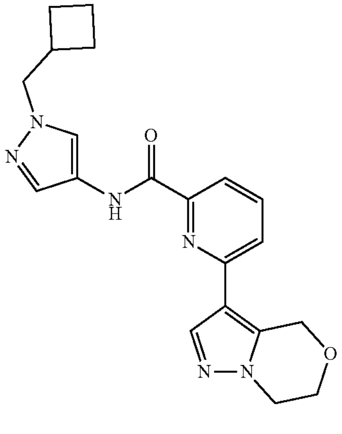 [SMILES: O=C(Nc1cnn(CC2CCC2)c1)c1cccc(-c2cnn3c2COCC3)n1] | N-[1-(cyclobutylmethyl)-1H-pyrazol-4-yl]-6-(6,7-dihydro-4H-pyrazolo[5,1-c][1,4]oxazin-3-yl)pyridine-2-carboxamide | calc'd 379, found 379 |

TABLE 12-continued

| Number | Structure | Name | Exact Mass [M + H]$^+$ |
|---|---|---|---|
| 9-11 | 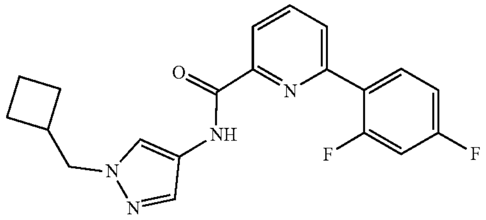 [SMILES: O=C(Nc1cnn(CC2CCC2)c1)c1cccc(-c2ccc(F)cc2F)n1] | N-[1-(cyclobutylmethyl)-1H-pyrazol-4-yl]-6-(2,4-difluorophenyl) pyridine-2-carboxamide | calc'd 369, found 369 |
| 9-12 | 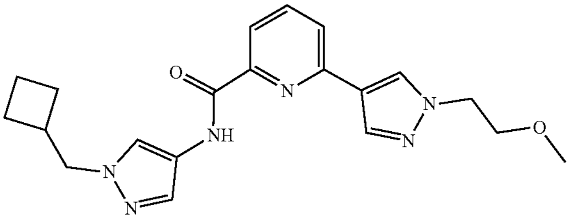 [SMILES: COCCn1cc(-c2cccc(C(=O)Nc3cnn(CC4CCC4)c3)n2)cn1] | N-[1-(cyclobutylmethyl)-1H-pyrazol-4-yl]-6-[1-(2-methoxyethyl)-1H-pyrazol-4-yl]pyridine-2-carboxamide | calc'd 381, found 381 |
| 9-13 | 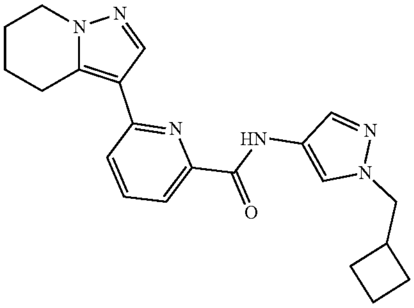 [SMILES: O=C(Nc1cnn(CC2CCC2)c1)c1cccc(-c2cnn3c2CCCC3)n1] | N-[1-(cyclobutylmethyl)-1H-pyrazol-4-yl]-6-(4,5,6,7-tetrahydropyrazolo [1,5-a]pyridin-3-yl)pyridine-2-carboxamide | calc'd 377, found 377 |
| 9-14 | 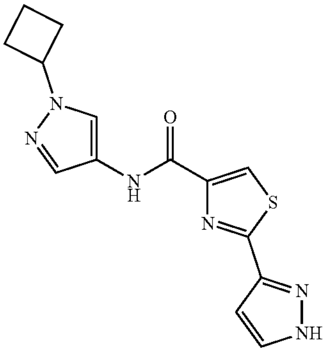 [SMILES: O=C(Nc1cnn(C2CCC2)c1)c1csc(-c2cc[nH]n2)n1] | N-(1-cyclobutyl-1H-pyrazol-4-yl)-2-(1H-pyrazol-3-yl)-1,3-thiazole-4-carboxamide | calc'd 315, found 315 |
| 9-15 | 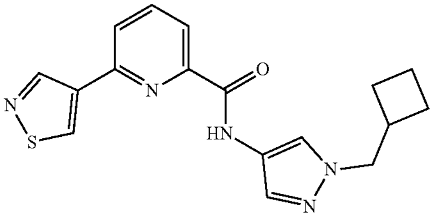 [SMILES: O=C(Nc1cnn(CC2CCC2)c1)c1cccc(-c2cnsc2)n1] | N-[1-(cyclobutylmethyl)-1H-pyrazol-4-yl]-6-isothiazol-4-ylpyridine-2-carboxamide | calc'd 340, found 340 |

TABLE 12-continued

| Number | Structure | Name | Exact Mass [M + H]$^+$ |
| --- | --- | --- | --- |
| 9-16 | 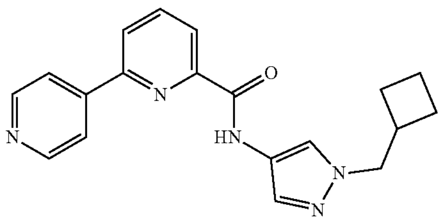 [SMILES: O=C(Nc1cnn(CC2CCC2)c1)c1cccc(-c2ccncc2)n1] | N-[1-(cyclobutylmethyl)-1H-pyrazol-4-yl]-2,4'-bipyridine-6-carboxamide | calc'd 334, found 334 |
| 9-17 | 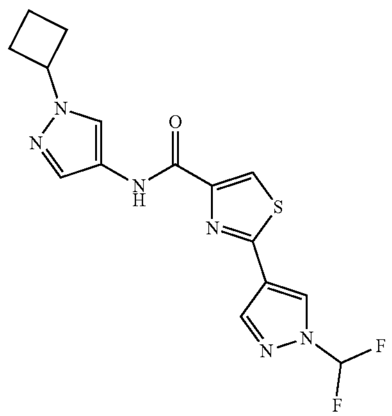 [SMILES: O=C(Nc1cnn(C2CCC2)c1)c1csc(-c2cnn(C(F)F)c2)n1] | N-(1-cyclobutyl-1H-pyrazol-4-yl)-2-[1-(difluoromethyl)-1H-pyrazol-4-yl]-1,3-thiazole-4-carboxamide | calc'd 365, found 365 |
| 9-18 | 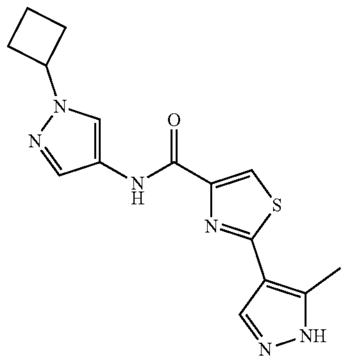 [SMILES: Cc1[nH]ncc1-c1nc(C(=O)Nc2cnn(C3CCC3)c2)cs1] | N-(1-cyclobutyl-1H-pyrazol-4-yl)-2-(5-methyl-1H-pyrazol-4-yl)-1,3-thiazole-4-carboxamide | calc'd 329, found 329 |
| 9-19 | 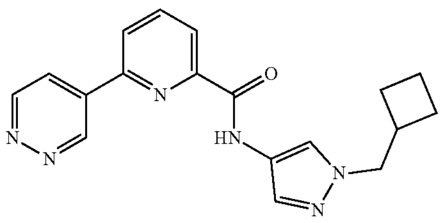 [SMILES: O=C(Nc1cnn(CC2CCC2)c1)c1cccc(-c2ccnnc2)n1] | N-[1-(cyclobutylmethyl)-1H-pyrazol-4-yl]-6-pyridazin-4-ylpyridine-2-carboxamide | calc'd 335, found 335 |
| 9-20 | 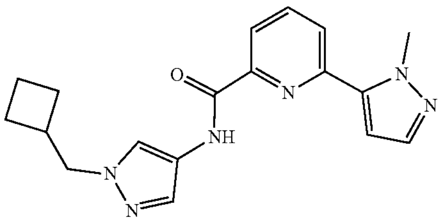 [SMILES: Cn1nccc1-c1cccc(C(=O)Nc2cnn(CC3CCC3)c2)n1] | N-[1-(cyclobutylmethyl)-1H-pyrazol-4-yl]-6-(1-methyl-1H-pyrazol-5-yl)pyridine-2-carboxamide | calc'd 337, found 337 |

TABLE 12-continued

| Number | Structure | Name | Exact Mass [M + H]$^+$ |
| --- | --- | --- | --- |
| 9-21 | 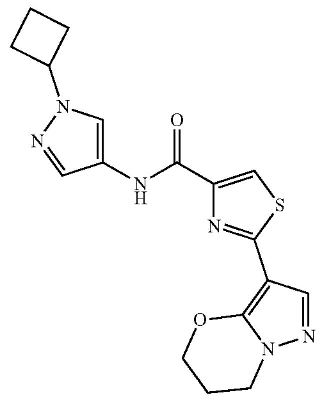 [SMILES: O=C(Nc1cnn(C2CCC2)c1)c1csc(-c2cnn3c2OCCC3)n1] | N-(1-cyclobutyl-1H-pyrazol-4-yl)-2-(6,7-dihydro-5H-pyrazolo[5,1-b][1,3]oxazin-3-yl)-1,3-thiazole-4-carboxamide | calc'd 371, found 371 |
| 9-22 | 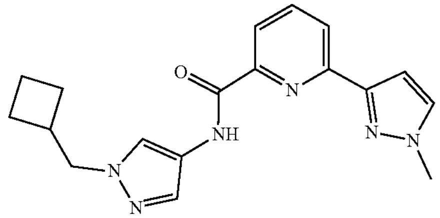 [SMILES: Cn1ccc(-c2cccc(C(=O)Nc3cnn(CC4CCC4)c3)n2)n1] | N-[1-(cyclobutylmethyl)-1H-pyrazol-4-yl]-6-(1-methyl-1H-pyrazol-3-yl)pyridine-2-carboxamide | calc'd 337, found 337 |
| 9-23 | 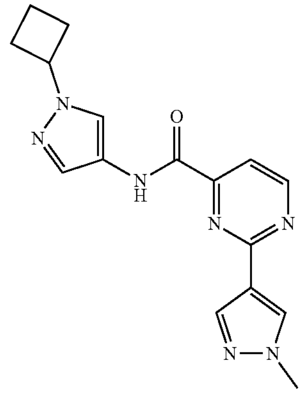 [SMILES: Cn1cc(-c2nccc(C(=O)Nc3cnn(C4CCC4)c3)n2)cn1] | N-(1-cyclobutyl-1H-pyrazol-4-yl)-2-(1-methyl-1H-pyrazol-4-yl)pyrimidine-4-carboxamide | calc'd 324, found 324 |
| 9-24 | 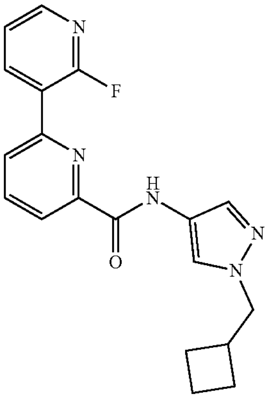 [SMILES: O=C(Nc1cnn(CC2CCC2)c1)c1cccc(-c2cccnc2F)n1] | N-[1-(cyclobutylmethyl)-1H-pyrazol-4-yl]-2'-fluoro-2,3'-bipyridine-6-carboxamide | calc'd 352, found 352 |

TABLE 12-continued

| Number | Structure | Name | Exact Mass [M + H]+ |
|---|---|---|---|
| 9-25 | 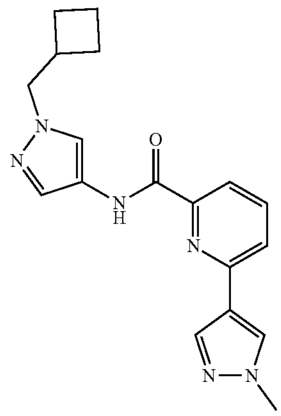 [SMILES: Cn1cc(-c2cccc(C(=O)Nc3cnn(CC4CCC4)c3)n2)cn1] | N-[1-(cyclobutylmethyl)-1H-pyrazol-4-yl]-6-(1-methyl-1H-pyrazol-4-yl)pyridine-2-carboxamide | calc'd 337, found 337 |
| 9-26 | 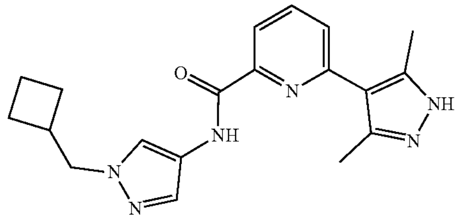 [SMILES: Cc1n[nH]c(C)c1-c1cccc(C(=O)Nc2cnn(CC3CCC3)c2)n1] | N-[1-(cyclobutylmethyl)-1H-pyrazol-4-yl]-6-(3,5-dimethyl-1H-pyrazol-4-yl)pyridine-2-carboxamide | calc'd 351, found 351 |
| 9-27 | 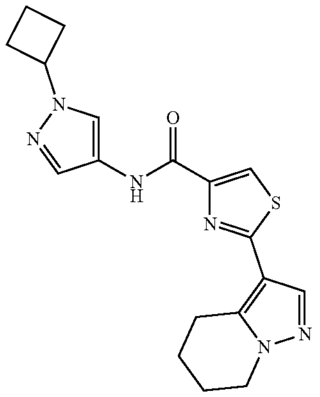 [SMILES: O=C(Nc1cnn(C2CCC2)c1)c1csc(-c2cnn3c2CCCC3)n1] | N-(1-cyclobutyl-1H-pyrazol-4-yl)-2-(4,5,6,7-tetrahydropyrazolo[1,5-a]pyridin-3-yl)-1,3-thiazole-4-carboxamide | calc'd 369, found 369 |
| 9-28 | 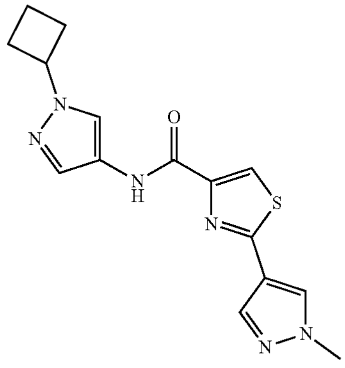 [SMILES: Cn1cc(-c2nc(C(=O)Nc3cnn(C4CCC4)c3)cs2)cn1] | N-(1-cyclobutyl-1H-pyrazol-4-yl)-2-(1-methyl-1H-pyrazol-4-yl)-1,3-thiazole-4-carboxamide | calc'd 329, found 329 |

TABLE 12-continued

| Number | Structure | Name | Exact Mass [M + H]$^+$ |
|---|---|---|---|
| 9-29 | 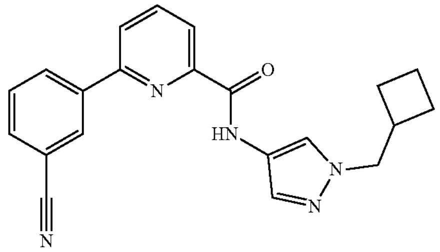 [SMILES: N#Cc1cccc(-c2cccc(C(=O)Nc3cnn(CC4CCC4)c3)n2)c1] | 6-(3-cyanophenyl)-N-[1-(cyclobutylmethyl)-1H-pyrazol-4-yl]pyridine-2-carboxamide | calc'd 358, found 358 |
| 9-30 | 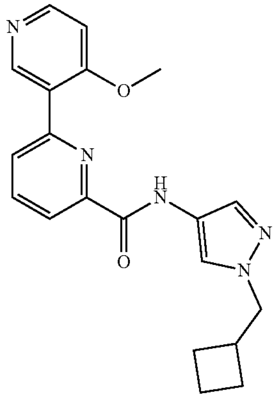 [SMILES: COc1ccncc1-c1cccc(C(=O)Nc2cnn(CC3CCC3)c2)n1] | N-[1-(cyclobutylmethyl)-1H-pyrazol-4-yl]-4'-methoxy-2,3'-bipyridine-6-carboxamide | calc'd 364, found 364 |
| 9-31 | 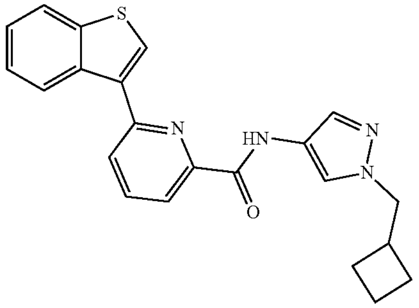 [SMILES: O=C(Nc1cnn(CC2CCC2)c1)c1cccc(-c2csc3ccccc23)n1] | 6-(1-benzothiophen-3-yl)-N-[1-(cyclobutylmethyl)-1H-pyrazol-4-yl]pyridine-2-carboxamide | calc'd 389, found 389 |
| 9-32 | 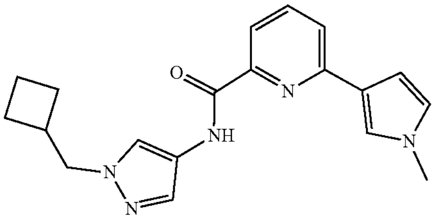 [SMILES: Cn1ccc(-c2cccc(C(=O)Nc3cnn(CC4CCC4)c3)n2)c1] | N-[1-(cyclobutylmethyl)-1H-pyrazol-4-yl]-6-(1-methyl-1H-pyrrol-3-yl)pyridine-2-carboxamide | calc'd 336, found 336 |
| 9-33 | 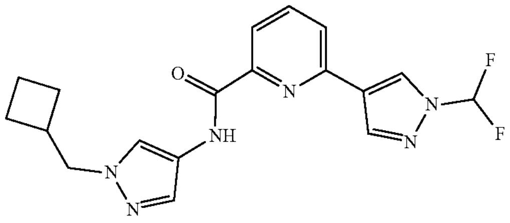 [SMILES: O=C(Nc1cnn(CC2CCC2)c1)c1cccc(-c2cnn(C(F)F)c2)n1] | N-[1-(cyclobutylmethyl)-1H-pyrazol-4-yl]-6-[1-(difluoromethyl)-1H-pyrazol-4-yl]pyridine-2-carboxamide | calc'd 373, found 373 |

TABLE 12-continued

| Number | Structure | Name | Exact Mass [M + H]+ |
|---|---|---|---|
| 9-34 | 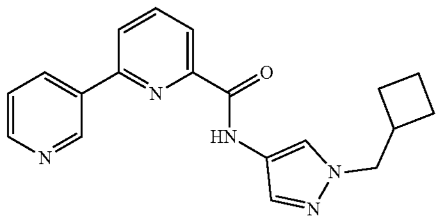 [SMILES: O=C(Nc1cnn(CC2CCC2)c1)c1cccc(-c2cccnc2)n1] | N-[1-(cyclobutylmethyl)-1H-pyrazol-4-yl]-2,3'-bipyridine-6-carboxamide | calc'd 334, found 334 |
| 9-35 | 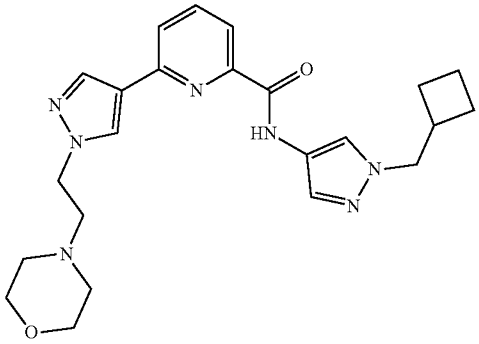 [SMILES: O=C(Nc1cnn(CC2CCC2)c1)c1cccc(-c2cnn(CCN3CCOCC3)c2)n1] | N-[1-(cyclobutylmethyl)-1H-pyrazol-4-yl]-6-[1-(2-morpholin-4-ylethyl)-1H-pyrazol-4-yl]pyridine-2-carboxamide | calc'd 436, found 436 |
| 9-36 | 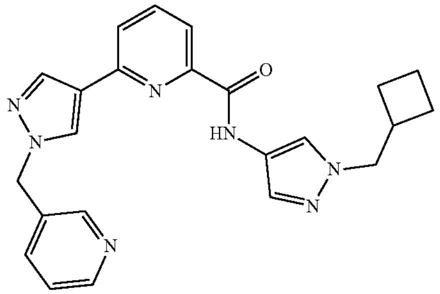 [SMILES: O=C(Nc1cnn(CC2CCC2)c1)c1cccc(-c2cnn(Cc3cccnc3)c2)n1] | N-[1-(cyclobutylmethyl)-1H-pyrazol-4-yl]-6-[1-(pyridin-3-ylmethyl)-1H-pyrazol-4-yl]pyridine-2-carboxamide | calc'd 414, found 414 |
| 9-37 | 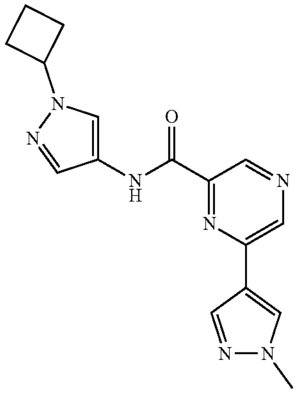 [SMILES: Cn1cc(-c2cncc(C(=O)Nc3cnn(C4CCC4)c3)n2)cn1] | N-(1-cyclobutyl-1H-pyrazol-4-yl)-6-(1-methyl-1H-pyrazol-4-yl)pyrazine-2-carboxamide | calc'd 438, found 438 |

TABLE 12-continued
| Number | Structure | Name | Exact Mass [M + H]$^+$ |
| --- | --- | --- | --- |
| 9-38 | 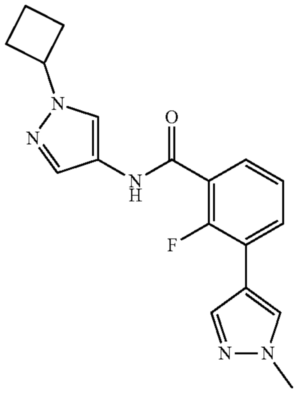 [SMILES: Cn1cc(-c2cccc(C(=O)Nc3cnn(C4CCC4)c3)c2F)cn1] | N-(1-cyclobutyl-1H-pyrazol-4-yl)-2-fluoro-3-(1-methyl-1H-pyrazol-4-yl)benzamide | calc'd 340, found 340 |
| 9-39 | 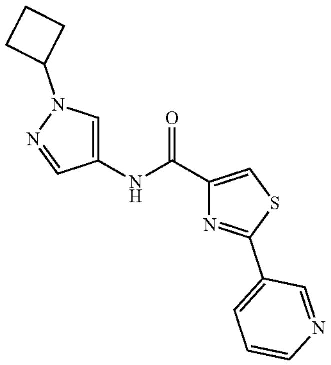 [SMILES: O=C(Nc1cnn(C2CCC2)c1)c1csc(-c2cccnc2)n1] | N-(1-cyclobutyl-1H-pyrazol-4-yl)-2-(pyridin-3-yl)thiazole-4-carboxamide | calc'd 326, found 326 |
| 9-40 | 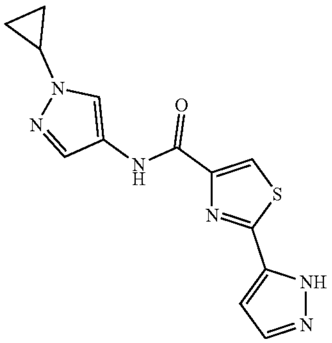 [SMILES: O=C(Nc1cnn(C2CC2)c1)c1csc(-c2ccn[nH]2)n1] | N-(1-cyclopropyl-1H-pyrazol-4-yl)-2-(1H-pyrazol-5-yl)thiazole-4-carboxamide | calc'd 301, found 301 |

Preparation of Example 10-1

Scheme 21. Synthesis of 6-(1-cyanocyclopropyl)-N-(1-(cyclobutylmethyl)-1H-pyrazol-4-yl)picolinamide

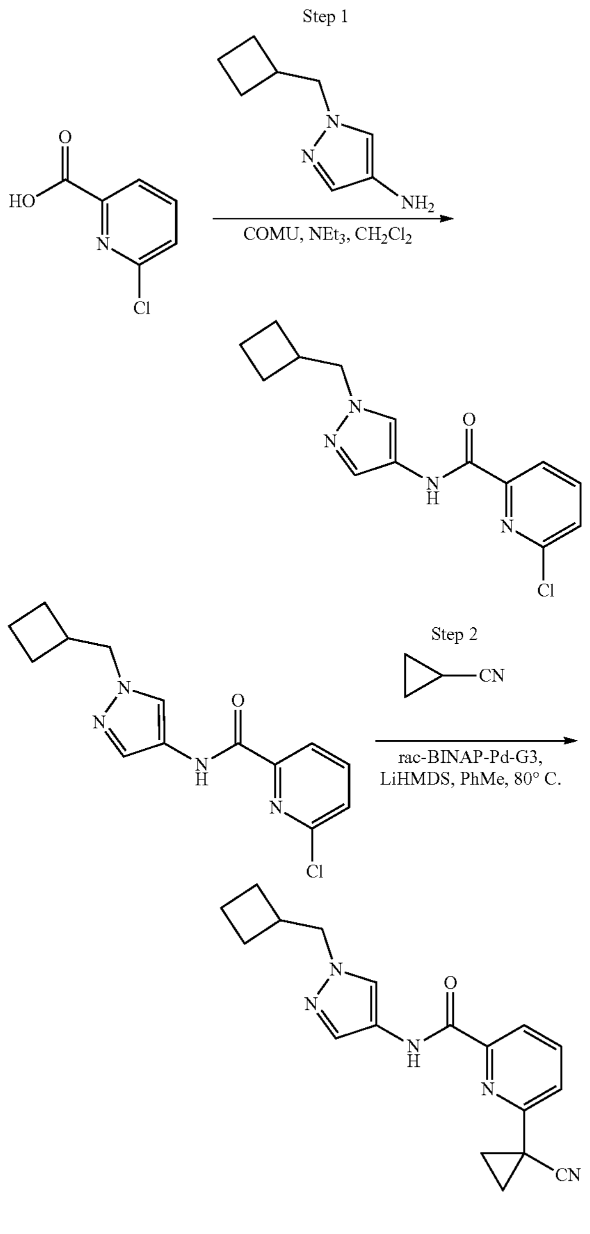

Example 10-1. 6-(1-Cyanocyclopropyl)-N-(1-(cyclobutylmethyl)-1H-pyrazol-4-yl)picolinamide Step 1: To a mixture of 6-chloropicolinic acid (945 mg, 6.0 mmol), COMU (2.57 g, 6.0 mmol), and $CH_2Cl_2$ (30 mL) was added $NEt_3$ (2.5 mL, 18 mmol). The resulting solution was aged for 5 min, at which point 1-(cyclobutylmethyl)-1H-pyrazol-4-amine (907 mg, 6.0 mmol) was added. The resulting solution was stirred at rt overnight. To the crude reaction mixture was added water. The aqueous layer was extracted twice with $CH_2Cl_2$, and the combined organic layers were washed with water, dried over $MgSO_4$, filtered, and concentrated to dryness in vacuo. The crude residue was passed through a short plug of silica gel (eluent: 30% $EtOAc/CH_2Cl_2$) to afford 6-chloro-N-(1-(cyclobutylmethyl)-1H-pyrazol-4-yl)picolinamide. MS (ESI) m/z $C_{14}H_{16}ClN_4O$ $[M+H]^+$ calc'd 291. found 291.

Step 2: To a mixture of 6-chloro-N-(1-(cyclobutylmethyl)-1H-pyrazol-4-yl)picolinamide (62.3 mg, 0.15 mmol), rac-BINAP-Pd-G3 (14.9 mg, 0.015 mmol), and toluene (0.3 mL) was added cyclopropanecarbonitrile (33 μL). The reaction vessel was purged with nitrogen. To the reaction mixture was added LiHMDS (0.45 mL, 1 M in toluene, 0.45 mmol). The resulting solution was heated to 80° C. overnight, and then cooled to rt. To the reaction mixture was added 1:1 $MeOH/CH_2Cl_2$, and the mixture was filtered through a plug of Celite, and the filtrate was concentrated to dryness in vacuo. The crude residue was re-dissolved in 1:1 DMSO/MeOH, filtered, and purified by preparative HPLC (reversed phase, MeCN/water with 0.10% TFA modifier) to afford 6-(1-cyanocyclopropyl)-N-(1-(cyclobutylmethyl)-1H-pyrazol-4-yl)picolinamide, TFA. MS (ESI) m/z $C_{18}H_{20}N_5O$ $[M+H]^+$ calc'd 322. found 322. $^1H$ NMR (500 MHz, DMSO-$d_6$) δ 10.28 (s, 1H), 8.11-8.03 (m, 2H), 8.02-7.95 (m, 1H), 7.89-7.82 (m, 1H), 7.69 (s, 1H), 4.17-4.05 (m, 2H), 2.79-2.68 (m, 1H), 2.12-2.02 (m, 2H), 2.01-1.91 (m, 2H), 1.91-1.66 (m, 6H).

Preparation of Example 11-1

Scheme 22. Synthesis of N-(1-cyclobutyl-1H-pyrazol-4-yl)-2-(1H-pyrazol-1-yl)thiazole-4-carboxamide

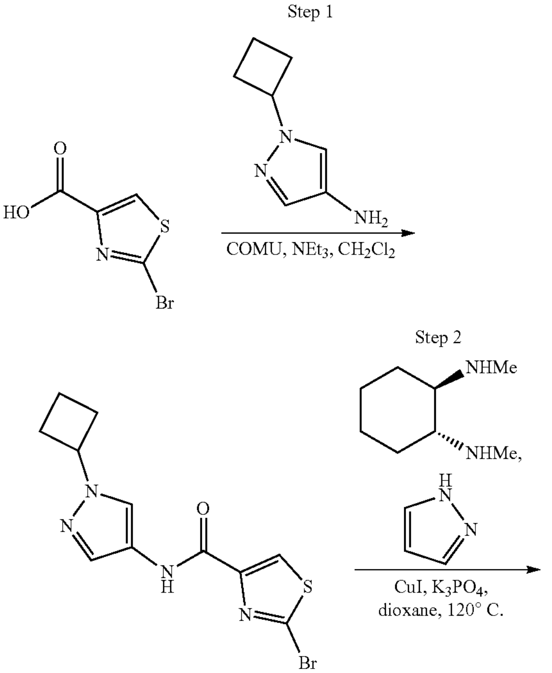

-continued

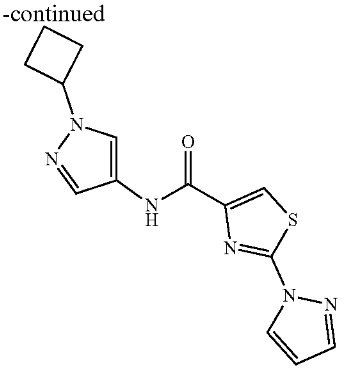

Example 11-1. N-(1-Cyclobutyl-1H-pyrazol-4-yl)-2-(1H-pyrazol-1-yl)thiazole-4-carboxamide Step 1: To a mixture of 2-bromothiazole-4-carboxylic acid (650 mg, 3.12 mmol), 1-cyclobutyl-1H-pyrazol-4-amine (435 mg, 3.17 mmol), HATU (1.19 g, 3.12 mmol), and $CH_2Cl_2$ (15 mL) was added $iPr_2NEt$ (1.64 mL, 9.37 mmol). The resulting mixture was stirred at rt overnight. To the crude reaction mixture was added water. The aqueous layer was extracted twice with $CH_2Cl_2$, and the combined organic layers were washed with water, dried over $MgSO_4$, filtered, and concentrated to dryness in vacuo. The crude residue was passed through a short plug of silica gel (eluent: 20% EtOAc/$CH_2Cl_2$) to afford 2-bromo-N-(1-cyclobutyl-1H-pyrazol-4-yl)thiazole-4-carboxamide. MS (ESI) m/z $C_{11}H_{12}BrN_4OS$ $[M+H]^+$ calc'd 327. found 327.

Step 2: To a mixture of 2-bromo-N-(1-cyclobutyl-1H-pyrazol-4-yl)thiazole-4-carboxamide (38 mg, 0.12 mmol), CuI (11.1 mg, 0.058 mmol), $Cs_2CO_3$ (76 mg, 0.23 mmol), (S,S)-(−)-N,N'-dimethyl-1,2-cyclohexanediamine (16.5 mg, 0.12 mmol) and 1H-pyrazole (15.8 mg, 0.23 mmol) was added dioxane (0.58 mL). The resulting suspension was heated to 80° C. overnight, and then cooled to rt. The reaction mixture was diluted with DMSO, filtered, and purified by preparative HPLC (reversed phase, MeCN/water with 0.1% TFA modifier) to afford N-(1-cyclobutyl-1H-pyrazol-4-yl)-2-(1H-pyrazol-1-yl)thiazole-4-carboxamide, TFA. MS (ESI) m/z $C_{14}H_{15}N_6OS$ $[M+H]^+$ calc'd 315. found 315. $^1H$ NMR (500 MHz, DMSO-$d_6$) δ 10.39 (s, 1H), 8.62 (d, J=2.4 Hz, 1H), 8.14 (s, 1H), 8.11 (s, 1H), 7.92 (s, 1H), 7.70 (s, 1H), 6.72 (s, 1H), 4.83 (p, J=8.4 Hz, 1H), 2.50-2.40 (m, 2H), 2.41-2.32 (m, 2H), 1.84-1.71 (m, 2H).

Compounds in Table 13 below were prepared using procedures analogous to those described in Scheme 22.

TABLE 13

| Number | Structure | Name | Exact Mass $[M + H]^+$ |
|---|---|---|---|
| 11-2 | 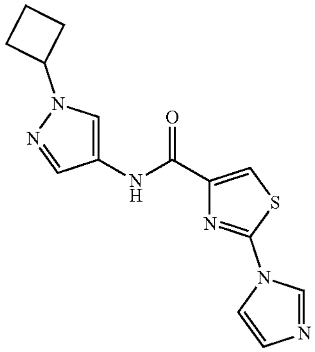 [SMILES: O=C(Nc1cnn(C2CCC2)c1)c1csc(-n2ccnc2)n1] | N-(1-cyclobutyl-1H-pyrazol-4-yl)-2-(1H-imidazol-1-yl)thiazole-4-carboxamide | calc'd 315, found 315 |

Preparation of Example 12-1

Scheme 23. Synthesis of N-(1-(cyclobutylmethyl)-1H-pyrazol-4-yl)-2-(1-methyl-1H-pyrazol-4-yl)thiazole-4-carboxamide

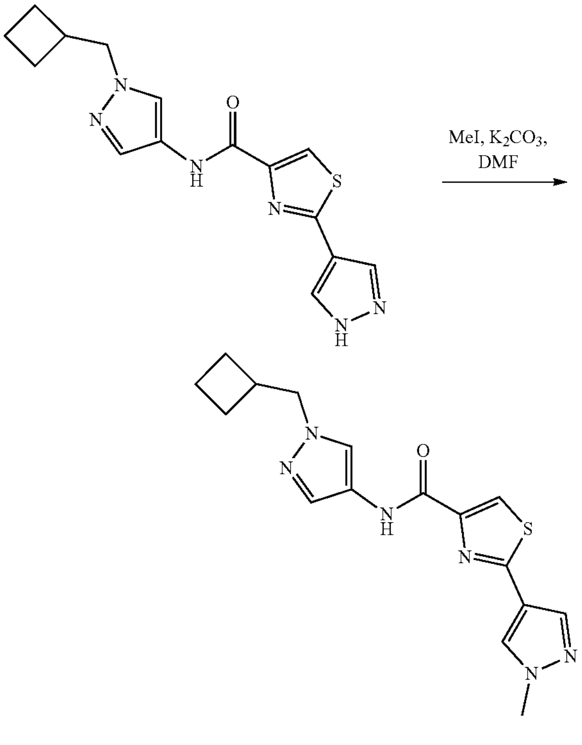

Example 12-1. N-(1-(Cyclobutylmethyl)-1H-pyrazol-4-yl)-2-(1-methyl-1H-pyrazol-4-yl)thiazole-4-carboxamide To a mixture of N-(1-(cyclobutylmethyl)-1H-pyrazol-4-yl)-2-(1H-pyrazol-4-yl)thiazole-4-carboxamide (Example 7-1, 21 mg, 0.052 mmol), $K_2CO_3$ (36.1 mg, 0.26 mmol), and DMF (0.3 mL) was added iodomethane (33 μL, 0.52 mmol). The resulting suspension was stirred at rt overnight. The crude reaction mixture was diluted with DMSO, filtered, and purified by preparative HPLC (reversed phase, MeCN/water with 0.1% TFA modifier) to afford N-(1-(cyclobutylmethyl)-1H-pyrazol-4-yl)-2-(1-methyl-1H-pyrazol-4-yl)thiazole-4-carboxamide. MS (ESI) m/z $C_{16}H_{19}N_6OS$ $[M+H]^+$ calc'd 343. found 343. $^1H$ NMR (500 MHz, DMSO-$d_6$) δ 10.33 (s, 1H), 8.41 (s, 1H), 8.20 (s, 1H), 8.03 (s, 2H), 7.68 (s, 1H), 4.14-4.05 (m, 2H), 3.92 (s, 3H), 2.77-2.66 (m, 1H), 2.02-1.91 (m, 2H), 1.90-1.70 (m, 4H).

Compounds in Table 14 below were prepared from Examples 1-2, 1-3, 1-6, and 3-2 using procedures analogous to those described in Scheme 23.

TABLE 14

| Number | Structure | Name | Exact Mass $[M + H]^+$ |
|---|---|---|---|
| 12-2 | 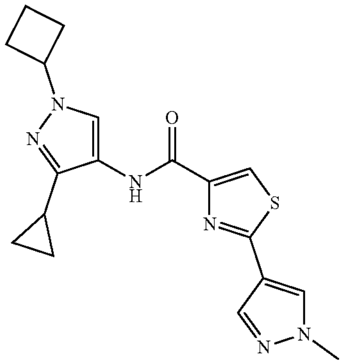 [SMILES: Cn1cc(-c2nc(C(=O)Nc3cn(C4CCC4)nc3C3CC3)cs2)cn1] | N-(1-cyclobutyl-3-cyclopropyl-1H-pyrazol-4-yl)-2-(1-methyl-1H-pyrazol-4-yl)-1,3-thiazole-4-carboxamide | calc'd 369, found 369 |
| 12-3 | 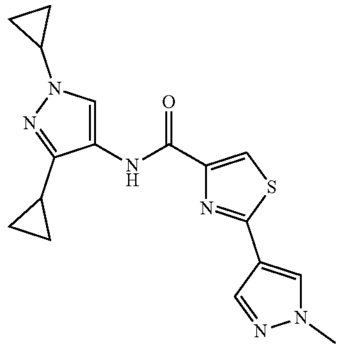 [SMILES: Cn1cc(-c2nc(C(=O)Nc3cn(C4CC4)nc3C3CC3)cs2)cn1] | N-(1,3-dicyclopropyl-1H-pyrazol-4-yl)-2-(1-methyl-1H-pyrazol-4-yl)-1,3-thiazole-4-carboxamide | calc'd 355, found 355 |
| 12-4 | 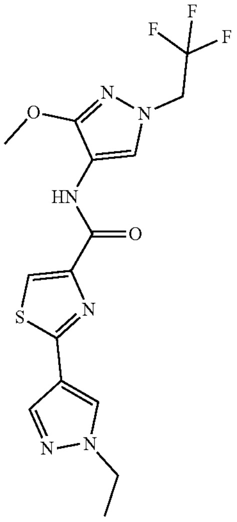 [SMILES: CCn1cc(-c2nc(C(=O)Nc3cn(CC(F)(F)F)nc3OC)cs2)cn1] | 2-(1-ethyl-1H-pyrazol-4-yl)-N-[3-methoxy-1-(2,2,2-trifluoroethyl)-1H-pyrazol-4-yl]-1,3-thiazole-4-carboxamide | calc'd 401, found 401 |

TABLE 14-continued

| Number | Structure | Name | Exact Mass [M + H]+ |
| --- | --- | --- | --- |
| 12-5 | 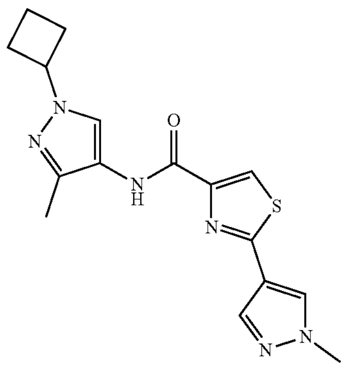 [SMILES: Cc1nn(C2CCC2)cc1NC(=O)c1csc(-c2cnn(C)c2)n1] | N-(1-cyclobutyl-3-methyl-1H-pyrazol-4-yl)-2-(1-methyl-1H-pyrazol-4-yl)-1,3-thiazole-4-carboxamide | calc'd 343 |
| 12-6 | 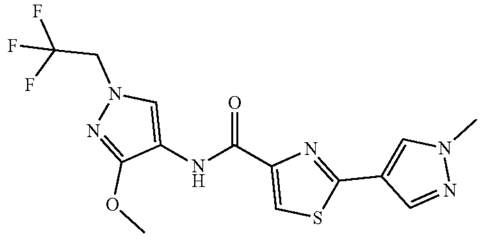 [SMILES: COc1nn(CC(F)(F)F)cc1NC(=O)c1csc(-c2cnn(C)c2)n1] | N-[3-methoxy-1-(2,2,2-trifluoroethyl)-1H-pyrazol-4-yl]-2-(1-methyl-1H-pyrazol-4-yl)-1,3-thiazole-4-carboxamide | calc'd 387, found 387 |

Preparation of Example 13-1

Scheme 24. Synthesis of N-(3-methoxy-1-(2,2,2-trifluoroethyl)-1H-pyrazol-4-yl)-2-(1-(methylsulfonyl)-1H-pyrazol-4-yl)thiazole-4-carboxamide

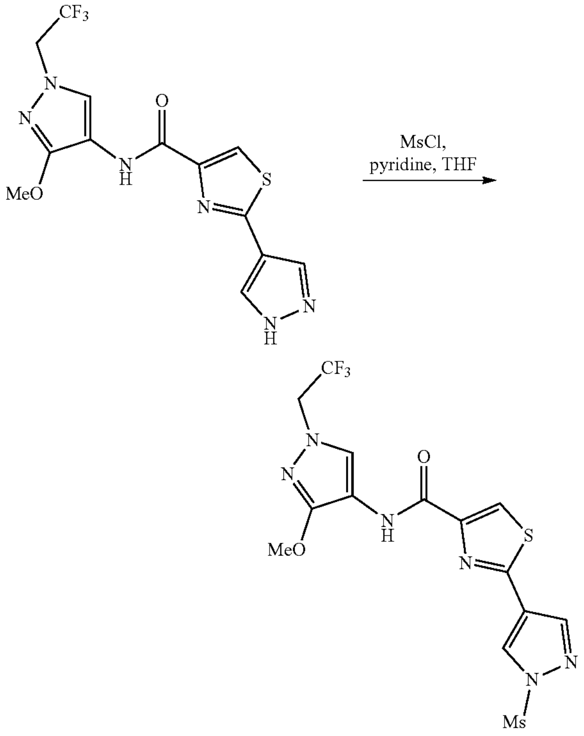

Example 13-1. N-(3-Methoxy-1-(2,2,2-trifluoroethyl)-1H-pyrazol-4-yl)-2-(1-(methylsulfonyl)-1H-pyrazol-4-yl)thiazole-4-carboxamide To a mixture of N-(3-methoxy-1-(2,2,2-trifluoroethyl)-1H-pyrazol-4-yl)-2-(1H-pyrazol-4-yl)thiazole-4-carboxamide, TFA (Example 1-2, 6.0 mg, 0.012 mmol) and THF (0.25 mL) were added sequentially pyridine (20 μL, 0.25 mmol), and then methanesulfonyl chloride (19 μL, 0.25 mmol). The resulting solution was stirred at rt overnight. The crude reaction mixture was diluted with DMSO, filtered, and purified by preparative HPLC (reversed phase, MeCN/water with 0.1% TFA modifier) to afford N-(3-methoxy-1-(2,2,2-trifluoroethyl)-1H-pyrazol-4-yl)-2-(1-(methylsulfonyl)-TH-pyrazol-4-yl)thiazole-4-carboxamide, TFA. MS (ESI) m/z $C_{14}H_{14}F_3N_6O_4S_2$ $[M+H]^+$ calc'd 451. found 451. $^1H$ NMR (500 MHz, DMSO-$d_6$) δ 9.42 (s, 1H), 9.05 (s, 1H), 8.57 (s, 1H), 8.40 (s, 1H), 8.06 (s, 1H), 4.98 (s, 2H), 3.89 (s, 3H), 3.68 (s, 3H).

The compounds of the invention, surprisingly and advantageously, exhibit good potency as inhibitors of LRRK2 kinase. The pIC50 values reported herein were measured as follows.

Biological Assay: LRRK2 $K_m$ ATP LanthaScreen™ Assay

Compound potency against LRRK2 kinase activity was determined using LanthaScreen™ technology from Life Technologies Corporation (Carlsbad, CA) using a GST20 tagged truncated human mutant G2019S LRRK2 in the presence of the fluorescein-labeled peptide substrate LRRKtide® (LRRK2 phosphorylated ezrin/radixin/moesin (ERM)), also from Life Technologies. The data presented for the $K_m$ ATP LanthaScreen™ Assay represents mean $IC_{50}$ values based on several test results and may have reasonable deviations depending on the specific conditions and reagents used. $K_m$ is the Michaelis constant of an enzyme and is defined as the concentration of native substrate (ATP for a kinase) which permits the enzyme to achieve half $V_{max}$ ($V_{max}$=rate of reaction when the enzyme is saturated with substrate). $IC_{50}$ (half-maximal inhibitory concentration) represents the concentration of inhibitor required to inhibit LRRK2 kinase activity by 50%. Assays were performed in the presence of 134 μM ATP ($K_m$ ATP). Upon completion, the assay was stopped, and phosphorylated substrate detected with a terbium (Tb)-labeled anti-pERM antibody (cat. no. PV4898). The compound dose response was prepared by diluting a 10 mM stock of compound to a maximum concentration of 9.99 μM in 100% DMSO, followed by custom fold serial dilution in DMSO nine times. 20 nL of each dilution was spotted via a Labcyte Echo onto a 384-well black-sided plate (Corning 3575) followed by 15 μL of a 1.25 nM enzyme solution in 1× assay buffer (50 mM Tris pH 8.5, 10 mM $MgCl_2$, 0.01% Brij-35, 1 mM EGTA, 2 mM dithiothreitol, 0.05 mM sodium orthovanadate). Following a 15-min incubation period at rt, the kinase reaction was started with the addition of 5 μL of 400 nM fluorescein-labeled LRRKtide® (LRRK2 phosphorylated ezrin/radixin/moesin (ERM)) peptide substrate and 134 μM ATP solution in 1× assay buffer. The reaction was allowed to progress at ambient temperature for 90 min. The reaction was then stopped by the addition of 20 μL of TR-FRET Dilution Buffer (Life Technologies, Carlsbad, CA) containing 2 nM Tb-labeled anti-phospho LRRKtide® (LRRK2 phosphorylated ezrin/radixin/moesin (ERM)) antibody and 10 mM EDTA (Life Technologies, Carlsbad, CA). After an incubation period of 1 h at rt, the plate was read on an EnVision® multimode plate reader (Perkin Elmer, Waltham, MA) with an excitation wavelength of 337 nm (Laser) and a reading emission at both 520 and 495 nm. Compound $IC_{50}$ values were interpolated from nonlinear regression best-fits of the log of the final compound concentration, plotted as a function of the 520/495-nm emission ratio using activity base "Abase"). Abase uses a 4 parameter (4P) logistic fit based on the Levenberg-Marquardt algorithm. The $PIC_{50}$ values set forth in Table 15 below were derived from the $IC_{50}$ values (in molar concentration) and represent the negative logarithm of these values. The "Example" column in Table 15 corresponds to the example number of the compounds in the examples and tables above.

TABLE 15

| Example | LRRK2 $pIC_{50}$ |
|---|---|
| Example 1-1 | 8.01 |
| Example 1-2 | 7.46 |
| Example 1-3 | 7.83 |
| Example 1-4 | 8.15 |
| Example 1-5 | 7.08 |
| Example 1-6 | 7.84 |
| Example 1-7 | 7.17 |
| Example 1-8 | 8.07 |
| Example 1-9 | 7.09 |
| Example 1-10 | 7.30 |
| Example 1-11 | 7.90 |
| Example 1-12 | 7.53 |
| Example 1-13 | 8.17 |
| Example 1-14 | 7.13 |
| Example 1-15 | 7.79 |
| Example 1-16 | 7.43 |
| Example 1-17 | 7.22 |
| Example 1-18 | 6.75 |
| Example 1-19 | 8.66 |
| Example 1-20 | 7.68 |
| Example 1-21 | 7.18 |
| Example 1-22 | 7.76 |
| Example 1-23 | 6.59 |
| Example 1-24 | 7.56 |
| Example 1-25 | 7.65 |

TABLE 15-continued

| Example | LRRK2 $pIC_{50}$ |
|---|---|
| Example 1-26 | 7.56 |
| Example 1-27 | 7.77 |
| Example 1-28 | 6.95 |
| Example 1-29 | 7.82 |
| Example 1-30 | 7.78 |
| Example 1-31 | 7.95 |
| Example 1-32 | 8.00 |
| Example 1-33 | 7.13 |
| Example 1-34 | 7.92 |
| Example 1-35 | 7.77 |
| Example 1-36 | 7.25 |
| Example 1-37 | 7.51 |
| Example 1-38 | 8.23 |
| Example 1-39 | 6.36 |
| Example 1-40 | 7.10 |
| Example 1-41 | 7.23 |
| Example 1-42 | 7.74 |
| Example 1-43 | 7.64 |
| Example 1-44 | 7.91 |
| Example 1-45 | 6.77 |
| Example 1-46 | 7.57 |
| Example 2-1 | 7.49 |
| Example 2-2 | 7.42 |
| Example 2-3 | 6.99 |
| Example 2-4 | 6.82 |
| Example 3-1 | 7.27 |
| Example 3-2 | 8.35 |
| Example 3-3 | 7.16 |
| Example 3-4 | 5.69 |
| Example 3-5 | 5.92 |
| Example 4-1 | 7.98 |
| Example 4-2 | 5.07 |
| Example 4-3 | 6.19 |
| Example 4-4 | 5.68 |
| Example 4-5 | 5.82 |
| Example 4-6 | 7.10 |
| Example 4-7 | 5.56 |
| Example 4-8 | 6.33 |
| Example 4-9 | 6.70 |
| Example 4-10 | 5.35 |
| Example 4-11 | 5.71 |
| Example 4-12 | 6.18 |
| Example 4-13 | 6.76 |
| Example 4-14 | 6.12 |
| Example 4-15 | 7.28 |
| Example 4-16 | 6.04 |
| Example 4-17 | 5.91 |
| Example 4-18 | 5.81 |
| Example 5-1 | 7.50 |
| Example 6-1 | 7.47 |
| Example 7-1 | 7.76 |
| Example 7-2 | 7.58 |
| Example 7-3 | 7.27 |
| Example 7-4 | 6.79 |
| Example 7-5 | 7.32 |
| Example 7-6 | 6.43 |
| Example 7-7 | 7.72 |
| Example 7-8 | 7.35 |
| Example 7-9 | 7.75 |
| Example 7-10 | 7.37 |
| Example 7-11 | 7.55 |
| Example 7-12 | 7.68 |
| Example 7-13 | 6.84 |
| Example 7-14 | 7.92 |
| Example 7-15 | 6.36 |
| Example 7-16 | 7.25 |
| Example 7-17 | 7.76 |
| Example 7-18 | 7.72 |
| Example 7-19 | 7.80 |
| Example 7-20 | 7.58 |
| Example 7-21 | 6.57 |
| Example 7-22 | 7.00 |
| Example 7-23 | 7.59 |
| Example 7-24 | 7.30 |
| Example 7-25 | 7.70 |
| Example 7-26 | 6.84 |
| Example 7-27 | 7.50 |
| Example 7-28 | 6.71 |

TABLE 15-continued

| Example | LRRK2 $pIC_{50}$ |
|---|---|
| Example 7-29 | 7.78 |
| Example 7-30 | 6.25 |
| Example 7-31 | 7.40 |
| Example 7-32 | 7.38 |
| Example 7-33 | 8.13 |
| Example 7-34 | 5.95 |
| Example 7-35 | 6.24 |
| Example 7-36 | 7.65 |
| Example 7-37 | 7.72 |
| Example 7-38 | 8.02 |
| Example 7-39 | 7.74 |
| Example 7-40 | 6.97 |
| Example 7-41 | 7.46 |
| Example 7-42 | 6.51 |
| Example 7-43 | 6.87 |
| Example 8-1 | 7.90 |
| Example 8-2 | 7.74 |
| Example 8-3 | 7.89 |
| Example 8-4 | 7.82 |
| Example 9-1 | 7.27 |
| Example 9-2 | 5.74 |
| Example 9-3 | 8.01 |
| Example 9-4 | 7.41 |
| Example 9-5 | 5.79 |
| Example 9-6 | 6.18 |
| Example 9-7 | 6.87 |
| Example 9-8 | 6.54 |
| Example 9-9 | 8.04 |
| Example 9-10 | 7.76 |
| Example 9-11 | 5.63 |
| Example 9-12 | 6.95 |
| Example 9-13 | 7.68 |
| Example 9-14 | 7.41 |
| Example 9-15 | 6.66 |
| Example 9-16 | 5.04 |
| Example 9-17 | 7.50 |
| Example 9-18 | 7.59 |
| Example 9-19 | 5.22 |
| Example 9-20 | 5.07 |
| Example 9-21 | 8.08 |
| Example 9-22 | 6.53 |
| Example 9-23 | 7.47 |
| Example 9-24 | 7.16 |
| Example 9-25 | 7.38 |
| Example 9-26 | 6.09 |
| Example 9-27 | 8.25 |
| Example 9-28 | 7.85 |
| Example 9-29 | 5.51 |
| Example 9-30 | 6.76 |
| Example 9-31 | 5.18 |
| Example 9-32 | 6.59 |
| Example 9-33 | 6.75 |
| Example 9-34 | 6.90 |
| Example 9-35 | 5.32 |
| Example 9-36 | 6.90 |
| Example 9-37 | 5.95 |
| Example 9-38 | 7.10 |
| Example 9-39 | 7.06 |
| Example 9-40 | 7.06 |
| Example 10-1 | 6.90 |
| Example 11-1 | 7.00 |
| Example 11-2 | 6.61 |
| Example 12-1 | 7.74 |
| Example 12-2 | 7.76 |
| Example 12-3 | 7.84 |
| Example 12-4 | 6.57 |
| Example 12-5 | 7.30 |
| Example 12-6 | 7.06 |
| Example 13-1 | 5.97 |

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in the responsiveness of the mammal being treated for any of the indications with the compounds of the invention indicated above. Likewise, the specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed:

1. A compound having a structural Formula (I):

I

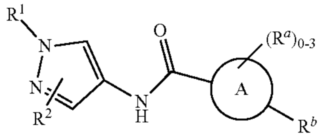

or a pharmaceutically acceptable salt thereof, wherein:

A is a heteroaryl or aryl selected from the group consisting of thiazolyl, pyrazolyl, pyridyl, phenyl, pyrimidinyl, oxazolyl and pyrazinyl;

$R^1$ is selected from hydrogen, $C_{1-6}$ alkyl, $-(CH_2)_nOC_{1-6}$ alkyl, $-(CH_2)$ halogen, $-(CH_2)_nCN$, $C_{1-6}$ haloalkyl, $-CH(R)_2$, $-(CH_2)_nC_{3-6}$cycloalkyl, $-(CH_2)_nC_{6-10}$aryl, $-(CH_2)_nC_{5-10}$heteroaryl, $-(CH_2)_nC_{4-10}$heterocyclyl, and $-(CH_2)_nN(R)_2$, said alkyl and cycloalkyl, aryl, heteroaryl, and heterocyclyl optionally substituted with 1 to 3 groups selected from $R^x$;

R is selected from hydrogen, $C_{1-6}$ alkyl, cyclopropyl, CN, $NHCH(CH_3)_2$, and phenyl, said phenyl optionally substituted with 1 to 3 groups of $R^x$;

$R^2$ is selected from hydrogen, $C_{1-6}$ alkyl, $-OC_{1-6}$ alkyl, halogen, C(O) $C_{1-6}$alkyl, $C(O)N(R)_2$, $-C(O)\ OC_{1-6}$alkyl, CN, $C_{1-6}$haloalkyl, $-C_{3-6}$cycloalkyl, $(O)_{0-1}C_{6-10}$aryl, $C_{5-10}$heteroaryl, and $-(CH_2)_nN(R)_2$, said alkyl and cycloalkyl, aryl, and heteroaryl optionally substituted with 1 to 3 groups selected from $R^x$;

$R^a$ is selected from $C_{1-6}$ alkyl, CN and halogen;

$R^b$ are independently selected from $C_{1-6}$ alkyl, $-OC_{1-6}$ alkyl, $C_{3-6}$ cycloalkyl, $-SC_{1-6}$alkyl, $C_{6-10}$aryl, $C_{5-10}$heteroaryl, $C_{3-10}$heterocyclyl, $NHC(O)C_{1-6}$alkyl, $N(R)_2$, and $-NHC_{6-10}$aryl, said alkyl, aryl, heteroaryl, and heterocyclyl optionally substituted with 1 to 3 groups of $R^y$;

$R^x$ is selected from $C_{1-6}$ alkyl, $-OC_{1-6}$ alkyl, OH, $C_{3-6}$ cycloalkyl $-CH_2SC_{1-6}$ alkyl, $-OCH_2OC_{1-6}$ alkyl, halogen, $-SO_2CH_3$, CN, and $(CH_2)_nN(R)_2$, $R^y$ is selected from hydrogen, $C_{1-6}$ alkyl, $-(CH_2)_nOC_{1-6}$ alkyl, $C_{3-6}$cycloalkyl, $C_{1-6}$ haloalkyl, -halogen, CN, $(CH_2)_nC_{4-10}$heterocyclyl, $-(CH_2)_{n\ 5-10}$heteroaryl, and $-SO_2C_{1-6}$ alkyl; and n is selected from 0 to 3 with the provisio that when A is phenyl, thiazolyl and oxazolyl then $R^2$ is not benzimidazolyl or pyridyl; when A is pyrimidinyl or pyrazinyl it is not substituted with $NH_2$; and when A is pyridyl then $R^1$ is not $CH_2CF_3$.

2. The compound according to claim 1 or a pharmaceutically acceptable salt thereof wherein A is thiazolyl.

3. The compound according to claim 1 or a pharmaceutically acceptable salt thereof wherein A is pyridyl.

4. The compound according to claim 1 or a pharmaceutically acceptable salt thereof wherein A is phenyl.

5. The compound according to claim 1 or a pharmaceutically acceptable salt thereof wherein A is oxazolyl.

6. The compound according to claim 1 or a pharmaceutically acceptable salt thereof wherein $R^1$ is selected from the group consisting of —$(CH_2)_n$cyclobutyl, —$(CH_2)_n$cyclopropyl, CH(cyclopropyl)$_2$, —$(CH_2)_n$cyclopentyl, —$(CH_2)_n$cyclohexyl, $CH_3$, $CH(CH_3)_2$, $CH_2$ $CH(CH_3)_2$, $CH_2CH_3$, $C(CH_3)_3$, $(CH_2)_nCN$, $CH(CH_3)$ CN, $CH_2CF_3$, $CHF_2$, $CH_2OH$, $CH_2CHF_2$, $(CH_2)_nOCH_3$, $(CH_2)_nF$, $(CH_2)_n$phenyl, $(CH_2)_n$napthyl, $(CH_2)_n$pyridyl, $(CH_2)_n$pyrrolyl, tetrahydrotriazoloazepinyl, $(CH_2)_n$oxetanyl, $(CH_2)_n$piperidinyl, $(CH_2)_n$tetrahydropyranyl, $(CH_2)_n$tetrahydrofuranyl, $(CH_2)_n$piperazinyl, $(CH_2)_n$pyrrolidinyl, $(CH_2)_n$imidazolyl, $(CH_2)_n$triazoloazepinyl, $(CH_2)_n$tetrahydrotriazolyl, $(CH_2)$ morpholinyl, and $(CH_2)_n$azabicyclooctanyl said cyclobutyl cyclopropyl, cyclopentyl, cyclohexyl, phenyl, napthyl, pyridyl, pyrrolyl, tetrahydrotriazoloazepinyl, oxetanyl, piperidinyl, tetrahydropyranyl, tetrahydrofuranyl, piperazinyl, pyrrolyl, imidazolyl, triazoloazepinyl, tetrahydrotriazolyl, morpholinyl and azabicyclooctanyl unsubstituted or substituted with 1 to 3 groups of $R^x$.

7. The compound according to claim 1 or a pharmaceutically acceptable salt thereof wherein $R^1$ is selected from the group consisting of —$(CH_2)_n$cyclobutyl, —$(CH_2)_n$cyclopropyl, $CH_3$, $CH(CH_3)_2$, $CH_2CH_3$, $C(CH_3)_3$, $CH_2CF_3$, $CHF_2$, $CH_2CHF_2$, $(CH_2)_nOCH_3$, and $(CH_2)_nF$.

8. The compound according to claim 1 or a pharmaceutically acceptable salt thereof wherein $R^2$ is selected from the group consisting of hydrogen, $CH_3$, $OCH_2CF_3$, $OCH_3$, $CHF_2$, $OCH(CH_3)_2$, $OCH_2CHF_2$, $C(O)OCH_3$, $CF_3$, CN, cyclopropyl, cyclobutyl, cyclopentyl, cyclohexyl, phenyl, —Ophenyl, said phenyl, —Ophenyl, pyridyl, tetrahydrotriazopyridyl, or pyrazolyl unsubstituted or substituted with 1 to 3 groups from $R^x$.

9. The compound according to 1 or a pharmaceutically acceptable salt there of wherein $R^2$ is selected from the group consisting of hydrogen, $CH_3$, and $CHF_2$.

10. The compound according to claim 1 or a pharmaceutically acceptable salt thereof where $R^b$ is selected from the group consisting of $C_{1-6}$alkyl, cyclopropyl and cyclobutyl, —$SC_{1-6}$alkyl, phenyl, —NHphenyl, pyridyl, pyrimidinyl, pyrazolyl, furanyl, imidazolyl, thiazolyl, isothiazolyl, pyrrolyl, oxazinylthiazolyl, pyridazinyl, and benzothiophenyl, said alkyl, cyclopropyl, cyclobutyl, phenyl, pyridyl, pyrimidinyl, pyrazolyl, furanyl, imidazolyl, thiazolyl, isothiazolyl, pyrrolyl, and benzothiophenyl unsubstituted or substituted with 1 to 3 groups of $R^y$.

11. The compound according to claim 1 or a pharmaceutically acceptable salt thereof wherein $R^b$ is pyrazolyl unsubstituted or substituted with 1 to 3 groups of $R^y$.

12. The compound according to claim 1 or a pharmaceutically acceptable salt thereof wherein $R^b$ is pyridyl unsubstituted or substituted with 1 to 3 groups of $R^y$.

13. The compound according to claim 1 or a pharmaceutically acceptable salt thereof represented by Formula II:

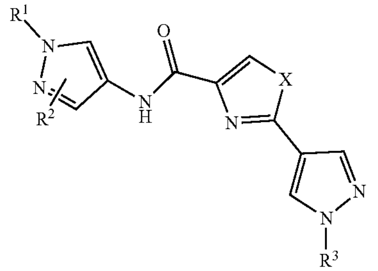

II or a pharmaceutically acceptable salt thereof, wherein X is S or O, and $R^3$ is selected from the group consisting of hydrogen, $C_{1-6}$ alkyl, $(CH_2)_nOC_{1-6}$ alkyl, $C_{1-6}$ haloalkyl, $(CH_2)_nC_{5-10}$heteroaryl, halogen, CN, and $SO_2C_{1-6}$ alkyl, said alkyl and aryl unsubstituted or substituted with 1 to 3 groups from $R^x$.

14. The compound according to claim 13 or a pharmaceutically acceptable salt thereof wherein X is S, $R^1$ is selected from $CH_3$, $CH_2CH_3$, $CH(CH_3)_2$, —$(CH_2)_n$cyclopropyl, —$(CH_2)_n$cyclobutyl, and CH(cyclopropyl)$_2$, and $R^2$ is selected from hydrogen, $CH_3$, $OCH_2CF_3$, $OCH_3$, $CHF_2$, $OCH(CH_3)_2$, $OCH_2CHF_2$, $CF_3$, C(O) $OCH_3$, cyclopropyl, cyclobutyl, cyclopentyl, cyclohexyl, phenyl, —O-phenyl, pyridyl, tetrahydrotriazopyridyl, pyrazolyl, and CN, said cyclopropyl, cyclobutyl, cyclopentyl, cyclohexyl, phenyl, —O-phenyl, pyridyl, tetrahydrotriazopyridyl, pyrazolyl unsubstituted or substituted with 1 to 3 groups of $R^x$.

15. The compound of claim 1, or a pharmaceutically acceptable salt thereof, wherein said compound is selected from:

N-(1-Cyclobutyl-1H-pyrazol-4-yl)-2-(1H-pyrazol-4-yl)thiazole-4-carboxamide,
N-(3-Methoxy-1-(2,2,2-trifluoroethyl)-1H-pyrazol-4-yl)-2-(1H-pyrazol-4-yl)thiazole-4-carboxamide,
N-(1-Cyclobutyl-3-methyl-1H-pyrazol-4-yl)-2-(1H-pyrazol-4-yl)thiazole-4-carboxamide,
N-[1-methyl-3-(methylcarbamoyl)-1H-pyrazol-4-yl]-2-(1H-pyrazol-4-yl)-1,3-thiazole-4-carboxamide
N-[1-(difluoromethyl)-3-methyl-1H-pyrazol-4-yl]-2-(1H-pyrazol-4-yl)-1,3-thiazole-4-carboxamide
N-(1,3-dicyclopropyl-1H-pyrazol-4-yl)-2-(1H-pyrazol-4-yl)-1,3-thiazole-4-carboxamide
N-[1-(1-methylethyl)-3-(2,2,2-trifluoroethoxy)-1H-pyrazol-4-yl]-2-(1H-pyrazol-4-yl)-1,3-thiazole-4-carboxamide
2-(1H-pyrazol-4-yl)-N-(1-pyridin-4-yl-1H-pyrazol-4-yl)-1,3-thiazole-4-carboxamide
N-(1-methyl-3-pyridin-4-yl-1H-pyrazol-4-yl)-2-(1H-pyrazol-4-yl)-1,3-thiazole-4-carboxamide
N-(3-cyano-1-ethyl-1H-pyrazol-4-yl)-2-(1H-pyrazol-4-yl)-1,3-thiazole-4-carboxamide
N-[3-(4-fluorophenyl)-1-methyl-1H-pyrazol-4-yl]-2-(1H-pyrazol-4-yl)-1,3-thiazole-4-carboxamide
N-[1-ethyl-3-(5,6,7,8-tetrahydro[1,2,4]triazolo[4,3-a]pyridin-3-yl)-1H-pyrazol-4-yl]-2-(1H-pyrazol-4-yl)-1,3-thiazole-4-carboxamide
N-(3-carbamoyl-1-methyl-1H-pyrazol-4-yl)-2-(1H-pyrazol-4-yl)-1,3-thiazole-4-carboxamide -continued N-(3-methoxy-1-methyl-1H-pyrazol-4-yl)-2-(1H-pyrazol-4-yl)-1,3-thiazole-4-carboxamide
N-[3-(difluoromethyl)-1-methyl-1H-pyrazol-4-yl]-2-(1H-pyrazol-4-yl)-1,3-thiazole-4-carboxamide
N-[1-methyl-3-(1-methylethoxy)-1H-pyrazol-4-yl]-2-(1H-pyrazol-4-yl)-1,3-thiazole-4-carboxamide
N-(1-tert-butyl-1H-pyrazol-4-yl)-2-(1H-pyrazol-4-yl)-1,3-thiazole-4-carboxamide
N-(1-cyclopropyl-1H-pyrazol-4-yl)-2-(1H-pyrazol-4-yl)-1,3-oxazole-4-carboxamide
methyl 1-methyl-4-({[2-(1H-pyrazol-4-yl)-1,3-thiazol-4-yl]carbonyl}amino)-1H-pyrazole-3-carboxylate
N-[1-(1-methylethyl)-1H-pyrazol-4-yl]-2-(1H-pyrazol-4-yl)-1,3-thiazole-4-carboxamide
2-(1H-pyrazol-4-yl)-N-(1-pyridin-4-yl-1H-pyrazol-4-yl)-1,3-oxazole-4-carboxamide
N-(1-cyclobutyl-3-methoxy-1H-pyrazol-4-yl)-2-(1H-pyrazol-4-yl)-1,3-thiazole-4-carboxamide
N-[1-(dicyclopropylmethyl)-3-methyl-1H-pyrazol-4-yl]-2-(1H-pyrazol-4-yl)-1,3-thiazole-4-carboxamide
N-(1-phenyl-1H-pyrazol-4-yl)-2-(1H-pyrazol-4-yl)-1,3-thiazole-4-carboxamide
N-(1-cyclopropyl-1H-pyrazol-4-yl)-2-(1H-pyrazol-4-yl)-1,3-thiazole-4-carboxamide
N-[3-(2,2-difluoroethoxy)-1-methyl-1H-pyrazol-4-yl]-2-(1H-pyrazol-4-yl)-1,3-thiazole-4-carboxamide
N-[1-({1-[(methylsulfanyl)methyl]cyclobutyl}methyl)-1H-pyrazol-4-yl]-2-(1H-pyrazol-4-yl)-1,3-thiazole-4-carboxamide
N-[3-methoxy-1-(6,7,8,9-tetrahydro-5H-[1,2,4]triazolo[4,3-a]azepin-3-ylmethyl)-1H-pyrazol-4-yl]-2-(1H-pyrazol-4-yl)-1,3-thiazole-4-carboxamide
N-(1-{[1-(methoxymethyl)cyclobutyl]methyl}-1H-pyrazol-4-yl)-2-(1H-pyrazol-4-yl)-1,3-thiazole-4-carboxamide
N-(1-methyl-3-phenoxy-1H-pyrazol-4-yl)-2-(1H-pyrazol-4-yl)-1,3-thiazole-4-carboxamide
N-(1,1'-dimethyl-1H,1'H-3,4'-bipyrazol-4-yl)-2-(1H-pyrazol-4-yl)-1,3-thiazole-4-carboxamide
N-{1-[(3,3-dimethylcyclobutyl)methyl]-1H-pyrazol-4-yl}-2-(1H-pyrazol-4-yl)-1,3-thiazole-4-carboxamide
N-(1-cyclobutyl-1H-pyrazol-4-yl)-2-(1H-pyrazol-4-yl)-1,3-oxazole-4-carboxamide
N-{1-[(1-methylcyclobutyl)methyl]-1H-pyrazol-4-yl}-2-(1H-pyrazol-4-yl)-1,3-thiazole-4-carboxamide
N-{1-[(3,3-difluorocyclobutyl)methyl]-1H-pyrazol-4-yl}-2-(1H-pyrazol-4-yl)-1,3-thiazole-4-carboxamide
N-[3-(dimethylcarbamoyl)-1-methyl-1H-pyrazol-4-yl]-2-(1H-pyrazol-4-yl)-1,3-thiazole-4-carboxamide
N-(1-cyclopropyl-3-methoxy-1H-pyrazol-4-yl)-2-(1H-pyrazol-4-yl)-1,3-thiazole-4-carboxamide
N-[1-cyclopropyl-3-(difluoromethyl)-1H-pyrazol-4-yl]-2-(1H-pyrazol-4-yl)-1,3-thiazole-4-carboxamide
N-[1-(1-methylethyl)-1H-pyrazol-4-yl]-2-(1H-pyrazol-4-yl)-1,3-oxazole-4-carboxamide
N-[1-methyl-3-(trifluoromethyl)-1H-pyrazol-4-yl]-2-(1H-pyrazol-4-yl)-1,3-thiazole-4-carboxamide
N-(1,3-dimethyl-1H-pyrazol-4-yl)-2-(1H-pyrazol-4-yl)-1,3-thiazole-4-carboxamide
N-(3-cyclopropyl-1-methyl-1H-pyrazol-4-yl)-2-(1H-pyrazol-4-yl)-1,3-thiazole-4-carboxamide
N-{1-[(1-fluorocyclobutyl)methyl]-1H-pyrazol-4-yl}-2-(1H-pyrazol-4-yl)-1,3-thiazole-4-carboxamide
N-[1-({1-[(methylsulfonyl)methyl]cyclobutyl } methyl)-1H-pyrazol-4-yl]-2-(1H-pyrazol-4-yl)-1,3-thiazole-4-carboxamide
N-[1-(4-fluorobenzyl)-1H-pyrazol-4-yl]-2-(1H-pyrazol-4-yl)-1,3-oxazole-4-carboxamide
N-[3-(2,2-difluoroethoxy)-1-(1-methylethyl)-1H-pyrazol-4-yl]-2-(1H-pyrazol-4-yl)-1,3-thiazole-4-carboxamide
(R)— or (S)—N-(1-(1-Cyclopropylethyl)-1H-pyrazol-4-yl)-2-(1H-pyrazol-4-yl)thiazole-4-carboxamide
(R)— or (S)—N-{1-[1-cyclopropylethyl]-3-methyl-1H-pyrazol-4-yl}-2-(1H-pyrazol-4-yl)-1,3-thiazole-4-carboxamide
(S)— or (R)—N-{1-[1-cyclopropylethyl]-3-methyl-1H-pyrazol-4-yl}-2-(1H-pyrazol-4-yl)-1,3-thiazole-4-carboxamide
N-(1-(1-Cyclopropylethyl)-3-(difluoromethyl)-1H-pyrazol-4-yl)-2-(1H-pyrazol-4-yl)thiazole-4-carboxamide
N-(1-cyclobutyl-3-cyclopropyl-1H-pyrazol-4-yl)-2-(1H-pyrazol-4-yl)-1,3-thiazole-4-carboxamide
N-(1-cyclobutyl-5-cyclopropyl-1H-pyrazol-4-yl)-2-(1H-pyrazol-4-yl)-1,3-thiazole-4-carboxamide
(R)— or (S)—N-(1-(1-Cyclopropylethyl)-5-(difluoromethyl)-1H-pyrazol-4-yl)-2-(1H-pyrazol-4-yl)thiazole-4-carboxamide
N-(1-Cyclopropyl-1H-pyrazol-4-yl)-6-(1-(2,2,2-trifluoroethyl)-1H-pyrazol-4-yl)picolinamide
5-cyano-N-(1-cyclobutyl-1H-pyrazol-4-yl)-6-methylpyridine-2-carboxamide
N-(1-cyclobutyl-1H-pyrazol-4-yl)-2-[(1-methylethyl)amino]-1,3-thiazole-4-carboxamide
N-(1-cyclobutyl-1H-pyrazol-4-yl)-2-phenyl-1,3-oxazole-4-carboxamide
N-(1-cyclobutyl-1H-pyrazol-4-yl)-2-(methylsulfanyl)-1,3-thiazole-4-carboxamide
N-(1-cyclobutyl-1H-pyrazol-4-yl)-6-(1-methylethoxy)pyridine-2-carboxamide
N-(1-cyclobutyl-1H-pyrazol-4-yl)-1-phenyl-1H-pyrazole-3-carboxamide
6-(acetylamino)-N-(1-cyclobutyl-1H-pyrazol-4-yl)pyridine-2-carboxamide -continued N-(1-cyclobutyl-1H-pyrazol-4-yl)-2-phenyl-1,3-thiazole-4-carboxamide
N-(1-cyclobutyl-1H-pyrazol-4-yl)-6-methoxypyridine-2-carboxamide
N-(1-cyclobutyl-1H-pyrazol-4-yl)-1-pyrimidin-2-yl-1H-pyrazole-3-carboxamide
2-(acetylamino)-N-(1-cyclobutyl-1H-pyrazol-4-yl)-1,3-thiazole-4-carboxamide
N-(1-cyclobutyl-1H-pyrazol-4-yl)-6-(1H-pyrazol-1-yl)pyridine-2-carboxamide
N-(1-cyclobutyl-1H-pyrazol-4-yl)-2-(phenylamino)-1,3-thiazole-4-carboxamide
N-(1-methyl-1H-pyrazol-4-yl)-2-(1H-pyrazol-4-yl)thiazole-4-carboxamide
N-(1-cyclobutyl-1H-pyrazol-4-yl)-6-(pyrrolidin-1-yl)picolinamide
N-(1-cyclobutyl-1H-pyrazol-4-yl)-6-(1H-imidazol-1-yl)picolinamide
N-(1-cyclobutyl-1H-pyrazol-4-yl)-6-(piperidin-1-yl)picolinamide
N-(1-((3-Fluorooxetan-3-yl)methyl)-1H-pyrazol-4-yl)-2-(1H-pyrazol-4-yl)thiazole-4-carboxamide
N-(3-(Hydroxymethyl)-1-methyl-1H-pyrazol-4-yl)-2-(1H-pyrazol-4-yl)thiazole-4-carboxamide
N-(1-(Cyclobutylmethyl)-1H-pyrazol-4-yl)-2-(1H-pyrazol-4-yl)thiazole-4-carboxamide
N-[1-(2,2-difluoroethyl)-3-(difluoromethyl)-1H-pyrazol-4-yl]-2-(1H-pyrazol-4-yl)-1,3-thiazole-4-carboxamide
N-[3-(difluoromethyl)-1-(2-methoxyethyl)-1H-pyrazol-4-yl]-2-(1H-pyrazol-4-yl)-1,3-thiazole-4-carboxamide
N-{1-[(piperidin-4-yl)methyl]-1H-pyrazol-4-yl}-2-(1H-pyrazol-4-yl)-1,3-thiazole-4-carboxamide
N-[3-(difluoromethyl)-1-(tetrahydro-2H-pyran-2-ylmethyl)-1H-pyrazol-4-yl]-2-(1H-pyrazol-4-yl)-1,3-thiazole-4-carboxamide
N-{1-[3-(dimethylamino)propyl]-1H-pyrazol-4-yl}-2-(1H-pyrazol-4-yl)-1,3-thiazole-4-carboxamide
N-[3-(difluoromethyl)-1-(tetrahydro-2H-pyran-4-ylmethyl)-1H-pyrazol-4-yl]-2-(1H-pyrazol-4-yl)-1,3-thiazole-4-carboxamide
N-{1-[(4,4-difluorocyclohexyl)methyl]-1H-pyrazol-4-yl}-2-(1H-pyrazol-4-yl)-1,3-thiazole-4-carboxamide
N-[3-(difluoromethyl)-1-(2-fluoroethyl)-1H-pyrazol-4-yl]-2-(1H-pyrazol-4-yl)-1,3-thiazole-4-carboxamide
2-(1H-pyrazol-4-yl)-N-[1-(tetrahydro-2H-pyran-4-yl)-1H-pyrazol-4-yl]-1,3-thiazole-4-carboxamide
N-[1-(cyclobutylmethyl)-3-(difluoromethyl)-1H-pyrazol-4-yl]-2-(1H-pyrazol-4-yl)-1,3-thiazole-4-carboxamide
N-[3-(difluoromethyl)-1-(tetrahydrofuran-2-ylmethyl)-1H-pyrazol-4-yl]-2-(1H-pyrazol-4-yl)-1,3-thiazole-4-carboxamide
2-(1H-pyrazol-4-yl)-N-[1-(tetrahydrofuran-2-ylmethyl)-1H-pyrazol-4-yl]-1,3-thiazole-4-carboxamide
N-[1-(cyclopropylmethyl)-3-methoxy-1H-pyrazol-4-yl]-2-(1H-pyrazol-4-yl)-1,3-thiazole-4-carboxamide
N-{1-[2-(piperazin-1-yl)ethyl]-1H-pyrazol-4-yl}-2-(1H-pyrazol-4-yl)-1,3-thiazole-4-carboxamide
N-[3-methoxy-1-(tetrahydro-2H-pyran-4-ylmethyl)-1H-pyrazol-4-yl]-2-(1H-pyrazol-4-yl)-1,3-thiazole-4-carboxamide
N-[1-(4-fluorobenzyl)-1H-pyrazol-4-yl]-2-(1H-pyrazol-4-yl)-1,3-thiazole-4-carboxamide
N-[3-(difluoromethyl)-1-(1-methylethyl)-1H-pyrazol-4-yl]-2-(1H-pyrazol-4-yl)-1,3-thiazole-4-carboxamide
N-[1-(cyclobutylmethyl)-3-methoxy-1H-pyrazol-4-yl]-2-(1H-pyrazol-4-yl)-1,3-thiazole-4-carboxamide
N-[1-(2,2-difluoroethyl)-3-methoxy-1H-pyrazol-4-yl]-2-(1H-pyrazol-4-yl)-1,3-thiazole-4-carboxamide
N-[3-methoxy-1-(2-methoxyethyl)-1H-pyrazol-4-yl]-2-(1H-pyrazol-4-yl)-1,3-thiazole-4-carboxamide
N-[1-(2-methoxyethyl)-1H-pyrazol-4-yl]-2-(1H-pyrazol-4-yl)-1,3-thiazole-4-carboxamide
N-[3-(difluoromethyl)-1-(2-methylpropyl)-1H-pyrazol-4-yl]-2-(1H-pyrazol-4-yl)-1,3-thiazole-4-carboxamide
2-(1H-pyrazol-4-yl)-N-[1-(pyridin-4-ylmethyl)-1H-pyrazol-4-yl]-1,3-thiazole-4-carboxamide
N-{1-[(1-cyanocyclopropyl)methyl]-3-methoxy-1H-pyrazol-4-yl}-2-(1H-pyrazol-4-yl)-1,3-thiazole-4-carboxamide
2-(1H-pyrazol-4-yl)-N-(1-{[(3S)-pyrrolidin-3-yl]methyl}-1H-pyrazol-4-yl)-1,3-thiazole-4-carboxamide
N-[1-(cyanomethyl)-3-(difluoromethyl)-1H-pyrazol-4-yl]-2-(1H-pyrazol-4-yl)-1,3-thiazole-4-carboxamide
N-{1-[(4-cyanopiperidin-4-yl)methyl]-1H-pyrazol-4-yl}-2-(1H-pyrazol-4-yl)-1,3-thiazole-4-carboxamide
N-{1-[(2,2-difluorocyclopropyl)methyl]-3-(difluoromethyl)-1H-pyrazol-4-yl}-2-(1H-pyrazol-4-yl)-1,3-thiazole-4-carboxamide
2-(1H-pyrazol-4-yl)-N-(1-{[(3R)-pyrrolidin-3-yl]methyl}-1H-pyrazol-4-yl)-1,3-thiazole-4-carboxamide
N-[1-(1-cyanoethyl)-3-(difluoromethyl)-1H-pyrazol-4-yl]-2-(1H-pyrazol-4-yl)-1,3-thiazole-4-carboxamide
N-{1-[2-(piperidin-4-yl)ethyl]-1H-pyrazol-4-yl}-2-(1H-pyrazol-4-yl)-1,3-thiazole-4-carboxamide
N-[1-(cyclopropylmethyl)-3-(difluoromethyl)-1H-pyrazol-4-yl]-2-(1H-pyrazol-4-yl)-1,3-thiazole-4-carboxamide
N-{1-[3-(4-methylpiperazin-1-yl)propyl]-1H-pyrazol-4-yl}-2-(1H-pyrazol-4-yl)-1,3-thiazole-4-carboxamide -continued

| |
|---|
| N-{1-[(cis-4-amino-1-fluorocyclohexyl)methyl]-1H-pyrazol-4-yl}-2-(1H-pyrazol-4-yl)-1,3-thiazole-4-carboxamide |
| N-(1-{[4-(aminomethyl)-1-fluorocyclohexyl]methyl} -1H-pyrazol-4-yl)-2-(1H-pyrazol-4-yl)-1,3-thiazole-4-carboxamide |
| N-{1-[(4-cyanocyclohexyl)methyl]-1H-pyrazol-4-yl}-2-(1H-pyrazol-4-yl)-1,3-thiazole-4-carboxamide |
| N-[1-(cyclopropylmethyl)-1H-pyrazol-4-yl]-2-(1H-pyrazol-4-yl)-1,3-thiazole-4-carboxamide |
| N-{1-[(2,2-difluorocyclopropyl)methyl]-3-methoxy-1H-pyrazol-4-yl}-2-(1H-pyrazol-4-yl)-1,3-thiazole-4-carboxamide |
| N-[3-(difluoromethyl)-1-(2-ethoxyethyl)-1H-pyrazol-4-yl]-2-(1H-pyrazol-4-yl)-1,3-thiazole-4-carboxamide |
| N-[1-(2-methylpropyl)-1H-pyrazol-4-yl]-2-(1H-pyrazol-4-yl)-1,3-thiazole-4-carboxamide |
| N-{3-(difluoromethyl)-1-[(3-methyloxetan-3-yl)methyl]-1H-pyrazol-4-yl}-2-(1H-pyrazol-4-yl)-1,3-thiazole-4-carboxamide |
| N-{1-[(3-azabicyclo[3.2.1]octan-8-yl)methyl]-1H-pyrazol-4-yl}-2-(1H-pyrazol-4-yl)-1,3-thiazole-4-carboxamide |
| N-(1-(2-Methylpyridin-4-yl)-1H-pyrazol-4-yl)-2-(1H-pyrazol-4-yl)thiazole-4-carboxamide |
| N-[1-(3-methylpyridin-4-yl)-1H-pyrazol-4-yl]-2-(1H-pyrazol-4-yl)-1,3-thiazole-4-carboxamide |
| N-{1-[2-(1-methylethyl)pyridin-4-yl]-1H-pyrazol-4-yl}-2-(1H-pyrazol-4-yl)-1,3-thiazole-4-carboxamide |
| N-[1-(2,6-dimethylpyridin-4-yl)-1H-pyrazol-4-yl]-2-(1H-pyrazol-4-yl)-1,3-thiazole-4-carboxamide |
| N-(1-Cyclobutyl-1H-pyrazol-4-yl)-6-(1-methyl-1H-pyrazol-4-yl)picolinamide |
| N-[1-(cyclobutylmethyl)-1H-pyrazol-4-yl]-6-pyrimidin-5-ylpyridine-2-carboxamide |
| N-(1-cyclobutyl-1H-pyrazol-4-yl)-2-(5,6-dihydro-4H-pyrrolo[1,2-b]pyrazol-3-yl)-1,3-thiazole-4-carboxamide |
| N-(1-cyclobutyl-1H-pyrazol-4-yl)-2-(1-ethyl-1H-pyrazol-4-yl)-1,3-thiazole-4-carboxamide |
| N-[1-(cyclobutylmethyl)-1H-pyrazol-4-yl]-6-furan-3-ylpyridine-2-carboxamide |
| N-[1-(cyclobutylmethyl)-1H-pyrazol-4-yl]-6-[1-(pyridin-4-ylmethyl)-1H-pyrazol-4-yl]pyridine-2-carboxamide |
| N-[1-(cyclobutylmethyl)-1H-pyrazol-4-yl]-6-(6-methyl-6,7-dihydro-5H-pyrazolo[5,1-b][1,3]oxazin-3-yl)pyridine-2-carboxamide |
| N-[1-(cyclobutylmethyl)-1H-pyrazol-4-yl]-6-[1-(pyridin-2-ylmethyl)-1H-pyrazol-4-yl]pyridine-2-carboxamide |
| N-(1-cyclobutyl-1H-pyrazol-4-yl)-2-(1-methyl-1H-imidazol-4-yl)-1,3-thiazole-4-carboxamide |
| N-[1-(cyclobutylmethyl)-1H-pyrazol-4-yl]-6-(6,7-dihydro-4H-pyrazolo[5,1-c][1,4]oxazin-3-yl)pyridine-2-carboxamide |
| N-[1-(cyclobutylmethyl)-1H-pyrazol-4-yl]-6-(2,4-difluorophenyl)pyridine-2-carboxamide |
| N-[1-(cyclobutylmethyl)-1H-pyrazol-4-yl]-6-[1-(2-methoxyethyl)-1H-pyrazol-4-yl]pyridine-2-carboxamide |
| N-[1-(cyclobutylmethyl)-1H-pyrazol-4-yl]-6-(4,5,6,7-tetrahydropyrazolo[1,5-a]pyridin-3-yl)pyridine-2-carboxamide |
| N-(1-cyclobutyl-1H-pyrazol-4-yl)-2-(1H-pyrazol-3-yl)-1,3-thiazole-4-carboxamide |
| N-[1-(cyclobutylmethyl)-1H-pyrazol-4-yl]-6-isothiazol-4-ylpyridine-2-carboxamide |
| N-[1-(cyclobutylmethyl)-1H-pyrazol-4-yl]-2,4'-bipyridine-6-carboxamide |
| N-(1-cyclobutyl-1H-pyrazol-4-yl)-2-[1-(difluoromethyl)-1H-pyrazol-4-yl]-1,3-thiazole-4-carboxamide |
| N-(1-cyclobutyl-1H-pyrazol-4-yl)-2-(5-methyl-1H-pyrazol-4-yl)-1,3-thiazole-4-carboxamide |
| N-[1-(cyclobutylmethyl)-1H-pyrazol-4-yl]-6-pyridazin-4-ylpyridine-2-carboxamide |
| N-[1-(cyclobutylmethyl)-1H-pyrazol-4-yl]-6-(1-methyl-1H-pyrazol-5-yl)pyridine-2-carboxamide |
| N-(1-cyclobutyl-1H-pyrazol-4-yl)-2-(6,7-dihydro-5H-pyrazolo[5,1-b][1,3]oxazin-3-yl)-1,3-thiazole-4-carboxamide |
| N-[1-(cyclobutylmethyl)-1H-pyrazol-4-yl]-6-(1-methyl-1H-pyrazol-3-yl)pyridine-2-carboxamide |
| N-(1-cyclobutyl-1H-pyrazol-4-yl)-2-(1-methyl-1H-pyrazol-4-yl)pyrimidine-4-carboxamide |
| N-[1-(cyclobutylmethyl)-1H-pyrazol-4-yl]-2'-fluoro-2,3'-bipyridine-6-carboxamide |
| N-[1-(cyclobutylmethyl)-1H-pyrazol-4-yl]-6-(1-methyl-1H-pyrazol-4-yl)pyridine-2-carboxamide |
| N-[1-(cyclobutylmethyl)-1H-pyrazol-4-yl]-6-(3,5-dimethyl-1H-pyrazol-4-yl)pyridine-2-carboxamide |
| N-(1-cyclobutyl-1H-pyrazol-4-yl)-2-(4,5,6,7-tetrahydropyrazolo[1,5-a]pyridin-3-yl)-1,3-thiazole-4-carboxamide |
| N-(1-cyclobutyl-1H-pyrazol-4-yl)-2-(1-methyl-1H-pyrazol-4-yl)-1,3-thiazole-4-carboxamide |
| 6-(3-cyanophenyl)-N-[1-(cyclobutylmethyl)-1H-pyrazol-4-yl]pyridine-2-carboxamide |
| N-[1-(cyclobutylmethyl)-1H-pyrazol-4-yl]-4'-methoxy-2,3'-bipyridine-6-carboxamide |
| 6-(1-benzothiophen-3-yl)-N-[1-(cyclobutylmethyl)-1H-pyrazol-4-yl]pyridine-2-carboxamide |

-continued

| |
|---|
| N-[1-(cyclobutylmethyl)-1H-pyrazol-4-yl]-6-(1-methyl-1H-pyrrol-3-yl)pyridine-2-carboxamide |
| N-[1-(cyclobutylmethyl)-1H-pyrazol-4-yl]-6-[1-(difluoromethyl)-1H-pyrazol-4-yl]pyridine-2-carboxamide |
| N-[1-(cyclobutylmethyl)-1H-pyrazol-4-yl]-2,3'-bipyridine-6-carboxamide |
| N-[1-(cyclobutylmethyl)-1H-pyrazol-4-yl]-6-[1-(2-morpholin-4-ylethyl)-1H-pyrazol-4-yl]pyridine-2-carboxamide |
| N-[1-(cyclobutylmethyl)-1H-pyrazol-4-yl]-6-[1-(pyridin-3-ylmethyl)-1H-pyrazol-4-yl]pyridine-2-carboxamide |
| N-(1-cyclobutyl-1H-pyrazol-4-yl)-6-(1-methyl-1H-pyrazol-4-yl)pyrazine-2-carboxamide |
| N-(1-cyclobutyl-1H-pyrazol-4-yl)-2-fluoro-3-(1-methyl-1H-pyrazol-4-yl)benzamide |
| N-(1-cyclobutyl-1H-pyrazol-4-yl)-2-(pyridin-3-yl)thiazole-4-carboxamide |
| N-(1-cyclopropyl-1H-pyrazol-4-yl)-2-(1H-pyrazol-5-yl)thiazole-4-carboxamide |
| 6-(1-Cyanocyclopropyl)-N-(1-(cyclobutylmethyl)-1H-pyrazol-4-yl)picolinamide |
| N-(1-Cyclobutyl-1H-pyrazol-4-yl)-2-(1H-pyrazol-1-yl)thiazole-4-carboxamide |
| N-(1-cyclobutyl-1H-pyrazol-4-yl)-2-(1H-imidazol-1-yl)thiazole-4-carboxamide |
| N-(1-(Cyclobutylmethyl)-1H-pyrazol-4-yl)-2-(1-methyl-1H-pyrazol-4-yl)thiazole-4-carboxamide |
| N-(1-cyclobutyl-3-cyclopropyl-1H-pyrazol-4-yl)-2-(1-methyl-1H-pyrazol-4-yl)-1,3-thiazole-4-carboxamide |
| N-(1,3-dicyclopropyl-1H-pyrazol-4-yl)-2-(1-methyl-1H-pyrazol-4-yl)-1,3-thiazole-4-carboxamide |
| 2-(1-ethyl-1H-pyrazol-4-yl)-N-[3-methoxy-1-(2,2,2-trifluoroethyl)-1H-pyrazol-4-yl]-1,3-thiazole-4-carboxamide |
| N-(1-cyclobutyl-3-methyl-1H-pyrazol-4-yl)-2-(1-methyl-1H-pyrazol-4-yl)-1,3-thiazole-4-carboxamide |
| N-[3-methoxy-1-(2,2,2-trifluoroethyl)-1H-pyrazol-4-yl]-2-(1-methyl-1H-pyrazol-4-yl)-1,3-thiazole-4-carboxamide |
| N-(3-Methoxy-1-(2,2,2-trifluoroethyl)-1H-pyrazol-4-yl)-2-(1-(methylsulfonyl)-1H-pyrazol-4-yl)thiazole-4-carboxamide |

16. A pharmaceutical composition comprising a compound of claim 1 and a pharmaceutically acceptable carrier.

17. A method of treating Parkinson's Disease comprising administering an effective amount of a compound of any of claim 1 or a pharmaceutically acceptable salt thereof, to a person in need thereof.

18. A method for the treatment or prophylaxis of an condition in which LRRK2 kinase is involved comprising administering to a subject in need thereof an effective amount of a compound according to claim 1 or a pharmaceutically acceptable salt thereof, said condition selected from:

abnormal motor symptoms associated with Parkinson's disease, non-motor symptoms associated with Parkinson's disease, Lewy body dementia, L-Dopa induced dyskinesias, Alzheimer's disease, mild cognitive impairment, the transition from mild cognitive impairment to Alzheimer's disease, tauopathy disorders characterized by hyperphosphorylation of tau argyrophilic grain disease, Picks disease, corticobasal degeneration, progressive supranuclear palsy, inherited frontotemporal dementia, and Parkinson's disease linked to chromosome 17, neuroinflammation associated with of microglial inflammatory responses associated with multiple sclerosis, HIV-induced dementia, ALS, ischemic stroke, traumatic brain injury and spinal cord injury, lymphomas, leukemias, multiple sclerosis, rheumatoid arthritis, systemic lupus erythematosus, autoimmune hemolytic anemia, pure red cell aplasia, idiopathic thrombocytopenia pupura (ITP), Evans Syndrome, vasculitis, bullous skin disorder, type I diabetes mellitus, Sjorgen's syndrome, Delvic's disease, inflammatory myopathies, and ankylosing spondylitis, renal cancer, breast cancer, lung cancer, prostate cancer, and acute myelogenous leukemia (AML) in subjects expressing the LRRK2 G2019S mutation, papillary renal and thyroid carcinomas in a subject in whom LRRK2 is amplified or overexpressed, Crohn's disease and leprosy.

* * * * *